(12) United States Patent
Baldwin et al.

(10) Patent No.: US 12,144,728 B2
(45) Date of Patent: Nov. 19, 2024

(54) TRANSCATHETER HEART VALVE PROSTHESES

(71) Applicant: Medtronic, Inc., Minneapolis, MN (US)

(72) Inventors: Matthew Baldwin, Santa Rosa, CA (US); Amy Hallak, Tustin, CA (US); Rodney Bell, Galway (IE); Matthew Weston, Roseville, MN (US); Yogesh Darekar, Irvine, CA (US); Wayne Falk, Minneapolis, MN (US); David Michael Martin, Oranmore (IE); Mike Conerney, Loughrea (IE); David Nolan, Freshford (IE); Cahal McVeigh, White Bear Township, MN (US); Karl Olney, Irvine, CA (US); Jamie Dunaway, Santa Rosa, CA (US); Fatemeh Fatemi Far, Santa Rosa, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 330 days.

(21) Appl. No.: 17/540,304

(22) Filed: Dec. 2, 2021

(65) Prior Publication Data

US 2022/0175521 A1 Jun. 9, 2022

Related U.S. Application Data

(60) Provisional application No. 63/251,305, filed on Oct. 1, 2021, provisional application No. 63/251,324, filed (Continued)

(51) Int. Cl.
*A61F 2/24* (2006.01)
*A61F 2/82* (2013.01)

(52) U.S. Cl.
CPC .... *A61F 2/2418* (2013.01); *A61F 2250/0036* (2013.01); *A61F 2250/0037* (2013.01)

(58) Field of Classification Search
CPC ........ A61F 2/24; A61F 2/2409; A61F 2/2418; A61F 2250/0039; A61F 2/07;
(Continued)

(56) References Cited

U.S. PATENT DOCUMENTS 7,972,378 B2 * 7/2011 Tabor ...................... A61F 2/013
623/1.24
8,778,011 B2 7/2014 Ryan
(Continued)

FOREIGN PATENT DOCUMENTS

WO WO-2009029199 A1 * 3/2009 ........... A61F 2/2409
WO 2009094188 A2 7/2009
WO 2020190855 A1 9/2020

OTHER PUBLICATIONS

International Search Report and Written Opinion issued Mar. 21, 2022 in Intl Appl. No. PCT/US2021/061971.

*Primary Examiner* — Seema Mathew
(74) *Attorney, Agent, or Firm* — MEDLER FERRO WOODHOUSE & MILLS PLLC

(57) ABSTRACT

Transcatheter aortic valve prostheses for improving the cardiac function of a patient suffering from coronary artery disease. Transcatheter aortic valve prostheses include a valve component and a frame. The valve component includes valve leaflets and a skirt. The frame includes access cells that improve access to a patient's coronary arteries if further intervention is required and/or includes a window or conduction protection cell that is oriented to align with a portion of conduction system of the heart in situ to reduce conduction disturbances of the anatomy. Suture patterns for attaching a commissure to a commissure post of the frame, (Continued)

and for attaching a tissue bumper to the commissure post, are also described.

38 Claims, 32 Drawing Sheets

Related U.S. Application Data on Oct. 1, 2021, provisional application No. 63/251,315, filed on Oct. 1, 2021, provisional application No. 63/122,461, filed on Dec. 7, 2020.

(58) Field of Classification Search
CPC ...... A61F 2250/0018; A61F 2/86; A61F 2/82; A61F 2/90; A61F 2/89
See application file for complete search history.

(56) References Cited

U.S. PATENT DOCUMENTS

| | | | |
|---|---|---|---|
| 8,882,831 B2* | 11/2014 | Alkhatib | A61F 2/2418 623/2.17 |
| 9,987,133 B2* | 6/2018 | Straubinger | A61F 2/2412 |
| 10,016,274 B2* | 7/2018 | Tabor | A61F 2/07 |
| 10,321,994 B2* | 6/2019 | Erzberger | A61F 2/2418 |
| 10,441,413 B2* | 10/2019 | Tabor | A61F 2/2409 |
| 10,709,555 B2 | 7/2020 | Schreck et al. | |
| 10,709,557 B2* | 7/2020 | Essinger | A61F 2/2436 |
| 10,722,352 B2 | 7/2020 | Spence | |
| 10,736,738 B2 | 8/2020 | Bell et al. | |
| 10,856,970 B2* | 12/2020 | Tuval | A61F 2/2433 |
| 10,966,821 B2* | 4/2021 | Delaloye | A61F 2/2409 |
| 2006/0122692 A1* | 6/2006 | Gilad | A61F 2/2418 623/1.35 |
| 2006/0190074 A1* | 8/2006 | Hill | A61F 2/2475 623/2.18 |
| 2007/0043435 A1* | 2/2007 | Seguin | A61F 2/2433 623/2.11 |
| 2007/0100435 A1* | 5/2007 | Case | A61F 2/2418 623/901 |
| 2010/0168839 A1 | 7/2010 | Braido et al. | |
| 2010/0185277 A1* | 7/2010 | Braido | A61F 2/2409 623/2.37 |
| 2010/0249911 A1* | 9/2010 | Alkhatib | A61F 2/2418 623/1.26 |
| 2010/0249923 A1* | 9/2010 | Alkhatib | A61F 2/2409 623/2.18 |
| 2011/0098800 A1* | 4/2011 | Braido | A61F 2/2418 623/1.26 |
| 2011/0238168 A1* | 9/2011 | Pellegrini | A61F 2/2433 623/2.17 |
| 2011/0251683 A1* | 10/2011 | Tabor | A61F 2/2436 623/2.11 |
| 2014/0142694 A1* | 5/2014 | Tabor | A61F 2/07 623/2.18 |
| 2014/0236292 A1* | 8/2014 | Braido | A61F 2/2418 623/2.38 |
| 2014/0330371 A1* | 11/2014 | Gloss | A61F 2/07 623/2.17 |
| 2015/0209140 A1* | 7/2015 | Bell | A61F 2/2418 623/2.18 |
| 2015/0216658 A1* | 8/2015 | Braido | A61F 2/2433 623/2.13 |
| 2017/0049566 A1* | 2/2017 | Zeng | A61F 2/2418 |
| 2017/0079786 A1* | 3/2017 | Li | A61F 2/2418 |
| 2017/0325946 A1* | 11/2017 | Bell | A61F 2/2418 |
| 2019/0151091 A1* | 5/2019 | Dwork | A61F 2/2469 |
| 2020/0337837 A1* | 10/2020 | Mitra | A61F 2/2433 |
| 2021/0038380 A1* | 2/2021 | Tabor | A61F 2/013 |
| 2021/0275298 A1* | 9/2021 | Peterson | A61F 2/2418 |
| 2022/0054260 A1* | 2/2022 | Koop | A61F 2/2418 |
| 2022/0175521 A1* | 6/2022 | Baldwin | A61F 2/2418 |
| 2022/0233305 A1* | 7/2022 | Yohanan | A61F 2/2412 |
| 2023/0218390 A1 | 7/2023 | Pisani et al. | |
| 2024/0024101 A1* | 1/2024 | Levi | A61F 2/2418 |
| 2024/0173127 A1* | 5/2024 | Clapp | A61F 2/2436 |

* cited by examiner

| Prosthesis Size | Strut Type | Inflow end root width | Outflow end root width | Mid width | % Width taper | Length | % Length change |
|---|---|---|---|---|---|---|---|
| 23 | $118_{4\text{-}1}$ and $118_{4\text{-}2}$ | RW1 = 0.26 | RW4 = 0.30 | MW1 = 0.16 | 0.6 | L1 = 4.71 | 1.03 |
| | $118_{4\text{-}3}$ and $118_{4\text{-}4}$ | RW2 = 0.36 | RW5 = 0.30 | MW2 = 0.22 | 0.6 | L2 = 4.71 | 1.03 |
| | $111_4$ | RW3 = 0.30 | RW6 = 0.30 | MW3 = 0.19 | 0.65 | L3 = 4.57 | |
| 26 | $118_{4\text{-}1}$ and $118_{4\text{-}2}$ | RW1 = 0.24 | RW4 = 0.24 | MW1 = 0.16 | 0.65 | L1 = 4.62 | 1.1 |
| | $118_{4\text{-}3}$ and $118_{4\text{-}4}$ | RW2 = 0.31 | RW5 = 0.24 | MW2 = 0.19 | 0.63 | L2 = 4.62 | 1.1 |
| | $111_4$ | RW3 = 0.24 | RW6 = 0.24 | MW3 = 0.16 | 0.67 | L3 = 4.20 | |
| 29 | $118_{4\text{-}1}$ and $118_{4\text{-}2}$ | RW1 = 0.24 | RW4 = 0.29 | MW1 = 0.21 | 0.89 | L1 = 4.83 | 1.1 |
| | $118_{4\text{-}3}$ and $118_{4\text{-}4}$ | RW2 = 0.30 | RW5 = 0.29 | MW2 = 0.20 | 0.65 | L2 = 4.83 | 1.1 |
| | $111_4$ | RW3 = 0.29 | RW6 = 0.29 | MW3 = 0.17 | 0.59 | L3 = 4.40 | |
| 34 | $118_{4\text{-}1}$ and $118_{4\text{-}2}$ | RW1 = 0.30 | RW4 = 0.39 | MW1 = 0.27 | 0.9 | L1 = 4.46 | 1.02 |
| | $118_{4\text{-}3}$ and $118_{4\text{-}4}$ | RW2 = 0.40 | RW5 = 0.39 | MW2 = 0.24 | 0.6 | L2 = 4.46 | 1.02 |
| | $111_4$ | RW3 = 0.36 | RW6 = 0.39 | MW3 = 0.22 | 0.61 | L3 = 4.37 | |

FIG. 3E

| Prosthesis Size | Strut Type | Inflow end root width | Outflow end root width | Mid width | % Width taper | Length | % Length change |
|---|---|---|---|---|---|---|---|
| 23 | $118_{7\text{-}1}$ and $118_{7\text{-}2}$ | RW7 = 0.29 | RW10 = 0.26 | MW4 = 0.16 | 0.6 | L4 = 6.74 | 1.02 |
| | $118_{7\text{-}3}$ and $118_{7\text{-}4}$ | RW8 = 0.29 | RW11 = 0.26 | MW5 = 0.16 | 0.6 | L5 = 6.74 | 1.02 |
| | $111_7$ | RW9 = 0.29 | RW12 = 0.29 | MW6 = 0.19 | 0.65 | L6 = 6.60 | |
| 26 | $118_{7\text{-}1}$ and $118_{7\text{-}2}$ | RW7 = 0.29 | RW10 = 0.24 | MW4 = 0.16 | 0.65 | L4 = 5.03 | 0.99 |
| | $118_{7\text{-}3}$ and $118_{7\text{-}4}$ | RW8 = 0.29 | RW11 = 0.31 | MW5 = 0.20 | 0.65 | L5 = 5.03 | 0.99 |
| | $111_7$ | RW9 = 0.29 | RW12 = 0.28 | MW6 = 0.19 | 0.65 | L6 = 5.10 | |
| 29 | $118_{7\text{-}1}$ and $118_{7\text{-}2}$ | RW7 = 0.29 | RW10 = 0.24 | MW4 = 0.16 | 0.65 | L4 = 4.78 | 0.96 |
| | $118_{7\text{-}3}$ and $118_{7\text{-}4}$ | RW8 = 0.29 | RW11 = 0.36 | MW5 = 0.23 | 0.65 | L5 = 4.78 | 0.96 |
| | $111_7$ | RW9 = 0.29 | RW12 = 0.29 | MW6 = 0.19 | 0.67 | L6 = 5.00 | |
| 34 | $118_{7\text{-}1}$ and $118_{7\text{-}2}$ | RW7 = 0.34 | RW10 = 0.28 | MW4 = 0.17 | 0.6 | L4 = 4.55 | 0.96 |
| | $118_{7\text{-}3}$ and $118_{7\text{-}4}$ | RW8 = 0.34 | RW11 = 0.38 | MW5 = 0.23 | 0.6 | L5 = 4.55 | 0.96 |
| | $111_7$ | RW9 = 0.33 | RW12 = 0.33 | MW6 = 0.21 | 0.64 | L6 = 4.72 | |

FIG. 3G

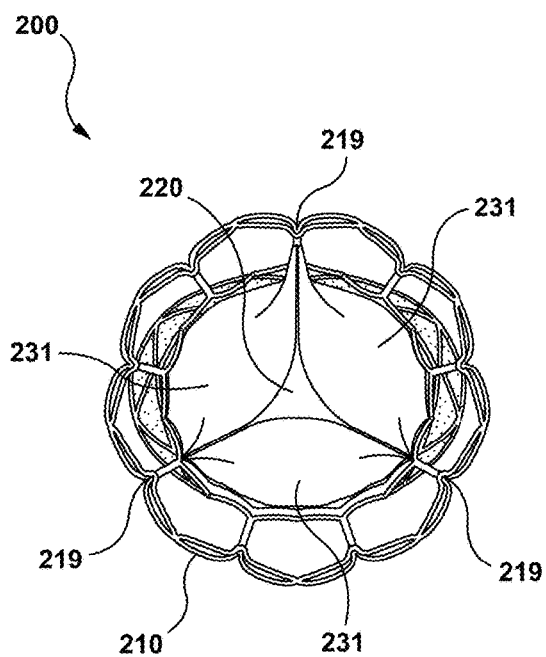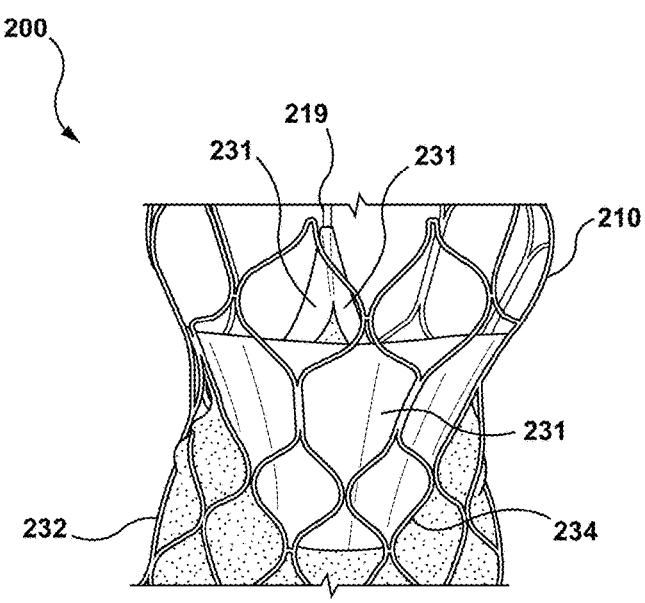
FIG. 7B
FIG. 7C

TRANSCATHETER HEART VALVE PROSTHESES

CROSS-REFERENCE TO RELATED APPLICATIONS

This application claims the benefit of U.S. Provisional Patent Application Ser. No. 63/251,324, filed Oct. 1, 2021; U.S. Provisional Patent Application Ser. No. 63/251,315, filed Oct. 1, 2021; U.S. Provisional Patent Application Ser. No. 63/251,305, filed Oct. 1, 2021; and U.S. Provisional Patent Application Ser. No. 63/122,461, filed Dec. 7, 2020, each of which is hereby incorporated by reference in its entirety for all purposes.

FIELD OF THE INVENTION

The present invention relates to transcatheter aortic valve prostheses that facilitate access to a patient's coronary arteries and/or reduce conduction disturbances.

BACKGROUND

The human heart is a four chambered, muscular organ that provides blood circulation through the body during a cardiac cycle. The four main chambers include the right atrium and right ventricle which supplies the pulmonary circulation, and the left atrium and left ventricle which supplies oxygenated blood received from the lungs into systemic circulation. To ensure that blood flows in one direction through the heart, atrioventricular valves (tricuspid and mitral valves) are present between the junctions of the atrium and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The valve leaflets move apart from each other to open and allow blood to flow downstream of the valve, and coapt to close and prevent backflow or regurgitation in an upstream manner.

The conduction system of the heart consists of cardiac muscle cells and conducting fibers that are specialized for initiating electrical impulses and conducting them rapidly through the heart. These impulses initiate the normal rhythmic cardiac cycle and coordinate the contractions of the cardiac chambers. The conduction system of the heart consists of the sinoatrial (SA) node, the atrioventricular (AV) node, the atrioventricular bundle (bundle of His), and Purkinje fibers. The SA node, a collection of specialized pacemaker cells, creates an excitation signal which spreads across the atria, causing them to contract. When the signal reaches the AV node, the AV node delays the impulses to ensure the atria have enough time to fully contract. The atrioventricular bundle (bundle of His) is a continuation of the specialized tissue of the AV node, and serves to transmit the electrical impulse from the AV node to the Purkinje fibers of the ventricles, causing the ventricles to contract.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based delivery systems. Such heart valve prostheses are delivered in a radially compressed or crimped configuration so that the heart valve prosthesis can be advanced through the patient's vasculature. Once positioned at the treatment site, the heart valve prosthesis is expanded to engage tissue at the diseased heart valve region to, for instance, hold the heart valve prosthesis in position.

The present disclosure relates to improvements in heart valve prostheses for improving the cardiac function of a patient suffering from coronary artery disease. More particularly, the present invention relates to transcatheter aortic valve prostheses that provide improved access to a patient's coronary arteries if the patient requires a percutaneous coronary intervention procedure post-implantation of the transcatheter aortic valve prosthesis and/or reduce conduction disturbances in order to mitigate permanent pacemaker implantation rates.

BRIEF SUMMARY OF THE INVENTION

According to a first embodiment hereof, the present disclosure provides a transcatheter aortic valve prosthesis for replacement of a native heart valve. The transcatheter aortic valve prosthesis includes a frame having a plurality of struts, a plurality of crowns at an inflow end, a plurality of crowns at an outflow end, a plurality of commissure posts or commissure cells, a plurality of first cells, and at least one access cell, and a valve component including two or more valve leaflets disposed within the frame. A commissure is formed where two valve leaflets of the two or more valve leaflets are attached to each other and each commissure is secured to a commissure post or commissure cell of the plurality of commissure posts or commissure cells of the frame. An area of a first cell directly adjacent to the at least one access cell has a first area and the at least one access cell has a second area. The first area is between approximately 12% and approximately 33% of the second area. The at least one access cell is centered in a circumferential direction between two commissure posts or commissure cells of the plurality of commissure posts or commissure cells of the frame.

In an aspect of the first embodiment, and in combination with any other aspects herein, the disclosure provides that the first area is approximately 25% of the second area.

In an aspect of the first embodiment, and in combination with any other aspects herein, the disclosure provides that the first area is approximately 33% of the second area.

In an aspect of the first embodiment, and in combination with any other aspects herein, the disclosure provides that the first area is approximately 14% of the second area.

In an aspect of the first embodiment, and in combination with any other aspects herein, the disclosure provides that the first area is approximately 12% of the second area.

In an aspect of the first embodiment, and in combination with any other aspects herein, the disclosure provides that the frame includes a row of the plurality of struts which includes a plurality of standard struts and a plurality of optimized strut. Each standard strut of the plurality of standard struts has a first width profile and a first length. Each optimized strut of the plurality of optimized struts having a width profile that is different from the first width profile and a length that is different from the first length.

In an aspect of the first embodiment, and in combination with any other aspects herein, the disclosure provides that the plurality of optimized struts include a first optimized strut, a second optimized strut, a third optimized strut, and a fourth optimized strut. The first optimized strut and the second optimized strut enclose a portion of the at least one access cell. The third optimized strut is disposed directly adjacent to the first optimized strut and the fourth optimized strut is disposed directly adjacent to the second optimized strut.

In an aspect of the first embodiment, and in combination with any other aspects herein, the disclosure provides that the row of the plurality of struts which includes the plurality of standard struts and the plurality of optimized struts is disposed at an inflow end or an outflow end of the at least one access cell.

In an aspect of the first embodiment, and in combination with any other aspects herein, the disclosure provides that the row of the plurality of struts which includes the plurality of standard struts and the plurality of optimized struts is a first row and the first row is disposed at the inflow end of the at least one access cell. The frame also includes a second row of the plurality of struts which includes the plurality of standard struts and the plurality of optimized struts and the second row is disposed at the outflow end of the at least one access cell.

In an aspect of the first embodiment, and in combination with any other aspects herein, the disclosure provides that the frame includes exactly fifteen crowns at the inflow end, exactly fifteen crowns at the outflow end, at least nine rows of first cells, and exactly three access cells. The frame further includes exactly three commissure cells.

In an aspect of the first embodiment, and in combination with any other aspects herein, the disclosure provides that the frame includes exactly nine crowns at the inflow end, exactly nine crowns at the outflow end, at least four rows of first cells, and exactly one row of access cells.

In an aspect of the first embodiment, and in combination with any other aspects herein, the disclosure provides that the one row of access cells includes exactly nine access cells. The frame further includes exactly three commissure posts.

In an aspect of the first embodiment, and in combination with any other aspects herein, the disclosure provides that the frame includes exactly twelve crowns at the inflow end, exactly six crowns at the outflow end, at least four rows of first cells, and exactly one row of access cells.

In an aspect of the first embodiment, and in combination with any other aspects herein, the disclosure provides that the one row of access cells includes exactly six access cells. The frame further includes exactly three commissure posts.

In an aspect of the first embodiment, and in combination with any other aspects herein, the disclosure provides that the frame includes exactly twelve crowns at the inflow end, exactly twelve crowns at the outflow end, at least seven rows of first cells, and exactly one row of access cells. The one row of access cells includes exactly three access cells. The frame further includes exactly three commissure posts.

In an aspect of the first embodiment, and in combination with any other aspects herein, the disclosure provides that the at least one access cell is configured to be aligned with an ostium of a coronary artery in situ.

According to a second embodiment hereof, the present disclosure provides a transcatheter aortic valve prosthesis for replacement of a native heart valve. The transcatheter aortic valve prosthesis comprises a frame having a plurality of struts, a plurality of crowns at an inflow end, a plurality of crowns at an outflow end, a plurality of commissure posts or commissure cells, a plurality of first cells, and at least one access cell. The frame includes a row of the plurality of struts which includes a plurality of standard struts and a plurality of optimized struts. Each standard strut of the plurality of standard struts has a first width profile and a first length. Each optimized strut of the plurality of optimized struts has a width profile that is different from the first width profile and a length that is different from the first length. A valve component includes two or more valve leaflets disposed within the frame. A commissure is formed where two valve leaflets of the two or more valve leaflets are attached to each other and each commissure is secured to a commissure post or a commissure cell of the plurality of commissure posts or commissure cells of the frame. An area of a first cell directly adjacent to the at least one access cell has a first area and the at least one access cell has a second area. The second area is at least twice as large as the first area. The at least one access cell is centered in a circumferential direction between two commissure posts or commissure cells of the plurality of commissure posts or commissure cells of the frame. The row of the plurality of struts which includes the plurality of standard struts and the plurality of optimized struts is disposed at an inflow end or an outflow end of the at least one access cell.

In an aspect of the second embodiment, and in combination with any other aspects herein, the disclosure provides that the first area is approximately 25% of the second area.

In an aspect of the second embodiment, and in combination with any other aspects herein, the disclosure provides that the first area approximately 33% of the second area.

In an aspect of the second embodiment, and in combination with any other aspects herein, the disclosure provides that the first area is approximately 14% of the second area.

In an aspect of the second embodiment, and in combination with any other aspects herein, the disclosure provides that the first area is approximately 12% of the second area.

In an aspect of the second embodiment, and in combination with any other aspects herein, the disclosure provides that the plurality of optimized struts include a first optimized strut, a second optimized strut, a third optimized strut, and a fourth optimized strut. The first optimized strut and the second optimized strut enclose a portion of the at least one access cell. The third optimized strut is disposed directly adjacent to the first optimized struts and the fourth optimized strut is disposed directly adjacent to the second optimized strut.

In an aspect of the second embodiment, and in combination with any other aspects herein, the disclosure provides that the row of the plurality of struts which includes the plurality of standard struts and the plurality of optimized struts is a first row and the first row is disposed at the inflow end of the at least one access cell. The frame also includes a second row of the plurality of struts which includes the plurality of standard struts and the plurality of optimized struts and the second row is disposed at the outflow end of the at least one access cell.

In an aspect of the second embodiment, and in combination with any other aspects herein, the disclosure provides that the frame includes exactly fifteen crowns at the inflow end, exactly fifteen crowns at the outflow end, at least nine rows of first cells, and exactly three access cells. The frame further includes exactly three commissure cells.

In an aspect of the second embodiment, and in combination with any other aspects herein, the disclosure provides that the frame includes exactly nine crowns at the inflow end, exactly nine crowns at the outflow end, at least four rows of first cells, and exactly one row of access cells.

In an aspect of the second embodiment, and in combination with any other aspects herein, the disclosure provides that the one row of access cells includes exactly nine access cells. The frame further includes exactly three commissure posts.

In an aspect of the second embodiment, and in combination with any other aspects herein, the disclosure provides that the frame includes exactly twelve crowns at the inflow end, exactly six crowns at the outflow end, at least four rows of first cells, and exactly one row of access cells.

In an aspect of the second embodiment, and in combination with any other aspects herein, the disclosure provides that the one row of access cells includes exactly six access cells. The frame further includes exactly three commissure posts.

In an aspect of the second embodiment, and in combination with any other aspects herein, the disclosure provides that the frame includes exactly twelve crowns at the inflow end, exactly twelve crowns at the outflow end, at least seven rows of first cells, and exactly one row of access cells.

In an aspect of the second embodiment, and in combination with any other aspects herein, the disclosure provides that the one row of access cells includes exactly three access cells. The frame includes further includes exactly three commissure posts.

In an aspect of the second embodiment, and in combination with any other aspects herein, the disclosure provides that the at least one access cell is configured to be aligned with an ostium of a coronary artery in situ.

According to a third embodiment hereof, the present disclosure provides a transcatheter aortic valve prosthesis for replacement of a native heart valve. The transcatheter aortic valve prosthesis includes a frame having a plurality of struts, a plurality of crowns at an inflow end, a plurality of crowns at an outflow end, a plurality of first cells, and a window disposed at the inflow end of the frame or a conduction protection cell disposed at the inflow end of the frame, and a valve component including one or more valve leaflets disposed within the frame. A first cell directly adjacent to the window or the conduction protection cell has a first area and the least one window or the conduction protection cell has a second area. The second area is at least twice as large as the first area. The window or the conduction protection cell is positioned to align with a portion of the conduction system of the heart in situ.

In an aspect of the third embodiment, and in combination with any other aspects herein, the disclosure provides that the least one window or the conduction protection cell has a first area extending approximately 60 degrees of a circumference of the frame.

In an aspect of the third embodiment, and in combination with any other aspects herein, the disclosure provides that the frame also includes a plurality of access cells and a plurality of commissure posts or commissure cells. The frame includes at least four rows of first cells and a row of access cells. An area of a first cell directly adjacent to the at least one access cell has a first area and the at least one access cell has a second area. The first area is approximately 33% of the second area. The at least one access cell is centered in a circumferential direction between two commissure posts or commissure cells of the plurality of commissure posts or commissure cells of the frame. The at least one access cell is configured to facilitate access to a patient's coronary arteries.

In an aspect of the third embodiment, and in combination with any other aspects herein, the disclosure provides that the frame includes exactly nine crowns at the inflow end, exactly nine crowns at the outflow end, at least four rows of first cells, and exactly one row of access cells.

In an aspect of the third embodiment, and in combination with any other aspects herein, the disclosure provides that the frame includes the conduction protection cell disposed at the inflow end of the frame that is defined by crowns and struts of the inflow end of the frame.

In an aspect of the third embodiment, and in combination with any other aspects herein, the disclosure provides that the frame includes the window disposed at the inflow end of the frame that creates a circumferential gap along the inflow end of the frame that does not include any crowns or struts of the frame.

In an aspect of the third embodiment, and in combination with any other aspects herein, the disclosure provides that a frame support section disposed within the window to support the circumferential gap created by the window. The frame support section is formed from a polymeric material of a fabric material.

In an aspect of the third embodiment, and in combination with any other aspects herein, the disclosure provides that the window extends approximately 60 degrees of a circumference of the frame.

In an aspect of the third embodiment, and in combination with any other aspects herein, the disclosure provides that the frame also includes a plurality of access cells and a plurality of commissure posts or commissure cells. The frame includes at least four rows of first cells and a row of access cells. An area of a first cell directly adjacent to the at least one access cell has a first area and the at least one access cell has a second area. The first area being approximately 33% of the second area. The at least one access cell is centered in a circumferential direction between two commissure posts or commissure cells of the plurality of commissure posts or commissure cells of the frame. The at least one access cell is configured to facilitate access to a patient's coronary arteries.

In an aspect of the third embodiment, and in combination with any other aspects herein, the disclosure provides that the frame includes exactly nine crowns at the inflow end, exactly nine crowns at the outflow end, at least four rows of first cells, and exactly one row of access cells.

In an aspect of the third embodiment, and in combination with any other aspects herein, the disclosure provides that the frame support section includes at least four struts that form a diamond-shaped cell.

In an aspect of the third embodiment, and in combination with any other aspects herein, the disclosure provides that the frame support section further includes at least three struts that attach the diamond-shaped cell to the frame.

In an aspect of the third embodiment, and in combination with any other aspects herein, the disclosure provides that two of the at least four struts that form the diamond-shaped cell form a polymeric or fabric crown at the inflow end of the frame. The polymeric or fabric crown is longitudinally aligned with the plurality of crowns at the inflow end of the frame.

In an aspect of the third embodiment, and in combination with any other aspects herein, the disclosure provides that an area of the diamond-shaped cell is approximately equivalent to the first area.

In an aspect of the third embodiment, and in combination with any other aspects herein, the disclosure provides that the frame is formed from stainless steel or a nickel titanium alloy.

According to a fourth embodiment hereof, the disclosure provides a transcatheter aortic valve prosthesis for replacement of a native heart valve. The transcatheter aortic valve prosthesis includes a frame having a plurality of struts, a plurality of crowns at an inflow end, a plurality of crowns at an outflow end, a plurality of first cells, wherein the inflow end of the frame includes a row of the plurality of struts which includes a plurality of standard struts and a plurality of non-flared struts, and a valve component including one or more valve leaflets disposed within the frame. Each standard strut of the plurality of standard struts flares radially outward when the frame is in an expanded configuration. Each non-flared strut of the plurality of non-flared struts does not flare radially outward when the frame is in the expanded configuration such that crowns disposed between a pair of non-flared struts at the inflow end are disposed radially inward relative to crowns disposed between a pair of standard struts. The non-flared struts of the frame are positioned to align with a portion of the conduction system of the heart in situ.

In an aspect of the fourth embodiment, and in combination with any other aspects herein, the disclosure provides that crowns disposed between a pair of non-flared struts at the inflow end are displaced radially inward from a circumference of the frame outlined by the rest of the crowns at the inflow end.

In an aspect of the fourth embodiment, and in combination with any other aspects herein, the disclosure provides that each non-flared strut of the plurality of non-flared struts extends radially inwards relative to each standard strut.

In an aspect of the fourth embodiment, and in combination with any other aspects herein, the disclosure provides that each non-flared struts of the plurality of non-flared struts has a shorter height than a height of the standard struts.

In an aspect of the fourth embodiment, and in combination with any other aspects herein, the disclosure provides that each non-flared strut of the plurality of non-flared struts has a first height that is 5-15% shorter than a second height of the standard struts.

According to a fifth embodiment hereof, the present disclosure provides a transcatheter aortic valve prosthesis for replacement of a native heart valve. The transcatheter aortic valve prosthesis includes a frame having a plurality of struts, a plurality of crowns at an inflow end, a plurality of crowns at an outflow end, a plurality of first cells, wherein the inflow end of the frame includes a row of the plurality of struts which includes a plurality of standard struts and a plurality of thinner struts, and a valve component including one or more valve leaflets disposed within the frame. Each standard strut of the plurality of standard struts has a first thickness profile. Each thinner strut of the plurality of thinner struts has a thickness profile that is different from the first thickness profile. The thinner struts of the frame are positioned to align with a portion of the conduction system of the heart in situ.

In an aspect of the fifth embodiment, and in combination with any other aspects herein, the disclosure provides that each thinner strut of the plurality of thinner struts includes a triangular cut-out portion.

In an aspect of the fifth embodiment, and in combination with any other aspects herein, the disclosure provides that the triangular cut-out portion reduces a second thickness of each thinner strut by between 20% and 30% relative a first thickness of each standard strut.

In an aspect of the fifth embodiment, and in combination with any other aspects herein, the disclosure provides that each thinner strut of the plurality of thinner struts includes a rectangular cut-out portion.

In an aspect of the fifth embodiment, and in combination with any other aspects herein, the disclosure provides that the rectangular cut-out portion reduces a second thickness of each thinner strut by between 35% and 45% relative a first thickness of each standard strut.

In an aspect of the fifth embodiment, and in combination with any other aspects herein, the disclosure provides that each thinner strut of the plurality of thinner struts includes a semi-circular cut-out portion.

In an aspect of the fifth embodiment, and in combination with any other aspects herein, the disclosure provides that the semi-circular cut-out portion reduces a second thickness of each thinner strut by between 5% and 15% relative a first thickness of each standard strut.

In an aspect of the fifth embodiment, and in combination with any other aspects herein, the disclosure provides that the first thickness profile is uniform thickness along an entire length of each standard strut.

According to a sixth embodiment hereof, the present disclosure provides a transcatheter aortic valve prosthesis for replacement of a native heart valve. The transcatheter aortic valve prosthesis includes a frame having a plurality of struts, a plurality of first cells, and a plurality of commissure posts. The commissure post includes a first hole near an inflow end of the commissure post and a second hold near an outflow end of the commissure post. The transcatheter aortic valve prosthesis also includes a valve component including two or more valve leaflets disposed within the frame. A commissure is formed where two valve leaflets of the two or more valve leaflets are attached to each other and each commissure is secured to a commissure post of the plurality of commissure posts of the frame. A suture attaches one of the commissures to one of the commissure posts. The suture creates a suture pattern including a plurality of "X" suture patterns and a plurality of inverted "V" suture patterns in an alternating manner.

In an aspect of the sixth embodiment, and in combination with any other aspects herein, the disclosure provides that the suture pattern further includes a first locking knot positioned on a first side of the commissure post, adjacent to the outflow end thereof, and a second locking knot is positioned on a second side of the commissure post, adjacent to the outflow end thereof and opposing the first locking knot.

In an aspect of the sixth embodiment, and in combination with any other aspects herein, the disclosure provides that the suture pattern further includes a third locking knot positioned distal to the inflow end of the commissure post.

In an aspect of the sixth embodiment, and in combination with any other aspects herein, the disclosure provides that each inverted "V" suture pattern is disposed at a hole of the commissure post and each "X" suture pattern is disposed above, below, or in between the holes of the commissure post.

In an aspect of the sixth embodiment, and in combination with any other aspects herein, the disclosure provides that the suture pattern includes exactly three "X" suture patterns and exactly two inverted "V" suture patterns.

According to a seventh embodiment hereof, the present disclosure provides a method of attaching a commissure to a commissure post of a transcatheter aortic valve prosthesis. A suture is advanced around a full perimeter of an inflow end of a commissure post of a transcatheter aortic valve prosthesis such that the suture approaches the commissure post from a left side. The transcatheter aortic valve prosthesis includes a frame having a plurality of struts, a plurality of first cells, a plurality of commissure posts, and a valve component including two or more valve leaflets disposed within the frame. Each commissure post includes a first hole near an inflow end of the commissure post and a second hole near an outflow end of the commissure post. The suture is positioned through the first hole and back around the full perimeter of the commissure post at a longitudinal position between the first hole and the second hole. The suture is advanced through the second hole and back around the full perimeter of the commissure post at a longitudinal position above the second hole. The suture is advanced around the full perimeter of the outflow end of the commissure post above the second hole, forming a "X" suture pattern at a longitudinal position above the second hole. The suture is positioned through the second hole, forming an inverted "V" suture pattern at the second hole. The suture is advanced around the full perimeter of the commissure post at the longitudinal position between the first hole and the second hole, forming the "X" suture pattern at the longitudinal position between the first hole and the second hole. The suture is positioned through the first hole, forming the inverted "V" suture pattern at the first hole. The suture is advanced around the full perimeter of the commissure post at the inflow end of the commissure post, forming the "X" suture pattern below the first hole. The inverted "V" suture pattern is disposed between a pair of adjacent "X" suture patterns in an alternating manner.

In an aspect of the seventh embodiment, and in combination with any other aspects herein, the disclosure provides that the method further includes the step of tying a first locking knot positioned on a first side of the commissure post, adjacent to the outflow end thereof, and a second locking knot positioned on a second side of the commissure post, adjacent to the outflow end thereof and opposing the first locking knot.

In an aspect of the seventh embodiment, and in combination with any other aspects herein, the disclosure provides that the step of tying a third locking knot positioned distal to the inflow end of the commissure post.

In an aspect of the seventh embodiment, and in combination with any other aspects herein, the disclosure provides that each inverted "V" suture pattern is disposed at a hold of the commissure post and each "X" suture pattern is disposed above, below, or in between the holes of the commissure post.

In an aspect of the seventh embodiment, and in combination with any other aspects herein, the disclosure provides that the suture pattern includes exactly three "X" suture patterns and exactly two inverted "V" suture patterns.

According to an eighth embodiment hereof, the present disclosure provides a transcatheter aortic valve prosthesis for replacement of a native heart valve. The transcatheter aortic valve prosthesis includes a frame having a plurality of struts, a plurality of first cells, and a plurality of commissure posts, a valve component including two or more valve leaflets disposed within the frame. A commissure is formed where two valve leaflets of the two or more valve leaflets are attached to each other. Each commissure is secured to a commissure post of the plurality of commissure posts using a first suture. The first suture creates a first suture pattern. A tissue bumper covers the first suture. A second suture attaches the tissue bumper to the commissure post of the frame. The second suture creates a second suture pattern including a plurality of "X" suture patterns over an exterior surface of the tissue bumper.

In an aspect of the eighth embodiment, and in combination with any other aspects herein, the disclosure provides that the second suture pattern includes exactly three "X" suture patterns.

In an aspect of the eighth embodiment, and in combination with any other aspects herein, the disclosure provides that the second suture pattern further includes a pair of double square knots positioned distal to the inflow end of the commissure post.

In an aspect of the eighth embodiment, and in combination with any other aspects herein, the disclosure provides that the tissue bumper is circumferential.

In an aspect of the eighth embodiment, and in combination with any other aspects herein, the disclosure provides that the first suture pattern includes a plurality of "X" suture patterns and a plurality of inverted "V" suture patterns in an alternating manner.

In an aspect of the eighth embodiment, and in combination with any other aspects herein, the disclosure provides that each inverted "V" suture pattern is disposed at a hold of the commissure post and each "X" suture pattern is disposed above, below, or in between the holes of the commissure post.

In an aspect of the eighth embodiment, and in combination with any other aspects herein, the disclosure provides that the suture pattern includes exactly three "X" suture patterns and exactly two inverted "V" suture patterns.

According to a ninth embodiment hereof, the present disclosure provides a method of attaching a tissue bumper to a commissure post of a transcatheter aortic valve prosthesis. A pair of tissue portions are positioned underneath a commissure post of a transcatheter aortic valve prosthesis. The tissue portions extend in opposing directions. The transcatheter aortic valve prosthesis includes a frame having a plurality of struts, a plurality of first cells, a plurality of commissure posts, and a valve component including two or more valve leaflets disposed within the frame. The tissue portions are trimmed such that enough tissue is left to cover the commissure post when folding over. A suture is advanced through the tissue portion to the right of the commissure post near an inflow end of the commissure post. The tissue portions are folded over the commissure post. The suture is wrapped around the full perimeter of the tissue portions and the commissure post, beginning at the inflow end of the commissure post, until the suture is near an outflow end of the commissure post. The suture is wound back towards the inflow end of the commissure post around the full perimeter of the tissue portions and the commissure post, forming a first "X" suture pattern at a longitudinal position near the outflow end of the commissure post. The suture is wrapped around the full perimeter of the tissue portions and the commissure post back towards the inflow end of the commissure post, forming a second "X" suture pattern and a third "X" suture pattern. The third "X" suture pattern is disposed at a longitudinal position near the inflow end of the commissure post and the second "X" suture pattern is disposed between the first "X" suture pattern and the third "X" suture pattern.

In an aspect of the ninth embodiment, and in combination with any other aspects herein, the disclosure provides that the folded tissue portions define a circumferential tissue bumper once the folded tissue portions are secured to the commissure post.

In an aspect of the ninth embodiment, and in combination with any other aspects herein, the disclosure provides that the method further includes the step of tying a pair of double square knots positioned below the inflow end of the commissure post to secure the folded tissue portions to the commissure post.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings, which are incorporated herein and form a part of the specification.

FIG. 3E is a table showing exemplary values of the root widths, mid-widths, and lengths of the plurality of struts of the inflow end portion of FIG. 3D.

FIG. 3G is a table showing exemplary values of the root widths, mid-widths, and lengths of the plurality of struts of the outflow end portion of FIG. 3F.

FIG. 7B depicts a top view of the transcatheter aortic valve prosthesis of FIGS. 6A and 6B.

FIG. 7C depicts a perspective side view of a portion of the transcatheter aortic valve prosthesis of FIGS. 6A and 6B.

DETAILED DESCRIPTION

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a transcatheter aortic valve prosthesis. The following detailed description is merely exemplary in nature and is not intended to limit the invention of the application and uses of the invention. Furthermore, there is no intention to be bound by any expressed or implied theory presented in the preceding field of the invention, background, summary or the following detailed description.

Embodiments hereof are related to transcatheter aortic valve prostheses which are configured to improve access to a patient's coronary arteries if the patient requires a percutaneous coronary intervention (PCI) procedure post-implantation of the transcatheter aortic valve prosthesis and/or reduce conduction disturbances in order to mitigate permanent pacemaker implantation rates. More particularly, frames of the transcatheter aortic valve prostheses described herein include one or more enlarged cells, referred to herein as access cells, which are of sufficient size to be easily crossed with a coronary guide catheter into either the right coronary artery or the left main coronary artery once the transcatheter heart valve prosthesis is deployed in situ. Each enlarged access cell has an area that is relatively larger than a cell directly adjacent thereto, with has an area between approximately 12% and approximately 33% of the area of the enlarged access cell. In some embodiments, the frame of the transcatheter aortic valve prosthesis may further include a window or a conduction protection cell which is oriented to align with a portion of the conduction system of the heart to reduce conduction disturbances to the anatomy. In some embodiments, a commissure of a valve component is attached to a commissure post of the frame via a suture pattern including a plurality of "X" suture patterns and a plurality of inverted "V" suture patterns in an alternating manner. Further, in some embodiments, a second suture attaches a tissue bumper to the commissure post via a second suture pattern including a plurality of "X" suture patterns over an exterior surface of the tissue bumper.

Figure 1:
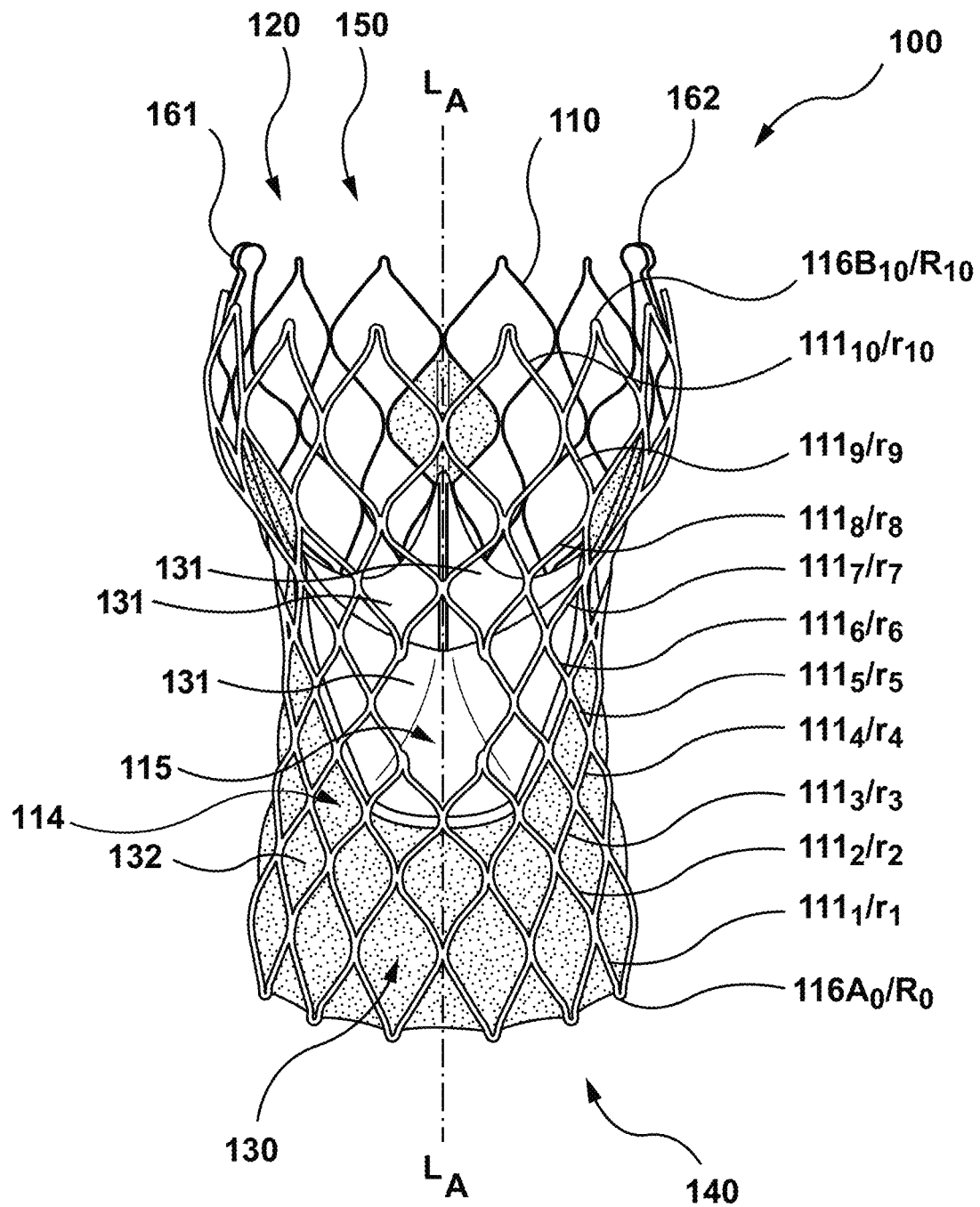
FIG. 1 depicts a perspective side view of a transcatheter aortic valve prosthesis according to embodiments hereof, wherein the transcatheter aortic valve prosthesis includes three access cells.

FIGS. 1, 2, 3A-3E, 4A-4F, and 5 depict an embodiment of a transcatheter aortic valve prosthesis 100 that includes a frame 110 having one or more access cells 115. As best shown in FIG. 1, the transcatheter aortic valve prosthesis 100 includes the frame 110 having an inflow end 140 and an outflow end 150, and a valve component 130 disposed within the frame 110. The frame 110 of the transcatheter aortic valve prosthesis 100 includes a plurality of struts 111 that are arranged to form a plurality of cells arranged circumferentially around a longitudinal axis $L_A$ of the transcatheter aortic valve prosthesis 100 and longitudinally to form a tubular structure. The struts 111 are defined herein as the elongated wire segments of the frame 110, as can be seen in FIG. 1. In other words, the struts 111 are elongated segments that extend between each crown 116 or node 117 of the frame 110, which is explained in more detail below. In the embodiment shown, the plurality of cells include a plurality of first cells 114 and one or more second or access cells 115. The one or more access cells 115 each have an enlarged area relative or compared to the first cells 114. The valve component 130 is disposed within a central lumen 120 of the frame 110, and the valve component 130 is attached to the frame 110. The frame 110 secures the transcatheter aortic valve prosthesis 100 in place in situ within the vasculature of the patient.

Figure 3B:
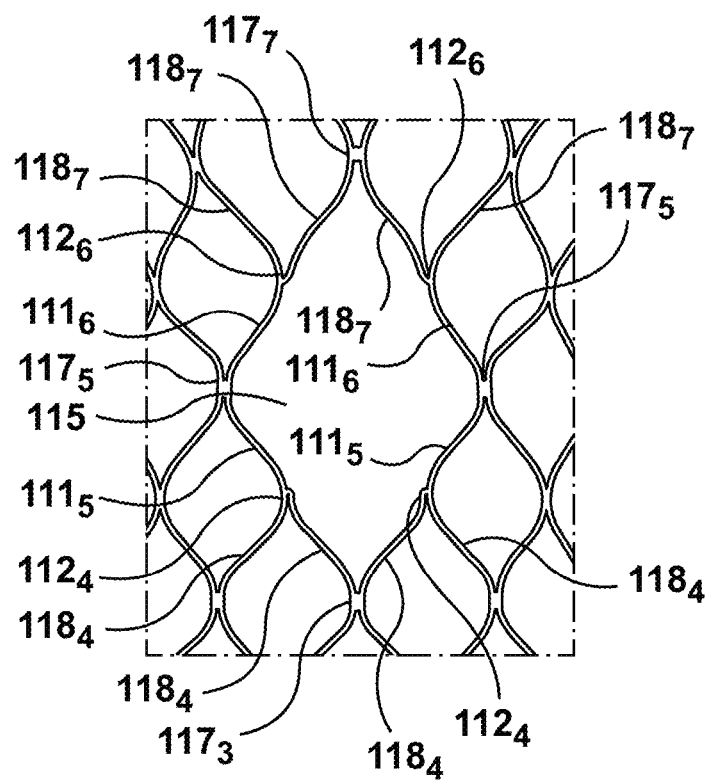
FIG. 3B depicts a close up view of an access cell of the frame of the transcatheter aortic valve prosthesis of FIG. 3A.
Figure 4A:
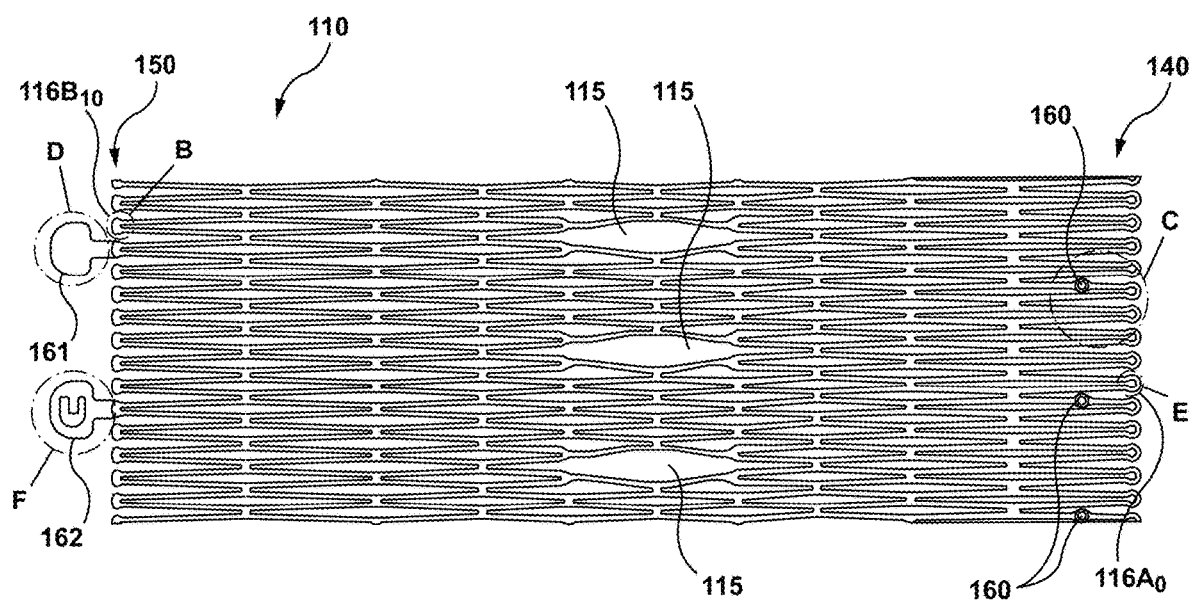
FIG. 4A depicts a flat, unexpanded configuration of the frame of the transcatheter aortic valve prosthesis of FIG. 1.

As can be seen in FIG. 1, the plurality of struts 111 are arranged at the inflow end 140 of the frame 110 such that two adjacent struts 111 of the plurality of struts 111 come together to form a crown 116 at the inflow end 140. Thus, a row or plurality of inflow crowns 116A are formed at the inflow end 140 of the frame 110. As best shown in FIG. 4A, in this embodiment, the frame 110 includes exactly fifteen inflow crowns 116A at the inflow end 140 of the frame 110, but this is not meant to be limiting. The inflow end 140 of the frame 110 also forms an inflow end of the transcatheter aortic valve prosthesis 100. The plurality of struts 111 are arranged at the outflow end 150 of the frame 110 such that two adjacent struts 111 of the plurality of struts 111 come together to form a crown 116 at the outflow end 150. Thus, as best shown in FIG. 4A, the frame 110 includes exactly fifteen outflow crowns 116B formed at the outflow end 150 of the frame 110, but this is not limiting. The outflow end 150 of the frame 110 also forms an outflow end of the transcatheter aortic valve prosthesis 100. As described in more detail below, exactly three struts 111 come together to form a tri-strut connection 112 and exactly four struts 111 come together to form a node 117. The tri-strut connections 112 are Y-shaped and the nodes 117 are X-shaped or H-shaped, as can be seen in FIG. 3B. The first cells 114 and the access cells 115 are defined as the open spaces or windows formed between the plurality of struts 111, tri-strut connections 112, crowns 116, and/or nodes 117.

The frame 110 is self-expanding and may be formed of stainless steel, nickel titanium alloys such as Nitinol™, cobalt chromium alloys such as MP35N, other alloys such as ELGILOY® (Elgin, Ill.), various polymers, pyrolytic carbon, silicone, polytetrafluoroethylene (PTFE), or any number of other materials or combination of materials. A suitable biocompatible material is selected such that the transcatheter aortic valve prosthesis 100 may be compressed into a reduced-diameter configuration for transcatheter delivery to a native valve, whereby release from a delivery system returns the transcatheter aortic valve prosthesis 100 to an expanded, deployed configuration. Alternatively, the transcatheter aortic valve prosthesis 100 may be balloon-expandable as would be understood by one of ordinary skill in the art.

Figure 3A:
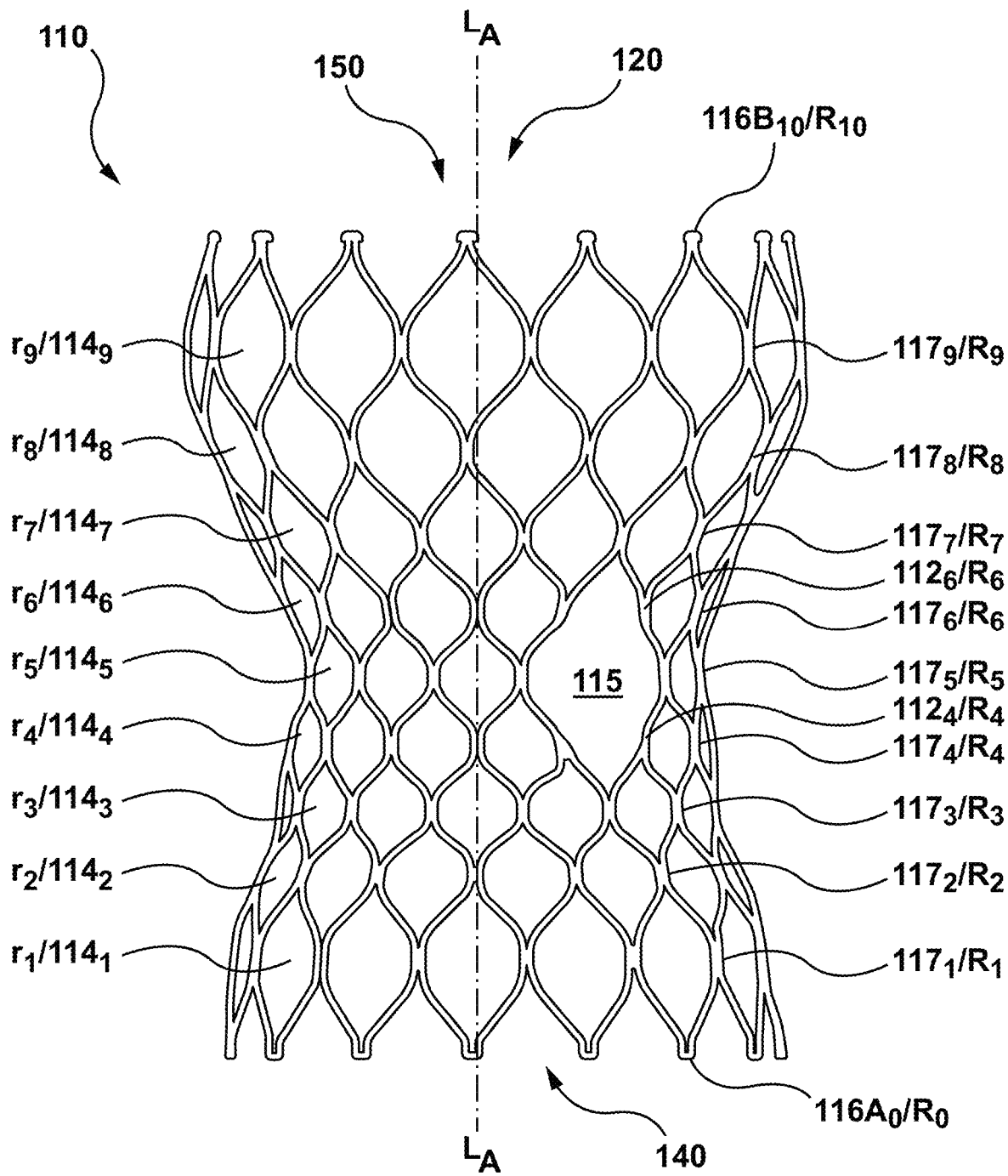
FIG. 3A depicts a side view of a frame of the transcatheter aortic valve prosthesis of FIG. 1.

The frame 110 of the transcatheter aortic valve prosthesis 100 includes the plurality of the first cells 114 arranged circumferentially around the longitudinal axis $L_A$ of the transcatheter aortic valve prosthesis 100 and longitudinally to form a tubular structure, as best shown in FIG. 3A. Each first cell 114 of the plurality of first cells 114 are formed by exactly four struts 111 and exactly four nodes 117, or exactly four struts 111 and exactly three nodes 117 and exactly one crown 116, and are generally diamond-shaped. In embodiments, the plurality of first cells 114 vary in size depending on the position of the first cell 114 within the frame 110, i.e., row placement and/or longitudinal position on the frame 110. For example, in some embodiments, the plurality of first cells 114 disposed near the inflow end 140 and the outflow end 150 of the frame 110 are larger than the plurality of first cells 114 disposed at a midline or midportion of the frame 110. In other embodiments, the plurality of first cells 114 disposed near the outflow end 150 of the frame 110 are larger than the plurality of first cells 114 disposed near the inflow end 140 of the frame 110. In the embodiments described herein, each access cell 115 is larger in size than each first cell 114 of the plurality of first cells 114.

Figure 3C:
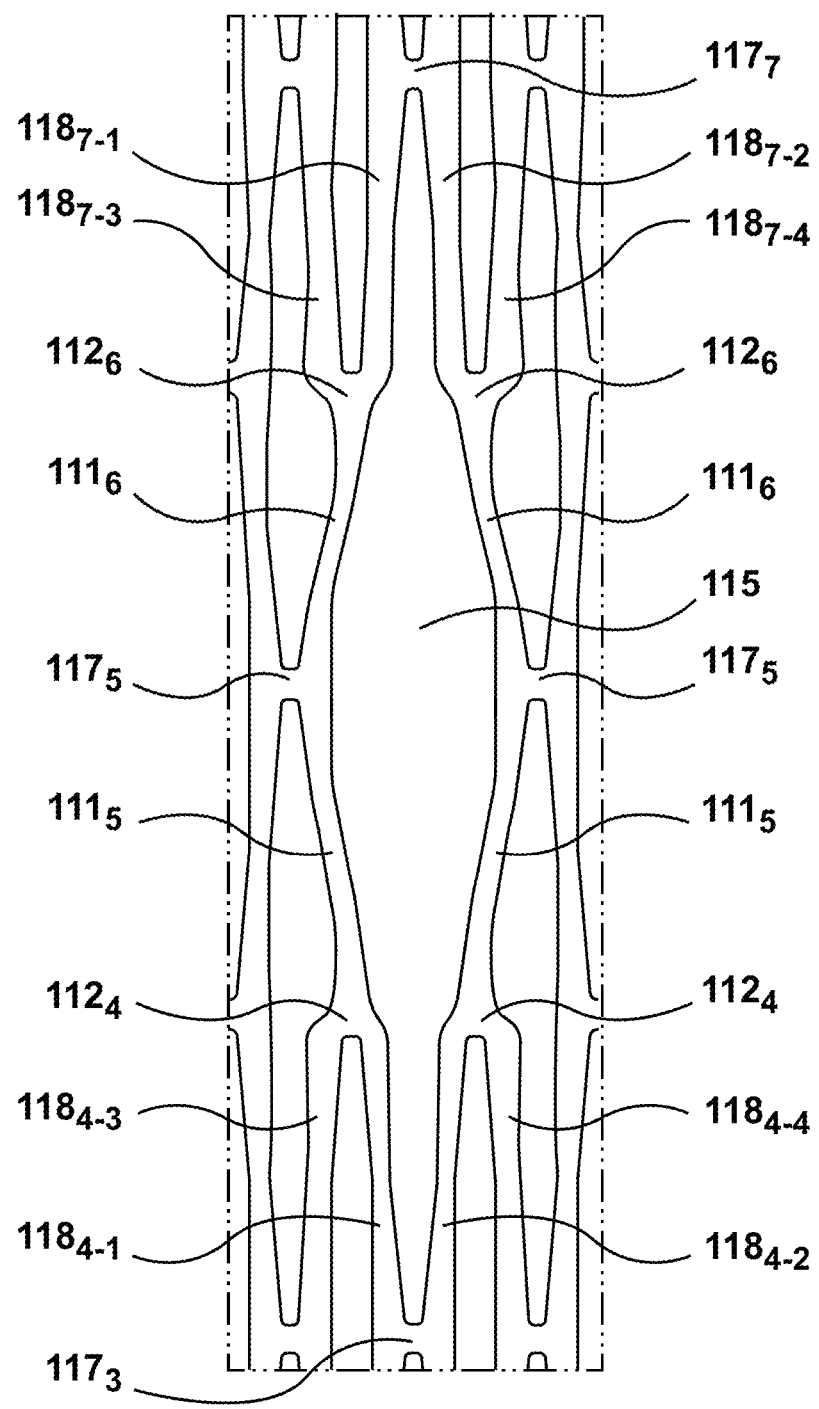
FIG. 3C depicts a flat, partially expanded configuration of the access cell of the frame of the transcatheter aortic valve prosthesis of FIG. 3A.
Figure 3D:
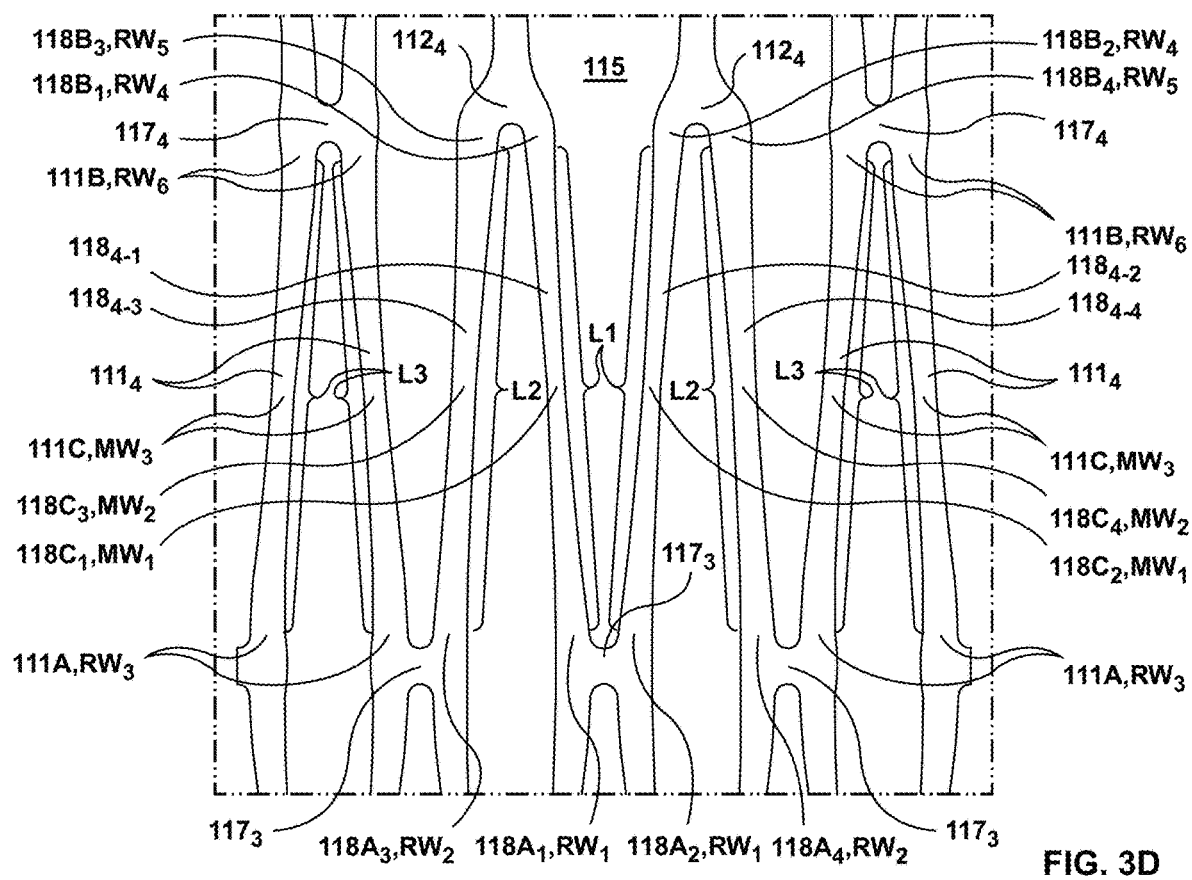
FIG. 3D depicts a close up view of an inflow end portion of the access cell of the frame of the transcatheter aortic valve prosthesis of FIG. 3A.
Figure 4B:
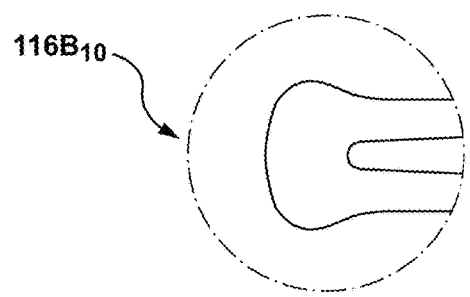
FIG. 4B depicts a close-up view of an outflow crown of the frame of the transcatheter aortic valve prosthesis of FIG. 1.
Figure 4C:
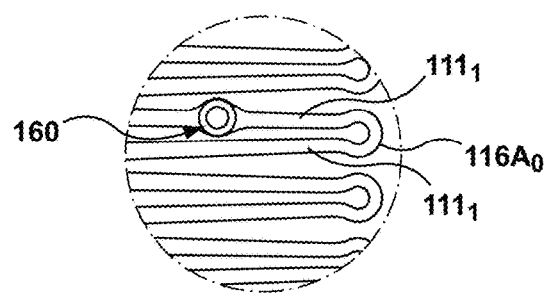
FIG. 4C depicts a close-up view of a marker of the frame of the transcatheter aortic valve prosthesis of FIG. 1.
Figure 4D:
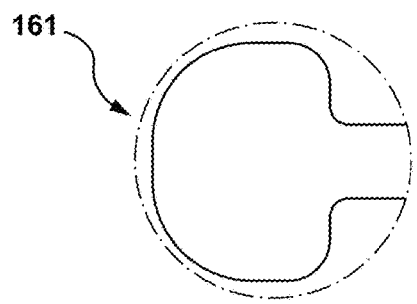
FIG. 4D depicts a close-up view of a first paddle of the frame of the transcatheter aortic valve prosthesis of FIG. 1.
Figure 4E:
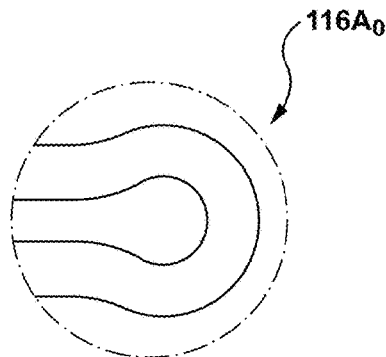
FIG. 4E depicts a close-up view of an inflow crown of the frame of the transcatheter aortic valve prosthesis of FIG. 1.

In FIGS. 1, 3A-3E and 4A-4F, subscripts have been added to the reference numerals for the crowns 116, nodes 117, tri-strut connections 112, struts 111, first cells 114 and access cells 115 to indicate the row number of each type of frame component starting with the inflow end 140. The frame 110 includes a total of eleven rows of crowns 116 and nodes 117, as best shown in FIG. 3A. In such an embodiment, beginning at the inflow end 140 of the frame 110, row $R_0$ describes the row of inflow crowns $116A_0$ at the inflow end 140 of the frame 110. FIG. 4E depicts a close-up view of an inflow crown 116A of the plurality of inflow crowns $116A_0$ in the row $R_0$ at the inflow end 140 of the transcatheter aortic valve prosthesis 100. Disposed directly adjacent to the row $R_0$ of inflow crowns $116A_0$ in row $R_1$ of nodes $117_1$, and directly adjacent the row $R_1$ of nodes $117_1$ is row $R_2$ of nodes $117_2$. This naming convention for the nodes 117 continues up to the outflow end 150 of the frame 110 to the row $R_9$ of nodes $117_9$. Disposed directly adjacent the row $R_9$ of nodes $117_9$ is row $R_{10}$ of outflow crowns $116B_{10}$ at the outflow end 150 of the frame 110. FIG. 4B depicts a close-up view of an outflow crown 116B of the plurality of outflow crowns $116B_{10}$ in the row $R_{10}$ at the outflow end 150 of the transcatheter aortic valve prosthesis 100.

In the embodiment shown, the frame 110 can include a total of nine rows of first cells 114 beginning at the inflow end 140 with the row $r_1$ of first cells $114_1$, to the row $r_9$ of first cells $114_9$ at the outflow end 150, as best shown in FIG. 1. For example, the row $r_1$ of first cells $114_1$ is disposed between the row $R_0$ of inflow crowns $116A_0$ and the row $R_2$ of nodes $117_2$. In particular, each first cell $114_1$ in the row $r_1$ is defined by an inflow crown $116A_0$ in the row $R_0$, two struts $111_1$ in the row $r_1$, two nodes $117_1$ in the row $R_1$, two struts $111_2$ in the row $r_2$, and one node $117_2$ in the row $R_2$. The row $r_2$ of first cells $114_2$ is disposed between the row $R_1$ of nodes $117_1$ and the row $R_3$ of nodes $117_3$, and the first cells 114 thereof are defined the same as described above with respect to the row $114_1$ of first cells 114. The naming convention for the first cells 114 continues to the row $r_9$ of first cells $114_9$ located at the outflow end 150 between the row $R_8$ of nodes $117_8$ and the row $R_{10}$ of outflow crowns $116B_{10}$.

The struts 111 are also numbered in rows beginning at the inflow end 140 of the frame 110, as shown in FIG. 1. For example, the struts 111 that come together to form the inflow crowns 116A in the row $R_0$ at the inflow end 140 are denoted as row $r_1$ of struts $111_1$. The struts 111 in between the row $R_1$ of nodes $117_1$ and the row $R_2$ of nodes $117_2$ are denoted as row $r_2$ of struts $111_2$. This naming convention for the struts 111 continues distally to the outflow end 150 of the frame 110 to the row $r_{10}$ of struts $111_{10}$.

The access cells 115 are enlarged cells (relative to the first cells 114) which are configured to improve access to a patient's percutaneous coronary arteries if a percutaneous coronary intervention procedure is required post-implantation of transcatheter aortic valve prosthesis 100. In this embodiment, as shown best in FIG. 3A when the frame 110 is in an expanded configuration, the area of the at least one access cell 115 is approximately equivalent to the area of four first cells 114 combined, specifically the first cells 114 disposed directly adjacent to at least one of the access cells 115. Stated another way, the area of an access cell 115 compared to the area of a first cell 114 directly adjacent to at least one of the access cells 115 is approximately a 4:1 ratio. In this embodiment, a first cell 114 adjacent to at least one of the access cells 115 has an area that is approximately 25% of an area of one of the access cells 115 of the frame 110, with "approximately" including a tolerance of 5%. In another embodiment, a first cell 114 adjacent to at least one of the access cells 115 has an area that is between 20% and 25% of an area of one of the access cells 115 of the frame 110. The size of the access cell 115 and the size of the first cell 114 directly adjacent thereto depends on the overall size of the transcatheter aortic valve prosthesis 100. For example, transcatheter aortic valve prostheses typically are manufactured in several sizes, such as 23 mm, 26 mm, 29 mm and/or 34 mm. Depending on the size of the transcatheter aortic valve prosthesis 100, the area of the access cell 115 can range from between 70-115 mm² and the area of the first cell 114 can range between 14-26 mm².

Figure 2:
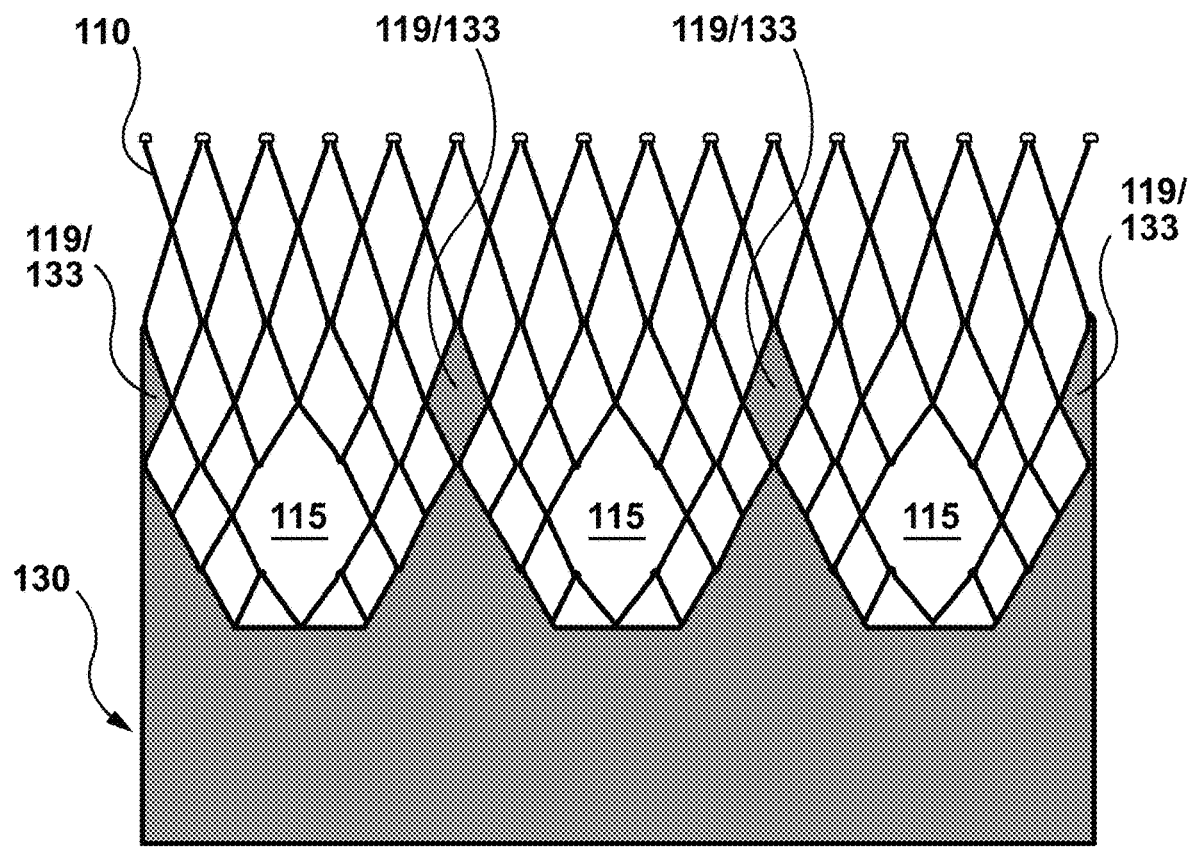
FIG. 2 depicts a flat, expanded configuration of the transcatheter aortic valve prosthesis of FIG. 1.

In the embodiment shown, the frame 110 of the transcatheter aortic valve prosthesis 100 includes exactly three access cells 115, as shown in the flat, expanded configuration of the prosthesis 100 in FIG. 2. The three access cells 115 are disposed between the row $r_3$ of first cells $114_3$ and the row $r_7$ of first cells $114_7$ of the frame 110. Each of the three access cells 115 are centered in a circumferential direction between two commissure cells 119, located in the row $r_7$ of first cells $114_7$, as shown in FIG. 2. The frame 110 includes exactly three commissure cells 119. The three commissure cells 119 are first cells $114_7$ of the row $r_7$ that have the leaflet commissures attached thereto, as described in more detail below. In other words, each of the three access cells 115 are equally spaced around the longitudinal axis $L_A$ of the transcatheter aortic valve prosthesis 100 and laterally from the adjacent two commissure cells 119. A close-up view of one of the access cells 115 can be seen in FIG. 3B. The access cell 115 shown in FIG. 3B, as well as the two other access cells 115 not shown, are each enclosed by one node $117_3$ in the row $R_3$, two optimized struts $118_4$ in the row $r_4$ (described in further detail below), two tri-strut connections $112_4$ in the row $R_4$, two standard struts $111_5$ in the row $r_5$, two nodes $117_5$ in the row $R_5$, two standard struts $1118_6$ in the row $r_6$, two tri-strut connections $112_6$ in the row $R_6$, two optimized struts $118_7$ in the row $r_7$ (described in further detail below), and one node $117_7$ in the row $R_7$.

Due to the relatively larger size of the access cells 115, relative to the first cells 114 adjacent thereto, some of the struts adjacent to the access cells 115 are modified to reduce crimp strains while maintaining the maximized the window area and also maintaining the radial stiffness of the margin of attachment in which the valve component 130 is attached to the frame 110. As will be described herein, two rows of the plurality of struts each include a plurality of standard struts and a plurality of optimized struts. Each standard strut of the plurality of standard struts has a first width profile and a first length, and each optimized strut of the plurality of optimized struts has a width profile that is different from the first width profile and a length that is different from the first length. The term "optimized strut" is used herein to describe a strut that is altered, or configured, for a specific purpose as compared to a "standard strut" of the frame 110 which is not altered or configured for this purpose. In the embodiment of FIGS. 1-5, the optimized struts described herein are altered or configured to reduce crimp strains around the access cells 115, while the remaining struts of the frame 110 are standard struts which are not altered or configured for this purpose. The width profile and length of the optimized struts, relative to the standard struts, will be described in more detail below.

The row of the plurality of struts which includes the plurality of optimized struts is disposed at an inflow end or an outflow end of the access cells 115. In this embodiment, a first row of the plurality of struts which includes optimized struts is disposed at the inflow end of the access cells 115 and a second row of the plurality of struts which includes optimized struts is disposed at the outflow end of the access cells 115. Within each of the first and second rows, for each of the access cells 115, the plurality of optimized struts include a first optimized strut, a second optimized strut, a third optimized strut, and a fourth optimized strut, with the first optimized strut and the second optimized strut enclosing or defining the inflow end of each access cell 115, and the third optimized strut being disposed directly adjacent to the first optimized strut and the fourth optimized strut being disposed directly adjacent to the second optimized strut.

Figure 3F:
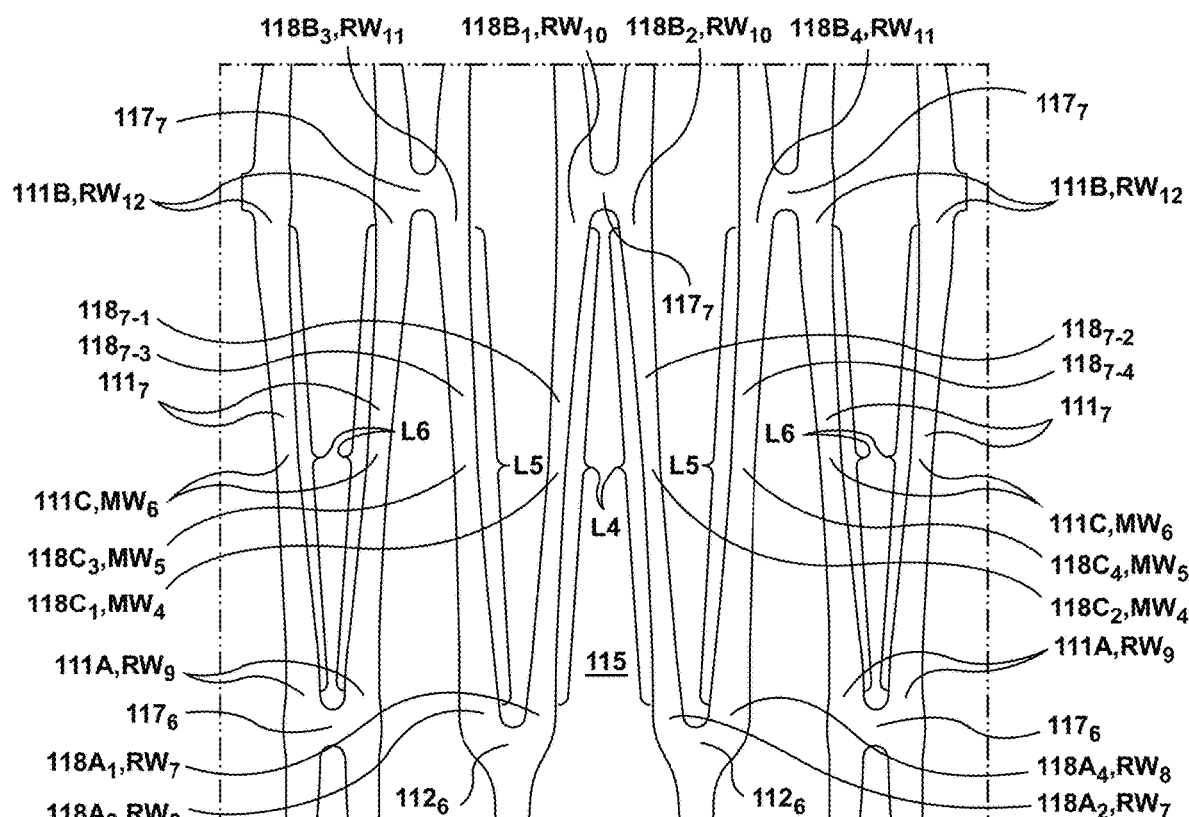
FIG. 3F depicts a close up view of an outflow end portion of the access cell of the frame of the transcatheter aortic valve prosthesis of FIG. 3A.

More particularly, in the embodiment shown, the crimp strain of the frame 110 where each of the access cells 115 is located, from row $R_3$ of nodes $117_3$ to row $R_7$ of nodes $117_7$, is reduced by modifying a first optimized strut $118_{4-1}$ in the row $r_4$, a second optimized strut $118_{4-2}$ in the row $r_4$, a third optimized strut $118_{4-3}$ in the row $r_4$, and a fourth optimized strut $118_{4-4}$ in the row $r_4$. The first optimized strut $118_{4-1}$ and the second optimized strut $118_{4-2}$ form, define, or enclose an inflow-most end of the access cell 115. The third optimized strut $118_{4-3}$ is disposed directly adjacent to the first optimized strut $118_{4-1}$, and the fourth optimized strut $118_{4-4}$ is disposed directly adjacent to the second optimized strut $118_{4-2}$, as shown in FIGS. 3C-3D. The crimp strain of the frame 110 where each of the access cells 115 are located is further reduced by modifying a first optimized strut $118_{7-1}$ in the row $r_7$, a second optimized strut $118_{7-2}$ in the row $r_7$, a third optimized strut $118_{7-3}$ in the row $r_7$, and a fourth optimized strut $118_{7-4}$ in the row $r_7$. The first optimized strut $118_{7-1}$ and the second optimized strut $118_{7-2}$ form, define, or enclose an outflow-most end of the access cell 115. The third optimized strut $118_{7-3}$ in the row $r_7$ is disposed directly adjacent to the first optimized strut $118_{7-1}$, and the fourth optimized strut $118_{7-4}$ in the row $r_7$ is disposed directly adjacent to the second optimized strut $118_{7-2}$, as shown in FIGS. 3C and 3F. The standard struts $111_5$ and $111_6$ in the rows $r_5$ and $r_6$ that define or enclose a portion of the access cell 115, as best shown in FIGS. 3B-3C, are not modified for the purpose of reducing crimp strains around the access cells 115. As will be shown and described in more detail with respect to FIG. 3D and FIG. 3F, each of the optimized struts 118 of the frame 110 has a width profile and a length that differs from the width profile and length of each standard strut 111 in the same row of the frame 110. In other words, the length and width dimensions of each optimized strut 118 are modified relative to the length and width dimensions of the standard struts 111 within the same row of the frame 110. The length and width dimensions of the standard struts 111 within the same row of the frame are the same for each standard strut but the length and width dimensions of the optimized struts 111 within the same row of the frame are not necessarily the same for each optimized strut.

A close up view of the four adjacent optimized struts $118_4$ and four standard struts $111_4$ in the row $r_4$ are shown in FIG. 3D. Each optimized strut 118 includes an inflow end root 118A, an outflow end root 118B, and a middle portion 118C disposed between the inflow end root 118A and the outflow end root 118B. Each standard strut 111 includes an inflow end root 111A, an outflow end root 111B, and a middle portion 111C disposed between the inflow end root 111A and the outflow end root 111B.

As best shown in FIG. 3D, the first optimized strut $118_{4-1}$ in the row $r_4$ includes a first inflow end root 118A1, a first outflow end root 118B1, and a first middle portion 118C1. The second optimized strut $118_{4-2}$ in the row $r_4$ includes a second inflow end root 118A2, a second outflow end root 118B2, and a second middle portion 118C2. The third optimized strut $118_{4-3}$ in the row $r_4$ includes a third inflow end root 118A3, a third outflow end root 118B3, and a third middle portion 118C3. The fourth optimized strut $118_{4-4}$ in the row $r_4$ includes a fourth inflow end root 118A4, a fourth outflow end root 118B4, and a fourth middle portion 118C4. As can be seen in FIG. 3D, the first inflow end root 118A1 of the first optimized strut $118_{4-1}$ and the second inflow end root 118A2 of the second optimized strut $118_{4-2}$ in the row $r_4$ that enclose, or form, the inflow-most end of the access cell 115 meet at a node $117_3$ in the row $R_3$. The first outflow end root 118B1 of the first optimized strut $118_{4-1}$ meets with the third outflow end root 118B3 of the third optimized strut $118_{4-3}$ at a Y-shaped tri-strut connection $112_4$ in the row $R_4$ while the second outflow end root 118B2 of the second optimized strut $118_{4-2}$ meets with the fourth outflow end root 118B4 of the fourth optimized strut $118_{4-4}$ at a Y-shaped tri strut connection $112_4$ in the row $R_4$. The first optimized strut $118_{4-1}$ and the second optimized strut $118_{4-2}$ in the row $r_4$ that form the inflow-most end of the access cell 115 have a root width RW1 at the first and second inflow end roots 118A1 and 118A2, a root width RW4 at the first and second outflow end roots 118B1 and 118B2, a mid-width MW1 at the first and second middle portions 118C1 and 118C2, and a strut length L1 that extends from the inflow end roots 118A1, 118A2 to the outflow end roots 118B1, 118B2, respectively.

The third inflow end root 118A3 of the third optimized strut $118_{4-3}$ meets with an inflow end root 111A of a standard strut $111_4$ in the row $r_4$ at a node $117_3$ in the row $R_3$ and the third outflow end root 118B3 of the third optimized strut $118_{4-3}$ meets with the first outflow end root 118A1 of the first optimized strut $118_{4-1}$ at a Y-shaped tri-strut connection $112_4$ in the row $R_4$. The fourth inflow end root 118A4 of the fourth optimized strut $118_{4-4}$ meets with an inflow end root 111A of a standard strut $111_4$ in the row $r_4$ at a node $117_3$ in the row $R_3$ and the fourth outflow end root 118B4 of the fourth optimized strut $118_{4-4}$ meets with the second outflow end root 118B2 of the second optimized strut $118_{4-2}$ at a Y-shaped tri-strut connection $112_4$ in the row $R_4$. The third optimized strut $118_{4-3}$ and the fourth optimized strut $118_{4-4}$ in the row $r_4$ have a root width RW2 at the third and fourth inflow end roots 118A3 and 118A4, a root width RW5 at the third and fourth outflow end roots 118B3 and 118B4, a mid-width MW2 at the first and second middle portions 118C3 and 118C4, and a strut length L2 that extends from the inflow end roots 118A3,118A4 to the outflow end roots 118B3,118B4, respectively.

Four standard struts $111_4$ in the row $r_4$ are shown in FIG. 3D for reference and comparison to the optimized struts $118_4$ in the row $r_4$. Two pairs of adjacent standard struts $111_4$ meet at their outflow end roots 111B at nodes $117_4$ in the row $R_4$. The four standard struts $111_4$ in the row $r_4$ have a root width RW3 at the inflow end roots 111A, a root width RW6 at the outflow end roots 111B, a mid-width MW3 at the middle portions 111C, and a strut length L3 that extends from the inflow end roots 111A to the outflow end roots 111B of each standard strut $111_4$ in the row $r_4$. Depending on the size of the transcatheter aortic valve prosthesis 100, the values of these measurements may vary, as shown in FIG. 3E. All of the values shown in the table of FIG. 3E are measured in millimeters (mm). The size of the transcatheter aortic valve prosthesis 100 can range from 23-34 mm. FIG. 3E depicts the various root widths, mid-widths, and lengths of the standard struts $111_4$ and the optimized struts $118_4$ in the row $r_4$ as the size of the transcatheter aortic valve prosthesis 100 varies. FIG. 3E also depicts the width taper percentage for each of the standard struts $111_4$ and the optimized struts $118_4$ in the row $r_4$ and the length change percentage between the optimized struts $118_4$ and the standard struts $111_4$ in the row $r_4$.

A close up view of the four adjacent optimized struts $118_7$ and four standard struts $111_7$ in the row $r_7$ are shown in FIG. 3F. Each optimized strut 118 includes an inflow end root 118A, an outflow end root 118B, and a middle portion 118C disposed between the inflow end root 118A and the outflow end root 118B. Each standard strut 111 includes an inflow end root 111A, an outflow end root 111B, and a middle portion 111C disposed between the inflow end root 111A and the outflow end root 111B.

As best shown in FIG. 3F, the first optimized strut $118_{7-1}$ in the row $r_7$ includes a first inflow end root 118A1, a first outflow end root 118B1, and a first middle portion 118C1. The second optimized strut $118_{7-2}$ in the row $r_7$ includes a second inflow end root 118A2, a second outflow end root 118B2, and a second middle portion 118C2. The third optimized strut $118_{7-3}$ in the row $r_7$ includes a third inflow end root 118A3, a third outflow end root 118B3, and a third middle portion 118C3. The fourth optimized strut $118_{7-4}$ in the row $r_7$ includes a fourth inflow end root 118A4, a fourth outflow end root 118B4, and a fourth middle portion 118C4. As can be seen in FIG. 3F, the first outflow end root 118B1 of the first optimized strut $118_{7-1}$ and the second outflow end root 118B2 of the second optimized strut $118_{7-2}$ in the row $r_4$ that enclose, or form, the outflow-most end of the access cell 115 meet at a node $117_7$ in the row $R_7$. The first inflow end root 118A1 of the first optimized strut $118_{7-1}$ meets with the third inflow end root 118A3 of the third optimized strut $118_{7-3}$ at a Y-shaped tri-strut connection $112_6$ in the row $R_6$ while the second inflow end root 118A2 of the second optimized strut $118_{7-2}$ meets with the fourth inflow end root 118A4 of the fourth optimized strut $118_{7-4}$ at a Y-shaped tri-strut connection $112_6$ in the row $R_6$. The first optimized strut $118_{7-1}$ and the second optimized strut $118_{7-2}$ in the row $r_7$ that form the outflow-most end of the access cell 115 have a root width RW7 at the first and second inflow end roots 118A1 and 118A2, a root width RW10 at the first and second outflow end roots 118B1 and 118B2, a mid-width MW4 at the first and second middle portions 118C1 and 118C2, and a strut length L4 that extends from the inflow end roots 118A1,118A2 to the outflow end roots 118B1,118B2, respectively.

The third outflow end root 118B3 of the third optimized strut $118_{7-3}$ meets with an outflow end root 111B of a standard strut $111_7$ in the row $r_7$ at a node $117_7$ in the row $R_7$ and the third inflow end root 118A3 of the third optimized strut $118_{7-3}$ meets with the first inflow end root 118A1 of the first optimized strut $118_{7-1}$ at a Y-shaped tri-strut connection $112_6$ in the row $R_6$. The fourth outflow end root 118B4 of the fourth optimized strut $118_{7-4}$ meets with an outflow end root 111B of a standard strut $111_7$ in the row $r_7$ at a node $117_7$ in the row $R_7$ and the fourth inflow end root 118A4 of the fourth optimized strut $118_{7-4}$ meets with the second inflow end root 118A2 of the second optimized strut $118_{7-2}$ at a Y-shaped tri-strut connection $112_6$ in the row $R_6$. The third optimized strut $118_{7-3}$ and the fourth optimized strut $118_{7-4}$ in the row $r_7$ have a root width RW8 at the third and fourth inflow end roots 118A3 and 118A4, a root width RW11 at the third and fourth outflow end roots 118B3 and 118B4, a mid-width MW5 at the first and second middle portions 118C3 and 118C4, and a strut length L5 that extends from the inflow end roots 118A3,118A4 to the outflow end roots 118B3,118B4, respectively.

Four standard struts $111_7$ in the row $r_7$ are shown in FIG. 3F for reference and comparison to the optimized struts $118_7$ in the row $r_7$. Two pairs of adjacent standard struts $111_7$ meet at their inflow end roots 111A at nodes $117_6$ in the row $R_6$. The four standard struts $111_7$ in the row $r_7$ have a root width RW9 at the inflow end roots 111A, a root width RW12 at the outflow end roots 111B, a mid-width MW6 at the middle portions 111C, and a strut length L6 that extends from the inflow end roots 111A to the outflow end roots 111B. Depending on the size of the transcatheter aortic valve prosthesis 100, the values of these measurements may vary, as shown in FIG. 3G. All of the values shown in the table of FIG. 3G are measured in millimeters (mm). The size of the transcatheter aortic valve prosthesis 100 can range from 23-34 mm. FIG. 3G depicts the various root widths, mid-widths, and lengths of the standard struts $111_7$ and the optimized struts $118_7$ in the row $r_7$ as the size of the transcatheter aortic valve prosthesis 100 varies. FIG. 3G also depicts the width taper percentage for each of the standard struts $111_7$ and the optimized struts $118_7$ in the row $r_7$ and the length change percentage between the optimized struts $118_7$ and the standard struts $111_7$ in the row $r_7$.

In the embodiments shown, the plurality of struts of the frame 110, including both standard struts 111 and optimized struts 118, have the same thickness and the thickness is uniform. The uniform thickness of the plurality of struts may be between 0.45-0.48 mm. In an alternative embodiment (not shown), the struts 111 that enclose the access cells 115 of the frame 110 are not optimized or modified relative to the standard struts and have the same width and/or length as the rest of the struts 111 of the frame 110.

Figure 4F:
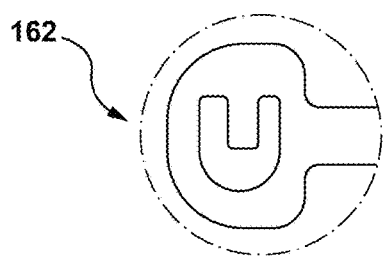
FIG. 4F depicts a close-up view of a second paddle of the frame of the transcatheter aortic valve prosthesis of FIG. 1.

In embodiments, one or more paddles are each attached to an outflow crown $116B_{10}$ in the row $R_{10}$ on the frame 110 as shown in FIG. 1. The paddles function to removably couple the transcatheter aortic valve prosthesis 100 to a delivery system (not shown). While FIG. 1 depicts a first paddle 161 and a second paddle 162, one skilled in the art will realize that more or fewer paddles can be utilized, and those paddles can be replaced with other components such as eyelets, loops, slots, or any other suitable coupling member. A close-up view of a first paddle 161 is shown in FIG. 4D. In embodiments, the paddles can be radiopaque so as to be visible under fluoroscopy. In other embodiments, the second paddle 162 may include a C-shaped marker to assist with orienting the transcatheter aortic valve prosthesis 100 during implantation, as shown in FIG. 4F. Those skilled in the art would recognize that other shapes may be utilized to determine the orientation of the transcatheter aortic valve prosthesis 100 during implantation.

The valve component 130 is disposed inside and coupled to an interior surface of the frame 110 of the transcatheter aortic valve prosthesis 100, as shown in FIG. 1, and includes three valve leaflets 131 and a skirt 132. In the embodiment shown, the three valve leaflets 131 are securely attached along their bases to the skirt 132 at a margin of attachment. Adjoining pairs of valve leaflets 131 are attached to one another at their lateral ends to form leaflet commissures 133. Alternatively, the transcatheter aortic valve prosthesis 100 may include one valve leaflet 131 or two leaflets 131. The valve component 130 is configured to block flow in one direction to regulate flow therethrough via the valve leaflets 131 that form a replacement bicuspid or tricuspid valve. The valve component 130 can be coupled to the interior surface of the frame 110 through any suitable manner known in the art, such as sewing the valve component 130 to the frame 110 using sutures. The valve component 130 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

In embodiments, the exactly three valve leaflets 131 are attached to one another, as well as the frame 110, at three commissure cells 119 in the row $114_7$ via sutures, as shown best in FIG. 2. Each commissure cell 119 includes a material pad that spans or bridges the commissure cell. Each material pad forms a base or support to which a respective commissure of the three leaflets 131 of the prosthetic valve is attached. Thus, the three commissure cells 119 are aligned with and attached to a respective commissure of the three leaflets 131 of the valve component 130. Each material pad may be generally diamond in shape. The material pad may be formed from a material such as those suitable for the skirt 132, such as but not limited to natural pericardial material such as tissue from bovine, equine or porcine origins, or synthetic materials such as polytetrafluoroethylene (PTFE), DACRON® polyester, pyrolytic carbon, or other biocompatible materials.

The skirt 132 of the valve component 130 is attached to the interior surface of the frame 110 through any suitable manner known in the art, such as sewing the skirt 132 to the frame 110 using sutures. As best shown in FIG. 1 and FIG. 2, the skirt 132 lines the interior surface of the frame 110 such that the first cells 114 disposed near the inflow end 140 of the frame 110 are covered by the skirt 132. In embodiments, the skirt 132 may cover approximately one-third of the interior surface of the frame 110 beginning at the inflow end 140. The skirt 132 directs blood flow through the central lumen 120 of the transcatheter aortic valve prosthesis 100 and to the valve leaflets 131 of the valve component 130. The skirt 132 may be formed of various flexible materials including but not limited to, natural pericardial material such as tissue from bovine, equine or porcine origins, or synthetic materials such as polytetrafluoroethylene (PTFE), DACRON® polyester, pyrolytic carbon, or other biocompatible materials.

The frame 110 of the transcatheter aortic valve prosthesis 100 contains one or more radiopaque markers 160 attached to, positioned in, and/or formed in the struts $111_1$ in the row $r_1$ at the inflow end 140 of the frame 110, as shown in FIG. 4A and FIG. 4C. The radiopaque markers 160 can be seen using fluoroscopy during implantation and aid in the positioning of the transcatheter aortic valve prosthesis 100 within the vasculature of the patient. The radiopaque markers 160 are utilized during longitudinal positioning of the transcatheter aortic valve prosthesis 100 in situ such that the depth of the transcatheter aortic valve prosthesis 100 relative to the native valve is as desired. In addition, the radiopaque markers 160 are also utilized during rotational or circumferential positioning of the transcatheter aortic valve prosthesis 100 within the native valve. More particularly, the radiopaque markers 160 are circumferentially aligned with the commissure cells 119 of the frame 110 and thus are also circumferentially aligned with the leaflet commissures of the valve component 130. When the radiopaque markers 160 are circumferentially aligned with the native valve commissures in situ, one or more of the access cells 115 should circumferentially align with the ostia of the coronary arteries. Stated another way, when the prosthetic commissures (i.e., the commissure cells 119 and leaflet commissures attached thereto) are circumferentially aligned with the native commissures of the native valve, the access windows 115 are also circumferentially aligned as desired. Further details relating to exemplary radiopaque marker patterns and methods of utilizing such radiopaque markers for circumferentially aligning the transcatheter aortic valve prosthesis 100 within the native valve may be found within U.S. patent App. No. TBD, which is assigned to the same assignee as the present invention. It will be understood by one of ordinary skill in the art that any other suitable method of circumferentially aligning the access windows 115 with the ostia of the coronary arteries may be utilized. Further, although not described for each embodiment herein, it will be understood by one of ordinary skill in the art that any frame described herein may include one or more radiopaque markers such as the radiopaque markers 160 for depth positioning of the respective transcatheter aortic valve prosthesis and/or circumferential alignment of the access cells thereof.

Figure 5:
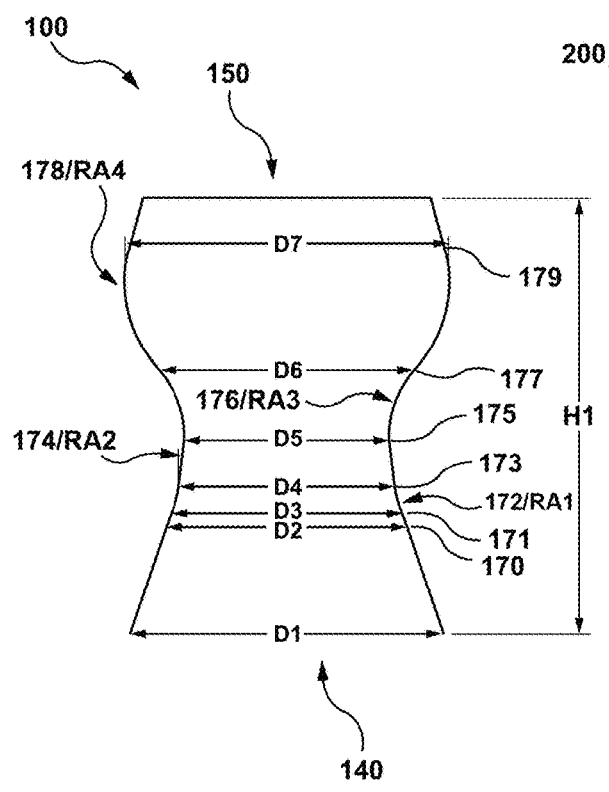
FIG. 5 depicts an outline of the transcatheter aortic valve prosthesis of FIG. 1.

FIG. 5 depicts an outline of the transcatheter aortic valve prosthesis 100 with horizontal lines and points denoting where various measurements have been recorded, however this is not meant to be limiting. For example, the diameter D1 of the transcatheter aortic valve prosthesis 100 at the horizontal line denoting the inflow end 140 is 35-36 mm. The transcatheter aortic valve prosthesis 100 has a diameter D2 of 27-28 mm at horizontal line 170, disposed 12-13 mm distally from the inflow end 140 of the transcatheter aortic valve prosthesis 100. The transcatheter aortic valve prosthesis 100 has a diameter D3 of 26-27 mm at horizontal line 171, disposed 13-14 mm distally from the inflow end 140 of the transcatheter aortic valve prosthesis 100. The transcatheter aortic valve prosthesis 100 has a radius RA1 of 18-19 mm at point 172. The transcatheter aortic valve prosthesis 100 has a diameter D4 of 24-25 mm at horizontal line 173, disposed 16-17 mm distally from the inflow end 140 of the transcatheter aortic valve prosthesis 100. The transcatheter aortic valve prosthesis 100 has a radius RA2 of 11-12 mm at point 174. The transcatheter aortic valve prosthesis 100 has a diameter D5 of 23-24 mm at horizontal line 175, disposed 22-23 mm distally from the inflow end 140 of the transcatheter aortic valve prosthesis 100. The transcatheter aortic valve prosthesis 100 has a radius RA3 of 9-10 mm at point 176. The transcatheter aortic valve prosthesis 100 has a diameter D6 of 29-30 mm at horizontal line 177, disposed 30-31 mm distally from the inflow end 140 of the transcatheter aortic valve prosthesis 100. The transcatheter aortic valve prosthesis 100 has a radius RA4 of 13-14 mm at point 178. The transcatheter aortic valve prosthesis 100 has a diameter D7 of 37-38 mm at horizontal line 179, disposed 44-45 mm distally from the inflow end 140 of the transcatheter aortic valve prosthesis 100. The height H1 of the transcatheter aortic valve prosthesis 100, measured from the inflow end 140 to the outflow end 150, is 50-51 mm.

FIGS. 6A, 6B, 7A, 7B, 7C, 8, 9, 10, and 11 depict an embodiment of a transcatheter aortic valve prosthesis 200 that includes a frame 210 having one or more access cells 215 in accordance with an embodiment hereof. In the embodiment shown, the frame 210 of the transcatheter aortic valve prosthesis 200 includes four rows of first cells 214 and exactly one row of access cells 215, wherein the one row of access cells 215 includes nine access cells 215 described herein. In this embodiment, the frame 210 includes nine inflow crowns 216A formed at the inflow end 240 of the frame 210 and nine outflow crowns 216B formed at the outflow end 250 of the frame 210, but this is not meant to be limiting.

Figure 6A:
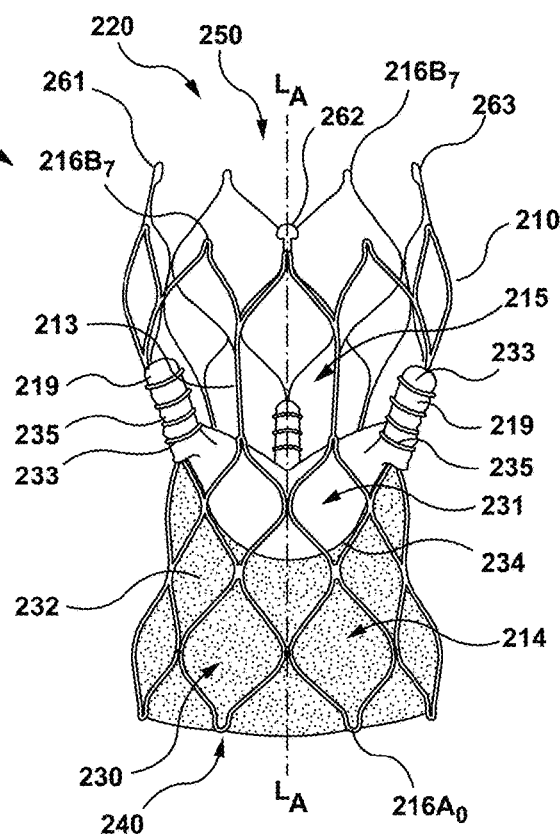
FIGS. 6A and 6B show perspective side views of a transcatheter aortic valve prosthesis according to another embodiment hereof, wherein the transcatheter aortic valve prosthesis includes one row of nine access cells.
Figure 6B:
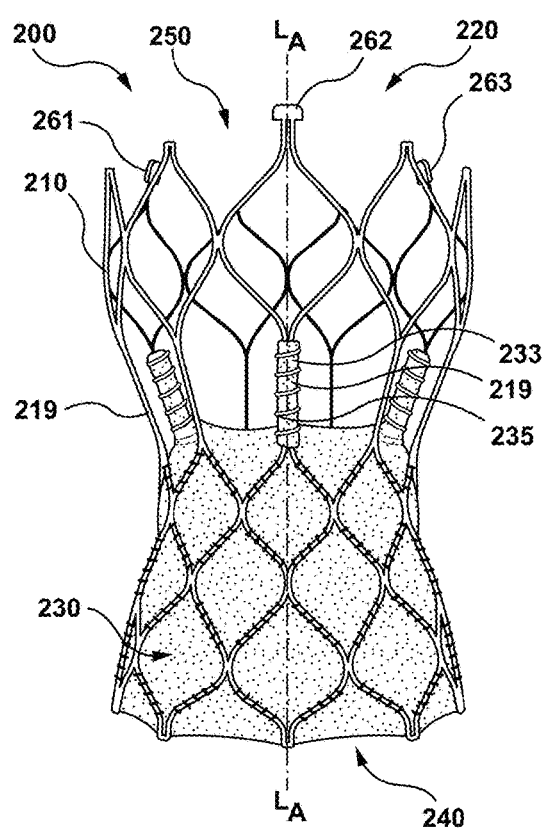

As shown in FIGS. 6A and 6B, the transcatheter aortic valve prosthesis 200 includes a frame 210 having an inflow end 240 and an outflow end 250, and a valve component 230 disposed within the frame 210. The frame 210 of the transcatheter aortic valve prosthesis 200 includes a plurality of struts 211 that are arranged to form a plurality of cells arranged circumferentially around a longitudinal axis $L_A$ of the transcatheter aortic valve prosthesis 200 and longitudinally to form a tubular structure. The struts 211 are defined herein as the elongated wire segments of the frame 210. In the embodiment shown, the plurality of cells include a plurality of first cells 214 and one or more access cells 215 wherein the one or more access cells 215 each have an enlarged area relative or compared to each of the first cells 214. The valve component 230 is disposed within a central lumen 220 of the frame 210, and the valve component 230 is attached to the frame 210. The frame 210 secures the transcatheter aortic valve prosthesis 200 in place in situ within the vasculature of the patient.

Figure 10:
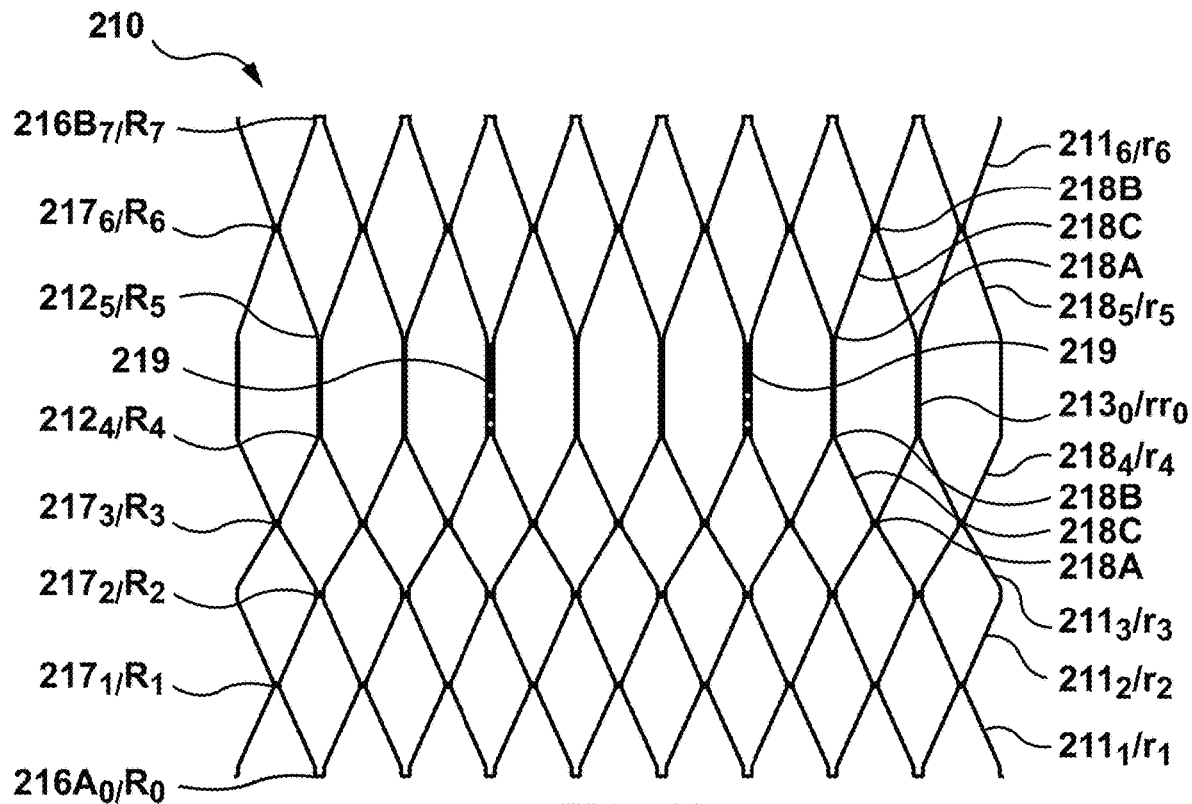
FIG. 10 depicts a flat, expanded configuration of the frame of the transcatheter aortic valve prosthesis of FIGS. 6A and 6B.

As can be seen in FIG. 6A, the plurality of struts 211 are arranged at the inflow end 240 of the frame 210 such that two adjacent struts 211 of the plurality of struts 211 come together to form a crown 216 at the inflow end 240. Thus, a row or plurality of inflow crowns 216A are formed at the inflow end 240 of the frame 210. As best shown in FIG. 10, in this embodiment, the frame 210 includes exactly nine inflow crowns 216A, but this is not meant to be limiting. The inflow end of the frame 210 also forms an end of the transcatheter aortic valve prosthesis 200. The plurality of struts 211 are arranged at the outflow end 250 of the frame 210 such that two adjacent struts 211 of the plurality of struts 211 come together to form a crown 216 at the outflow end 250. Thus, as best shown in FIG. 10, the frame 210 includes exactly nine outflow crowns 216B formed at the outflow end 250 of the frame 210, but this is not limiting. The outflow end 250 of the frame 210 also forms an end of the transcatheter aortic valve prosthesis 200. As described in more detail below, exactly three struts 211 come together to form a tri-strut connection 212, and exactly four struts 211 come together to form a node 217, as can be seen in FIG. 10. The first cells 214 and the access cells 215, that will be described in further detail herein, are defined as the spaces between the plurality of struts 211, tri-strut connections 212, crowns 216, and nodes 217. The frame 210 is self-expanding and may be formed from any of the materials listed above for the frame 110.

Figure 9:
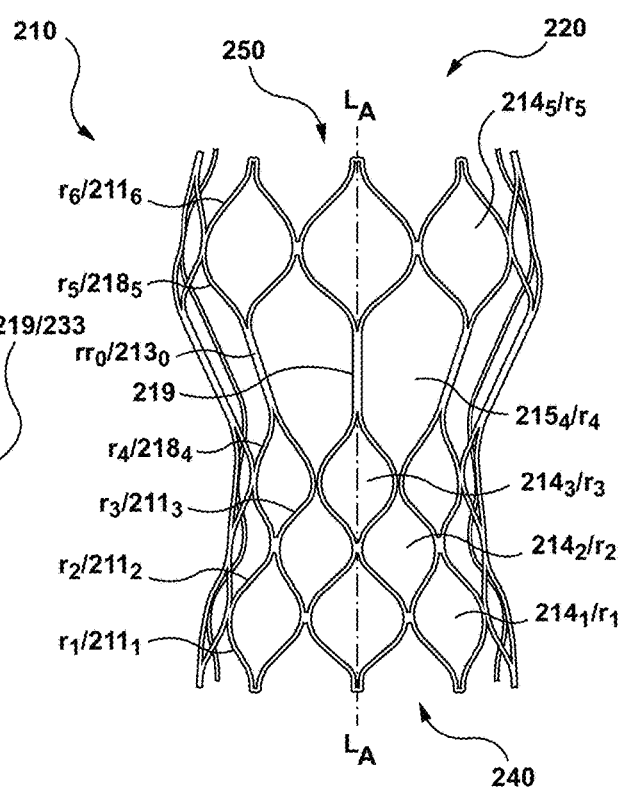
FIG. 9 depicts a side view of a frame of the transcatheter aortic valve prosthesis of FIGS. 6A and 6B.

The frame 210 of the transcatheter aortic valve prosthesis 200 includes a plurality of first cells 214 arranged circumferentially around the longitudinal axis $L_A$ of the transcatheter aortic valve prosthesis 200 and longitudinally to form a tubular structure, as best shown in FIG. 9. Each first cell 214 of the plurality of first cells 214 are formed by exactly four struts 211, exactly four nodes 217 or exactly three nodes 217 and exactly one crown 216, and are generally diamond-shaped. In embodiments, the plurality of first cells 214 will vary in size depending on the position of the first cell 214 within the frame 210, i.e., row placement and/or longitudinal position on the frame 210. For example, in some embodiments, the plurality of first cells 214 disposed near the inflow end 240 and the outflow end 250 of the frame 210 are larger than the plurality of first cells 214 disposed at a midline or midportion of the frame 210. In other embodiments, the plurality of first cells 214 disposed near the outflow end 250 of the frame 210 are larger than the plurality of first cells 214 disposed near the inflow end 240 of the frame 210. In the embodiment described herein, each access cell 215 is always larger in size than each first cell 214 of the plurality of first cells 214.

Figure 7A:
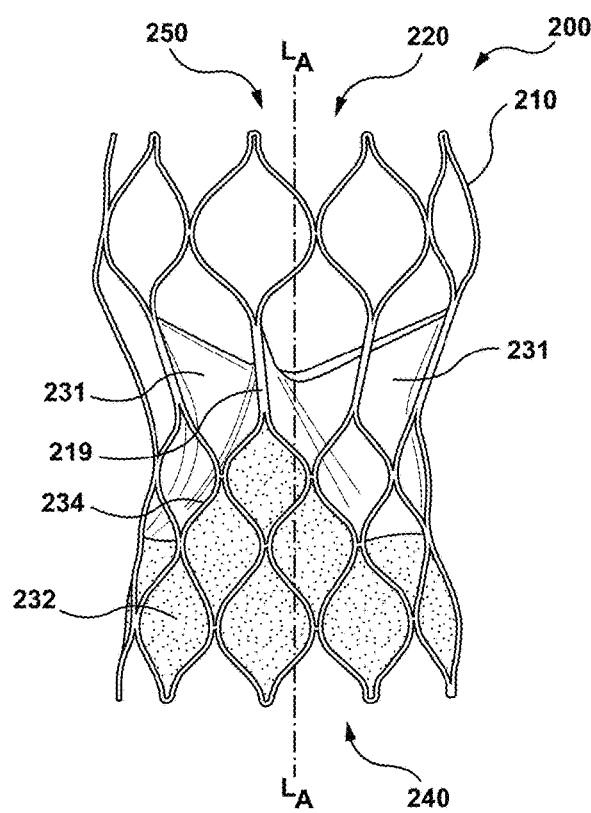
FIG. 7A depicts a perspective side view of the transcatheter aortic valve prosthesis of FIGS. 6A and 6B.

The frame 210 of the transcatheter aortic valve prosthesis 200 is described herein for illustrative purposed in terms of horizontal rows of crowns 216, nodes 217 and/or tri-strut connections 212, and horizontal rows of struts 211 and cells 214, 215. Each row of struts and cells is disposed between two adjacent rows of the crowns, nodes, and/or tri-strut connections. In FIGS. 6A-6B, 7A, and 9-10, subscripts have been added to the reference numerals for the crowns 216, nodes 217, tri-strut connections 212, struts 211, first cells 214 and access cells 215 to indicate the row number of each type of frame component starting with the inflow end 240. The frame 210 includes a total of eight rows of crowns 216, nodes 217, and tri-strut connections 212, as seen in FIG. 7A. In such an embodiment, beginning at the inflow end 240 of the frame 210, the row $R_0$ describes the row of inflow crowns $216A_0$ at the inflow end 240 of the frame 210. Disposed directly adjacent to the row $R_0$ of inflow crowns $216A_0$ is the row $R_1$ of nodes $217_1$, and directly adjacent to the row $R_1$ of nodes $217_1$ is the row $R_2$ of nodes $217_2$. This naming convention for the nodes 217 continues up to the row $R_3$ of nodes $217_3$, wherein disposed directly adjacent to the row $R_3$ of nodes $217_3$ is the row $R_4$ of tri-strut connections $212_4$, and disposed directly adjacent to the row $R_4$ of tri-strut connections $212_4$ is the row $R_5$ of tri-strut connections $212_5$. Disposed directly adjacent to the row $R_5$ of tri-strut connections $212_5$ is the row $R_6$ of nodes $217_6$, and disposed directly adjacent to the row $R_6$ of nodes $217_6$ is the row $R_7$ of outflow crowns $216B_7$ at the outflow end 250 of the frame 210.

In the embodiment shown, the frame 210 can include exactly four rows of first cells 214 and exactly one row of access cells 215. Beginning at the inflow end 240, the row $r_1$ to the row $r_3$ describes the first three rows of first cells 214. In particular, each first cell $214_1$ in the row $r_1$ is defined by an inflow crown $216A_0$ in the row $R_0$, two struts $211_1$ in the row $r_1$, two nodes $217_1$ in the row $R_1$, two struts $211_2$ in the row $r_2$, and one node $217_2$ in the row $R_2$. The first cells $214_2$, $214_3$ in rows $r_2$ and $r_3$ are defined the same as described above with respect to the row $r_1$ of first cells $214_1$. Disposed directly adjacent to the row $r_3$ of first cells $214_3$ is the row $r_4$ of access cells $215_4$, and disposed directly adjacent to the row $r_4$ of access cells $215_4$ is the row $r_5$ of first cells $214_5$ at the outflow end 250 of the frame 210, as shown in FIG. 9.

The struts 211 are also numbered in rows beginning at the inflow end 240 of the frame 210, as shown in FIG. 10. For example, the struts 211 that come together to form the inflow crowns 216A in the row $R_0$ at the inflow end 240 are denoted as row $r_1$ of struts $211_1$. The struts in between the row $R_1$ of nodes $217_1$ and the row $R_2$ of nodes $217_2$ are denoted as row $r_2$ of struts $211_2$. Disposed directly adjacent to the row $r_2$ of struts $211_2$ is the row $r_3$ of struts $211_3$ and disposed directly adjacent to row $r_3$ of struts $211_3$ is the row $r_4$ of optimized struts $218_4$, which will be described in more detail below. Disposed directly adjacent to row $r_4$ of optimized struts $218_4$ is row $rr_0$ of axial struts $213_0$, and disposed directly adjacent to row $rr_0$ of axial struts $213_0$ is row $r_5$ of optimized struts $218_5$. Disposed directly adjacent to row $r_5$ of optimized struts $218_5$ is row $r_6$ of struts $211_6$. As can be seen in FIG. 10, a row $rr_0$ of axial struts $213_0$ is disposed between row $r_4$ of optimized struts $218_4$ and row $r_5$ of optimized struts $218_5$, as described in further detail below. The term "axial strut" is used herein to describe a strut that runs substantially parallel to the longitudinal axis of the transcatheter aortic heart valve. In other words, an axial strut does not have a substantially diagonal disposition, but rather, has 0° of tilt and runs axially with respect to the longitudinal axis of the prosthesis.

The access cells 215 are enlarged cells configured to provide improved access to a patient's percutaneous coronary arteries if a percutaneous coronary intervention procedure is required post-implantation of transcatheter aortic valve prosthesis 200. In this embodiment, the area of the at least one access cell 215 is approximately equivalent to the area of three first cells 214 combined, specifically the first cells 214 disposed directly adjacent to the access cells 215 nearest to the inflow end 240. Stated another way, the area of an access cell 215 compared to the area of a first cell 214 adjacent to at least one of the access cells 215 on the inflow side 240 is approximately a 3:1 ratio. In other words, a first cell 214 adjacent to at least one of the access cells 215 nearest to the inflow end 240 has an area that is approximately 33% of an area of one of the access cells 215 of the frame 210, with "approximately" including a tolerance of 5%. In another embodiment, a first cell 214 adjacent to at least one of the access cells 215 has an area that is between 29% and 33% of an area of one of the access cells 115 of the frame 110. The area of the at least one access cell 215 may be between 130-132 mm$^2$ and the area of a first cell 214 is between 40-42 mm$^2$.

Figure 8:
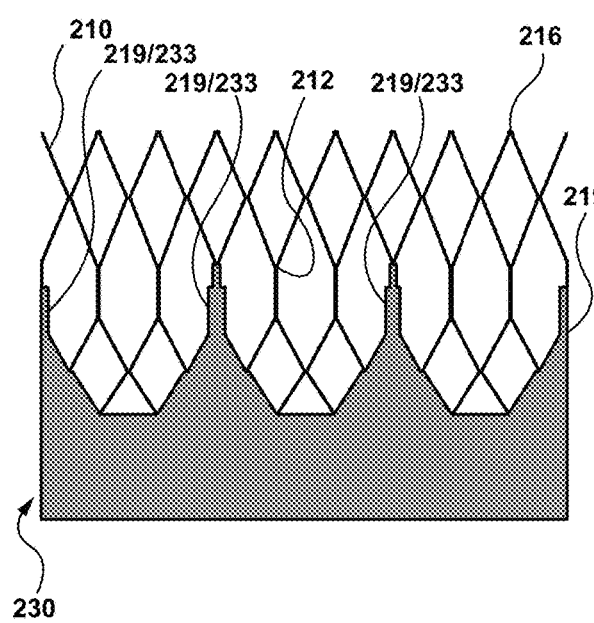
FIG. 8 depicts a flat, expanded configuration of the transcatheter aortic valve prosthesis of FIGS. 6A and 6B.

In the embodiment shown, the frame 210 of the transcatheter aortic valve prosthesis 200 includes a row $r_4$ of nine access cells $215_4$, as shown in the flat, expanded configuration of the prosthesis 200 in FIG. 8. The nine access cells $215_4$ are disposed in the row $r_4$ between the row $r_3$ of first cells $214_3$ and the row $r_5$ of first cells $214_5$ of the frame 210. The row $r_4$ of access cells $215_4$ are enclosed by the row $R_3$ of nodes $217_3$, the row $r_4$ of optimized struts $218_4$ which are described in more detail below, the row $R_4$ of tri-strut connections $212_4$, a row $rr_0$ of axial struts $213_0$, the row $R_5$ of tri-strut connections $212_5$, the row $r_5$ of optimized struts $218_5$ (described in more detail below), and the row $R_6$ of nodes $217_6$, as best shown in FIG. 10. Commissure posts 219 are located on every third axial strut 213, as can be seen in FIG. 8 and FIG. 10. Stated another way, the three commissure posts 219 are axial struts 213 which have the leaflet commissures attached thereto, as described in more detail below.

In the embodiment shown, the crimp strain of the frame 210 where the access cells $215_4$ are located, in row $r_4$ of access cells $215_4$, is reduced by modifying the struts as described above for the optimized struts 118 of the frame 110. The optimized struts $218_4$ in the row $r_4$ and the optimized struts $218_5$ in the row $r_5$ that enclose, or form, an inflow-most end of the access cell 215 and an outflow-most end of the access cell 215 have a width profile and a length that differ from a width profile and length of a standard strut 211 of the frame 210. Each standard strut of the plurality of standard struts has a first width profile and a first length, and each optimized strut of the plurality of optimized struts has a width profile that is different from the first width profile and a length that is different from the first length. The term "optimized strut" is used herein to describe a strut that is altered, or configured, for a specific purpose as compared to a "standard strut" of the frame 210 which is not altered or configured for this purpose. In this embodiment, the optimized struts described herein are altered or configured to reduce crimp strains around the access cells 215, while the remaining struts of the frame 210 are standard struts which are not altered or configured for this purpose. In the embodiments shown, the plurality of struts of the frame 210, including both standard struts 211 and optimized struts 218, have a uniform thickness. The uniform thickness of the plurality of struts may be approximately 0.45-0.48 mm. In an alternative embodiment (not shown), the struts that enclose or form the inflow-most end and the outflow-most end of each the access cells $215_4$ of the frame 210 are not optimized or modified relative to the standard struts and have the same width and/or length as the rest of the struts 211 of the frame 210.

In the embodiment shown, one or more paddles are each attached to an outflow crown $216B_7$ in the row $R_7$ on the frame 210 as shown in FIGS. 6A-6B. The paddles are configured to removably couple the transcatheter aortic valve prosthesis 200 to a delivery system (not shown). While FIGS. 6A-6B show a first paddle 261, a second paddle 262, and a third paddle 263, one skilled in the art will realize that more or fewer paddles can be utilized, and those paddles can be replaced with other components such as eyelets, loops, slots, or any other suitable coupling member.

The valve component 230 is disposed inside and coupled to an interior surface of the frame 210 of the transcatheter aortic valve prosthesis 200, as shown in FIGS. 6A-6B and 7A-7C, and includes three valve leaflets 231 and a skirt 232. In the embodiment shown, the three valve leaflets 231 are sewn using sutures 235 or otherwise securely attached along their bases to the skirt 232 at a margin of attachment 234, which can be seen in FIGS. 6A, 7A and 7C. Alternatively, the transcatheter aortic valve prosthesis 200 may include one valve leaflet 231 or two valve leaflets 231. Adjoining pairs of valve leaflets 231 are attached to one another at their lateral ends to form commissures 233. Three of the nine axial struts 213 act as commissure posts 219 that align with and attach to a respective commissure 233 of the three valve leaflets 231 of the valve component 230, as best shown in FIG. 8. The valve component 230 is configured to block flow in one direction to regulate flow therethrough via the valve leaflets 231 that form a replacement bicuspid or tricuspid valve. FIG. 7B depicts a top view of the outflow end 250 of the transcatheter aortic valve prosthesis 200. FIG. 7B illustrates the configuration of the three valve leaflets 231 within the central lumen 220 of the transcatheter aortic valve prosthesis 200. The valve component 230 can be coupled to the frame 210 through any suitable manner known in the art, such as sewing the valve component 230 to the frame 210 using sutures 235, as shown in FIGS. 6A-6B. The valve component 230 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

The skirt 232 of the valve component 230 is attached to the interior surface of the frame 210 through any suitable manner known in the art, such as sewing the skirt 232 to the frame 210 using sutures 235. As best shown in FIGS. 6A and 6B, the skirt 232 lines the interior surface of the frame 210 such that the first cells 214 disposed near the inflow end 240 of the frame 210 that overlap with the skirt 232 are covered by the skirt 232. In embodiments, the skirt 232 may cover approximately one-third of the interior surface of the frame 210 beginning at the inflow end 240. The skirt 232 is configured to direct blood flow through the central lumen 220 of the transcatheter aortic valve prosthesis 200 and to the valve leaflets 231 of the valve component 230. The skirt 232 may be formed of various flexible materials including but not limited to, natural pericardial material such as tissue from bovine, equine or porcine origins, or synthetic materials such as polytetrafluoroethylene (PTFE), DACRON® polyester, pyrolytic carbon, or other biocompatible materials.

Figure 11:
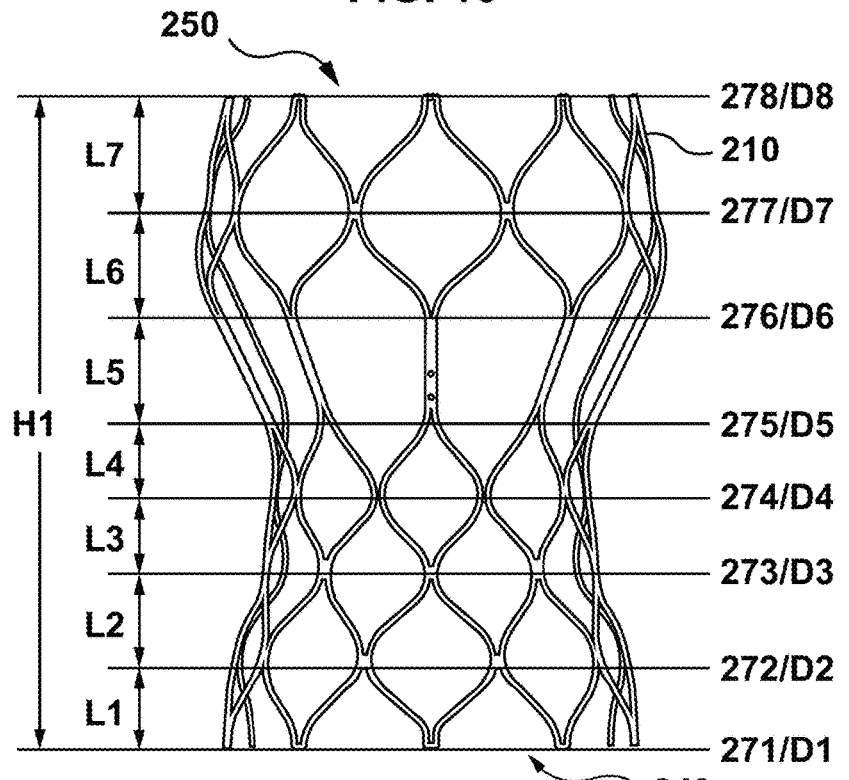
FIG. 11 depicts a side view of the frame of the transcatheter aortic valve prosthesis of FIGS. 6A and 6B.

FIG. 11 depicts the frame 210 of the transcatheter aortic valve prosthesis 200 with horizontal lines denoting where various measurements have been recorded, however this is not meant to be limiting. For example, the diameter D1 of the frame 210 at horizontal line 271 is 30-31 mm. The diameter D2 of the frame 210 at horizontal line 272 is 28-29 mm. The distance L1 between horizontal line 271 and horizontal line 272 is 6-7 mm. The diameter D3 of the frame 210 at horizontal line 273 is 23-24 mm. The distance L2 between horizontal line 272 and horizontal line 273 is 6-7 mm. The diameter D4 of the frame 210 at horizontal line 274 is 22-23 mm. The distance L3 between horizontal line 273 and horizontal line 274 is 5-6 mm. The diameter D5 of the frame 210 at horizontal line 275 is 23-24 mm. The distance L4 between horizontal line 274 and horizontal line 275 is 5-6 mm. The diameter D6 of the frame 210 at horizontal line 276 is 29-30 mm. The distance L5 between horizontal line 275 and horizontal line 276 is 7-8 mm. The diameter D7 of the frame 210 at horizontal line 277 is 33-34 mm. The distance L6 between horizontal line 276 and horizontal line 277 is 7-8 mm. The diameter D8 of the frame 210 at horizontal line 278 is 30-31 mm. The distance L7 between horizontal line 277 and horizontal line 278 is 8-9 mm. The total height H1 of the frame 210, measured from the inflow end 240 to the outflow end 250, is 47-48 mm.

FIGS. 12A-12C, 13, 14, 15, 16 depict an embodiment of a transcatheter aortic valve prosthesis 300 that includes a frame 310 having one or more access cells 315 in accordance with an embodiment hereof. In the embodiment shown, the frame 310 of the transcatheter aortic valve prosthesis 300 includes four rows of first cells 314 and exactly one row of access cells 315, wherein the one row of access cells 315 includes six access cells 315. In the embodiment shown, the frame 310 includes twelve inflow crowns 316A formed at the inflow end 340 of the frame 310 and six outflow crowns 316B formed at the outflow end 350 of the frame 310, but this is not meant to be limiting.

Figure 12A:
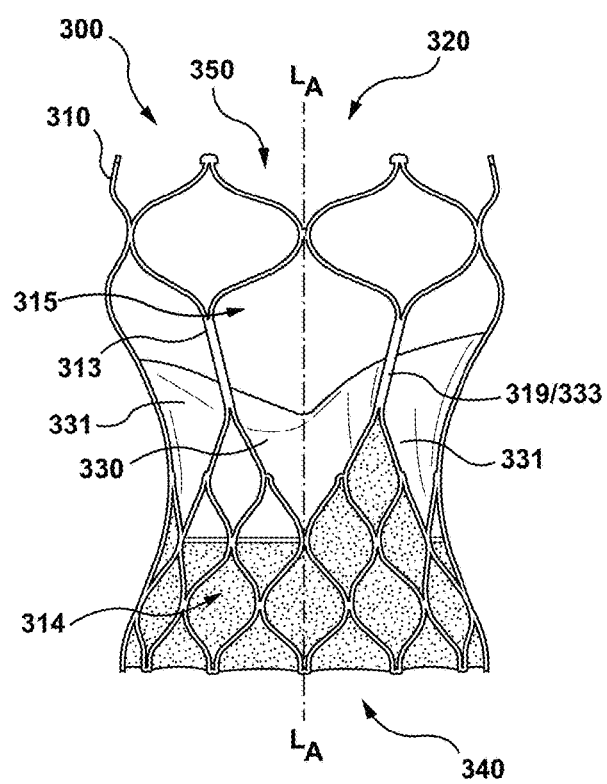
FIG. 12A depicts a perspective side view of a transcatheter aortic valve prosthesis according to another embodiment hereof, wherein the transcatheter aortic valve prosthesis includes one row of six access cells.
Figure 14:
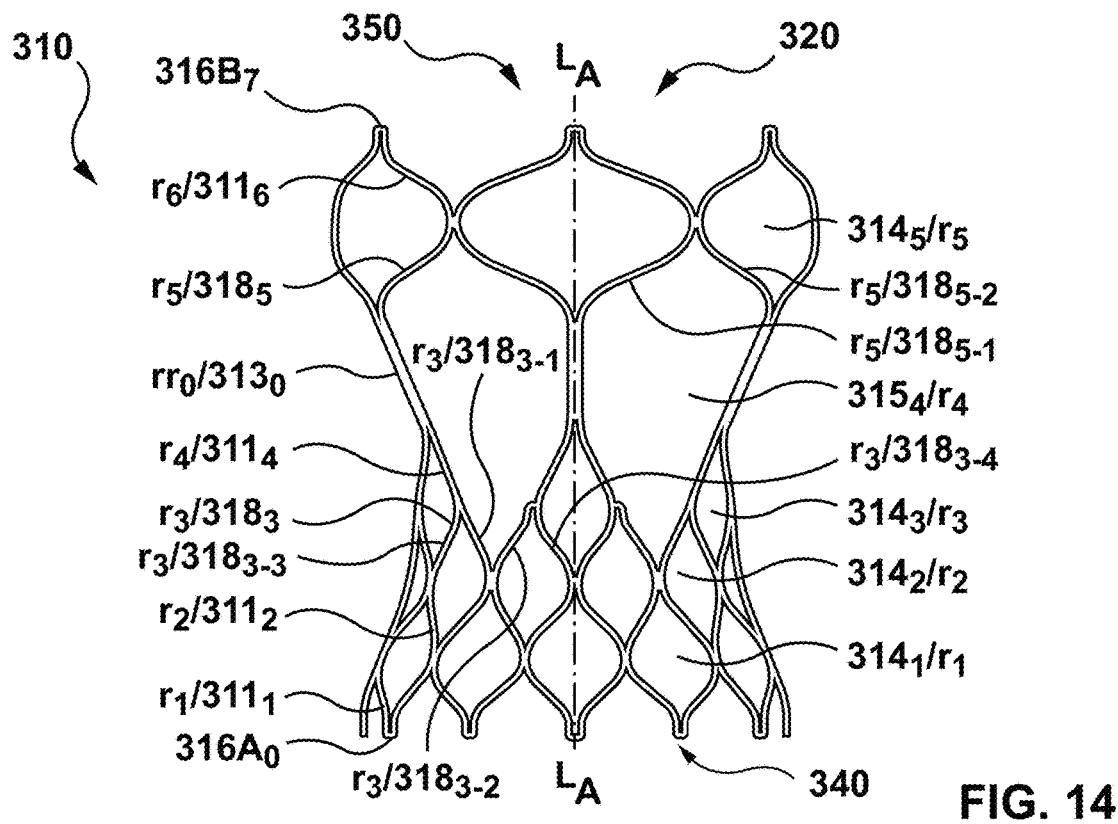
FIG. 14 depicts a side view of a frame of the transcatheter aortic valve prosthesis of FIG. 12A.

As shown in FIG. 12A, the transcatheter aortic valve prosthesis 300 includes a frame 310 having an inflow end 340 and an outflow end 350, and a valve component 330 disposed within the frame 310. The frame 310 of the transcatheter aortic valve prosthesis 300 includes a plurality of struts 311 that are arranged to form a plurality of cells arranged circumferentially around a longitudinal axis $L_A$ of the transcatheter aortic valve prosthesis 300 and longitudinally to form a tubular structure. The struts 311 are defined as the elongated wire segments of the frame 310, as can be seen in FIG. 14. In the embodiment shown, the plurality of cells include a plurality of first cells 314 and one or more access cells 315. The one or more access cells 315 each have an enlarged area relative or compared to the first cells 314. The valve component 330 is disposed within a central lumen 320 of the frame 310, and the valve component 330 is attached to the frame 310. The frame 310 secures the transcatheter aortic valve prosthesis 300 in place in situ within the vasculature of the patient.

Figure 15:
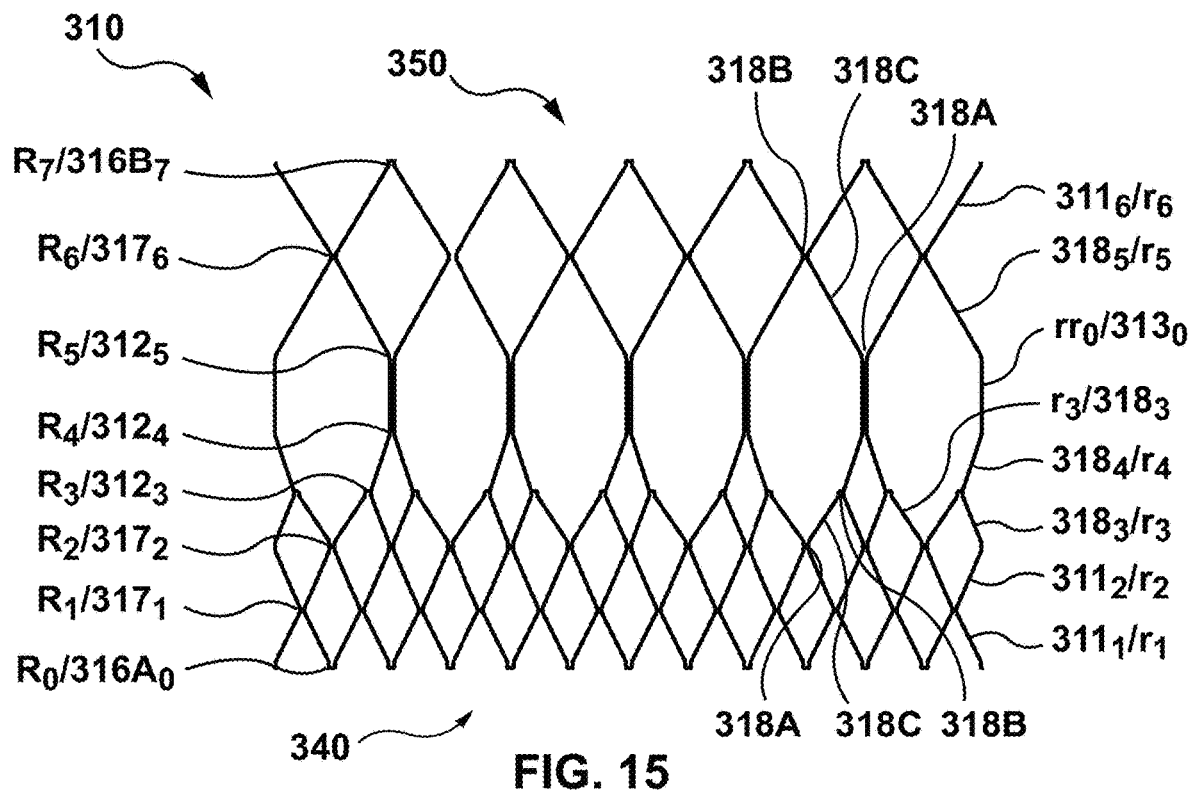
FIG. 15 depicts a flat, expanded configuration of the frame of the transcatheter aortic valve prosthesis of FIG. 12A.

As can be seen in FIG. 14, the plurality of struts 311 are arranged at the inflow end 340 of the frame 310 such that two adjacent struts of the plurality of struts 311 come together to form a crown 316 at the inflow end 340. Thus, a row or plurality of inflow crowns 316A are formed at the inflow end 340 of the frame 310. As best shown in FIG. 15, in this embodiment, the frame 310 includes exactly twelve inflow crowns 316A at the inflow end 340 of the frame 310, but this is not meant to be limiting. The inflow end 340 of the frame 310 also forms an inflow end of the transcatheter aortic valve prosthesis 300. The plurality of the struts 311 are arranged at the outflow end 350 of the frame 310 such that two adjacent struts 311 of the plurality of struts 311 come together to form a crown 316 at the outflow end 350. Thus, as best shown in FIG. 15, the frame 310 includes exactly six outflow crowns 316B formed at the outflow end 350 of the frame 310, but this is not limiting. The outflow end 350 of the frame 310 also forms an outflow end of the transcatheter aortic valve prosthesis 300. Exactly three struts 311 come together to form a tri-strut connection 312, and exactly four struts 311 come together to form a node 317, as can be seen in FIG. 15. The first cells 314 and the access cells 315 are defined as the open spaces or windows formed between the plurality of struts 311, tri-strut connections 312, crowns 316, and/or nodes 317. The frame 310 is self-expanding and may be formed from any of the materials listed above for the frame 110.

The frame 310 of the transcatheter aortic valve prosthesis 300 includes a plurality of the first cells 314 arranged circumferentially around the longitudinal axis $L_A$ of the transcatheter aortic valve prosthesis 300 and longitudinally to form a tubular structure, as best shown in FIG. 14. Each first cell 314 of the plurality of first cells 314 are formed by exactly four struts 311 and exactly four nodes 317 or exactly three nodes 317 and exactly one crown 316 and are generally diamond-shaped. In embodiments, the plurality of first cells 314 vary in size depending on the position of the first cell 314 within the frame 310, i.e., row placement and/or longitudinal position on the frame 310. For example, in some embodiments, the plurality of first cells 314 disposed near the inflow end 340 and the outflow end 350 of the frame 310 may be larger than the plurality of first cells 314 disposed at a midline or midportion of the frame 310. In other embodiments, the plurality of first cells 314 disposed near the outflow end 350 of the frame 310 may be larger than the plurality of first cells 314 disposed near the inflow end 340 of the frame 310. In the embodiment described herein, each access cell 315 is always larger than each first cell 314 of the plurality of first cells 314.

The frame 310 of the transcatheter aortic valve prosthesis 300 is described herein for illustrative purposes in terms of horizontal rows of crowns 316, nodes 317 and/or tri-strut connections 312, and horizontal rows of struts 311 and cells 314, 315. Each row of struts and cells is disposed between two adjacent rows of the crowns, nodes, and/or tri-strut connections. In FIGS. 12A, 14 and 15, subscripts have been added to the reference numerals for the crowns 316, nodes 317, tri-strut connections 312, struts 311, axial struts 313, first cells 314 and access cells 315 to indicate the row number of each type of frame component starting with the inflow end 340. The frame 310 includes a total of eight rows of crowns 316, nodes 317, and tri-strut connections 312, as best shown in FIG. 15. In such an embodiment, beginning at the inflow end 340 of the frame 310, the row $R_0$ describes the row of inflow crowns $316A_0$ at the inflow end 340 of the frame 310. As seen in FIG. 15, disposed directly adjacent to the row $R_0$ of inflow crowns $316A_0$ is the row $R_1$ of nodes $317_1$, and directly adjacent the row $R_1$ of nodes $317_1$ is the row $R_2$ of nodes $317_2$. Disposed directly adjacent to the row $R_2$ of nodes $317_2$ is the row $R_3$ of tri-strut connections $312_3$, and disposed directly adjacent to the row $R_3$ of tri-strut connections $312_3$ is the row $R_4$ of tri-strut connections $312_4$. Disposed directly adjacent to the row $R_4$ of tri-strut connections $312_4$ is the row $R_5$ of tri-strut connections $312_5$, and disposed directly adjacent to the row $R_5$ of tri-strut connections $312_5$ is the row $R_6$ of nodes $317_6$. Disposed directly adjacent to the row $R_6$ of nodes $317_6$ is the row $R_7$ of outflow crowns $316B_7$ at the outflow end 350 of the frame 310.

In the embodiment shown, the frame 310 can include exactly four rows of first cells 314 and exactly one row of access cells 315, as best shown in FIG. 14. Beginning at the inflow end 340, the row $r_1$ to the row $r_3$ describe the first three rows of first cells 314, as shown in FIG. 14. In particular, each first cell $314_1$ in the row $r_1$ is defined by an inflow crown $316A_0$ in the row $R_0$, two struts $311_1$ in the row $r_1$, two nodes $317_1$ in the row $R_1$, two struts $311_2$ in the row $r_2$, and one node $317_2$ in the row $R_2$. The first cells $317_2$ and $317_3$ in rows $r_2$ and $r_3$ thereof are defined the same as described above with respect to the row $r_1$ of first cells $317_1$. Disposed directly adjacent to the row $r_3$ of first cells $314_3$ is the row $r_4$ of access cells $315_4$, and disposed directly adjacent to the row $r_4$ of access cells $315_4$ is the row $r_5$ of first cells $314_5$ at the outflow end 350.

The struts 311 are also numbered in rows beginning at the inflow end 340 of the frame 310, as shown in FIG. 14. For example, the struts 311 that come together to form the inflow crowns 316A at the inflow end 340 are denoted as row $r_1$ of struts $311_1$. The struts 311 in between the row $R_1$ of nodes $317_1$ and the row $R_2$ of nodes $317_2$ are denoted as row $r_2$ of struts $311_2$. Disposed directly adjacent to row $r_2$ of struts $311_2$ is row $r_3$ of optimized struts $318_3$, which is described in further detail below. Disposed directly adjacent to row $r_3$ of optimized struts $318_3$ is row $r_4$ of struts $311_4$. Disposed directly adjacent to row $r_4$ of optimized struts $318_4$ is row $rr_0$ of axial struts $313_0$, and disposed directly adjacent to row $rr_0$ of axial struts $313_0$ is row $r_5$ of optimized struts $318_5$. Disposed directly adjacent to row $r_5$ of optimized struts $318_5$ is row $r_6$ of struts $311_6$. As shown in FIG. 14, a row $rr_0$ of axial struts $313_0$ is disposed between row $r_4$ of struts $311_4$ and row $r_5$ of optimized struts $318_5$, described in further detail below.

The access cells 315 are enlarged cells configured to provide improved access to a patient's percutaneous coronary arteries if a percutaneous coronary intervention procedure is required post-implantation of transcatheter aortic valve prosthesis 300. In this embodiment, the area of the access cell 315 is approximately equivalent to the area of seven first cells 314 combined, specifically the first cells 314 disposed directly adjacent to the access cells 315 at the outflow end 350. Stated another way, the area of an access cell 315 compared to the area of a first cell 314 adjacent to the access cell 315 at the outflow end 350 is approximately a 7:1 ratio. In other words, a first cell 314 adjacent to an access cell 315 at the outflow end 350 has an area that is approximately 14% of an area of one of the access cells 315 of the frame 310, with "approximately" including a tolerance of 5%. In another embodiment, a first cell 314 adjacent to at least one of the access cells 315 has an area that is between 11% and 15% of an area of one of the access cells 115 of the frame 110. The area of the at least one access cell 315 may be between 211-212 mm$^2$ and the area of a first cell 314 is between 28-29 mm$^2$.

Figure 13:
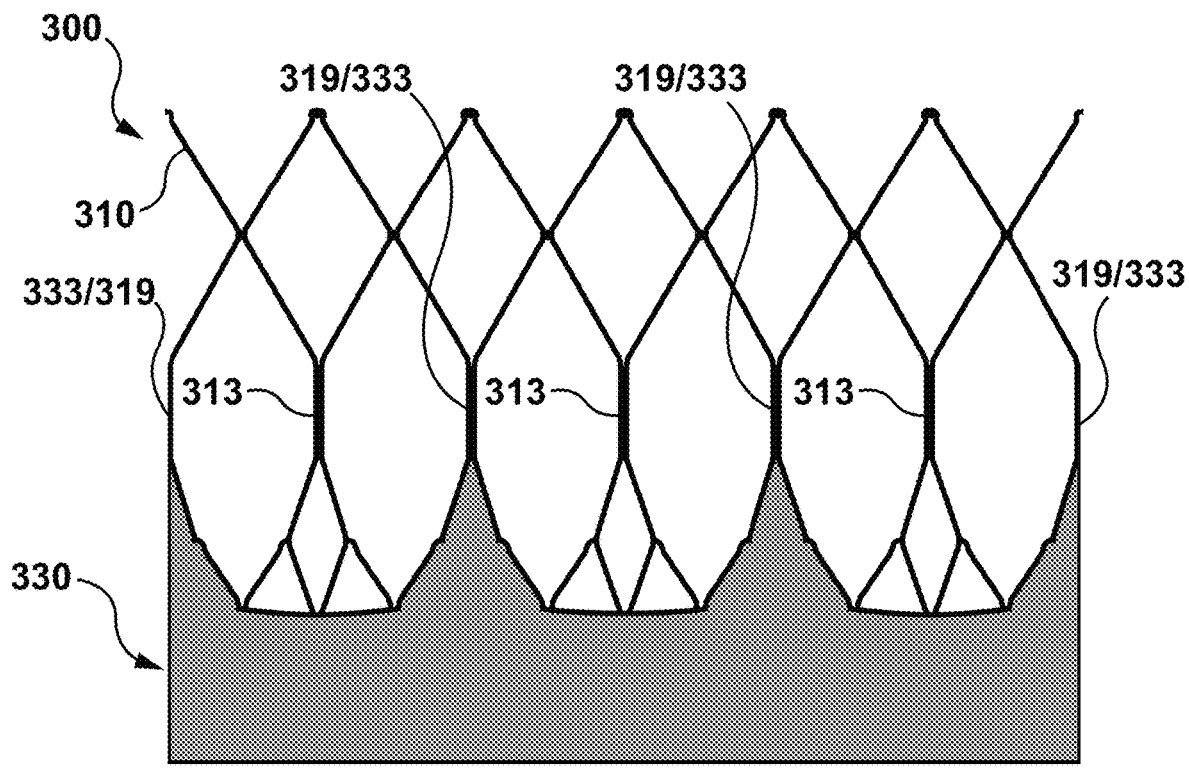
FIG. 13 depicts a flat, expanded configuration of the transcatheter aortic valve prosthesis of FIG. 12A.

In the embodiment shown, the frame 310 of the transcatheter aortic valve prosthesis 300 includes the row $r_4$ of six access cells $315_4$, as shown in the flat, expanded configuration of the frame 310 in FIG. 15. The six access cells 315 are disposed in the row $r_4$ between the row $r_3$ of first cells $314_3$ and the row $r_5$ of first cells $314_5$ of the frame 310. The row $r_4$ of access cells $315_4$ are enclosed by the row $R_2$ of nodes $317_2$, the row $r_3$ of optimized struts $318_3$ (described in more detail below), the row $R_3$ of tri-strut connections $312_3$, the row $r_4$ of struts $311_4$, the row $R_4$ of tri-strut connections $312_4$, the row $rr_0$ of axial struts $313_0$, the row $R_5$ of tri-strut connections $312_5$, the row $r_5$ of optimized struts $318_5$ (described in more detail below), and the row $R_6$ of nodes $317_6$. The commissure posts 319 are located on every other axial strut 313, as can be seen in FIG. 13. Stated another way, the three commissure posts 319 are axial struts 313 which have leaflet commissures attached thereto, as described in more detail below.

In the embodiment shown, the crimp strain of the frame 310 where the access cells $315_4$ are located, in row $r_4$ of access cells $315_4$, is reduced by modifying a first optimized strut $318_{3-1}$ in the row $r_3$ and a second optimized strut $318_{3-2}$ in the row $r_3$ that form or enclose an inflow-most end of the access cell 315, a third optimized strut $318_{3-3}$ in the row $r_3$ disposed directly adjacent to the first optimized strut $318_{3-1}$, and a fourth optimized strut $318_{3-4}$ in the row $r_3$ disposed directly adjacent to the second optimized strut $318_{3-2}$, as shown in FIG. 14 and as described above for the optimized struts 118 of the frame 110. The crimp strain of the frame 310 where the access cells 315 are located is reduced by modifying a first optimized strut $318_{5-1}$ in the row $r_5$ and a second optimized strut $318_{5-2}$ in the row $r_5$ that form or define an outflow-most end of the access cell 315, as shown in FIG. 14 and as described above for the optimized struts 118 of the frame 110. The standard struts $311_4$ in the row $r_4$ that enclose the access cells 315, are not modified. Each standard strut of the plurality of standard struts has a first width profile and a first length, and each optimized strut of the plurality of optimized struts has a width profile that is different from the first width profile and a length that is different from the first length. The term "optimized strut" is used herein to describe a strut that is altered, or configured, for a specific purpose as compared to a "standard strut" of the frame 310 which is not altered or configured for this purpose. In this embodiment, the optimized struts described herein are altered or configured to reduce crimp strains around the access cells 315, while the remaining struts of the frame 310 are standard struts which are not altered or configured for this purpose. In the embodiments shown, the plurality of struts of the frame 310, including both standard struts 311 and optimized struts 318, have a uniform thickness. The uniform thickness of the plurality of struts may be between 0.45-0.48 mm. In an alternative embodiment (not shown), the struts that enclose the access cells $315_4$ of the frame 310 are not optimized or modified relative to the standard struts and have the same width and/or length as the rest of the struts 311 of the frame 310.

Figure 12B:
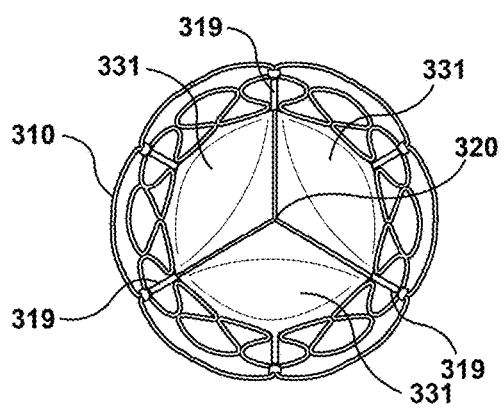
FIG. 12B depicts a top view of the transcatheter aortic valve prosthesis of FIG. 12A.
Figure 12C:
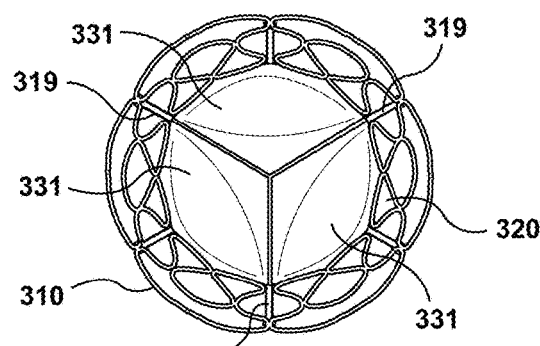
FIG. 12C depicts a bottom view of the transcatheter aortic valve prosthesis of FIG. 12A.

The valve component 330 is disposed inside and coupled to an interior surface of the frame 310 of the transcatheter aortic valve prosthesis 300, as shown in FIGS. 12A-12C and FIG. 13, and includes three valve leaflets 331. Alternatively, the valve component 330 of the transcatheter aortic valve prosthesis 300 may include one valve leaflet 331 or two leaflets 331. This embodiment may include a skirt such as the skirt from the previous embodiment, but the skirt is not shown in FIG. 12A for sake of clarity. Similar to previous embodiments, the three valve leaflets 331 may be sewn using sutures or otherwise securely attached along their bases to the skirt at a margin of attachment (not shown). The valve component 330 is configured to block flow in one direction to regulate flow therethrough via the valve leaflets 331 that form a replacement bicuspid or tricuspid valve. FIG. 12B depicts a top view of the outflow end 350 of the transcatheter aortic valve prosthesis 300. FIG. 12B illustrates the configuration of the three valve leaflets 331 within the central lumen 320 of the transcatheter aortic valve prosthesis 300. FIG. 12C depicts a bottom view of the inflow end 340 of the transcatheter aortic valve prosthesis 300. The valve component 330 can be coupled to the frame 310 any suitable manner known in the art, such as sewing the valve component 330 to the frame 310 using sutures (not shown). Adjoining pairs of valve leaflets 331 are attached to one another at their lateral ends to form commissures 333. Three of the six axial struts 313 act as commissure posts 319 that align with and attach to a respective commissure 333 of the three valve leaflets 331 of the valve component 330, as best shown in FIG. 13. The valve component 330 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Figure 16:
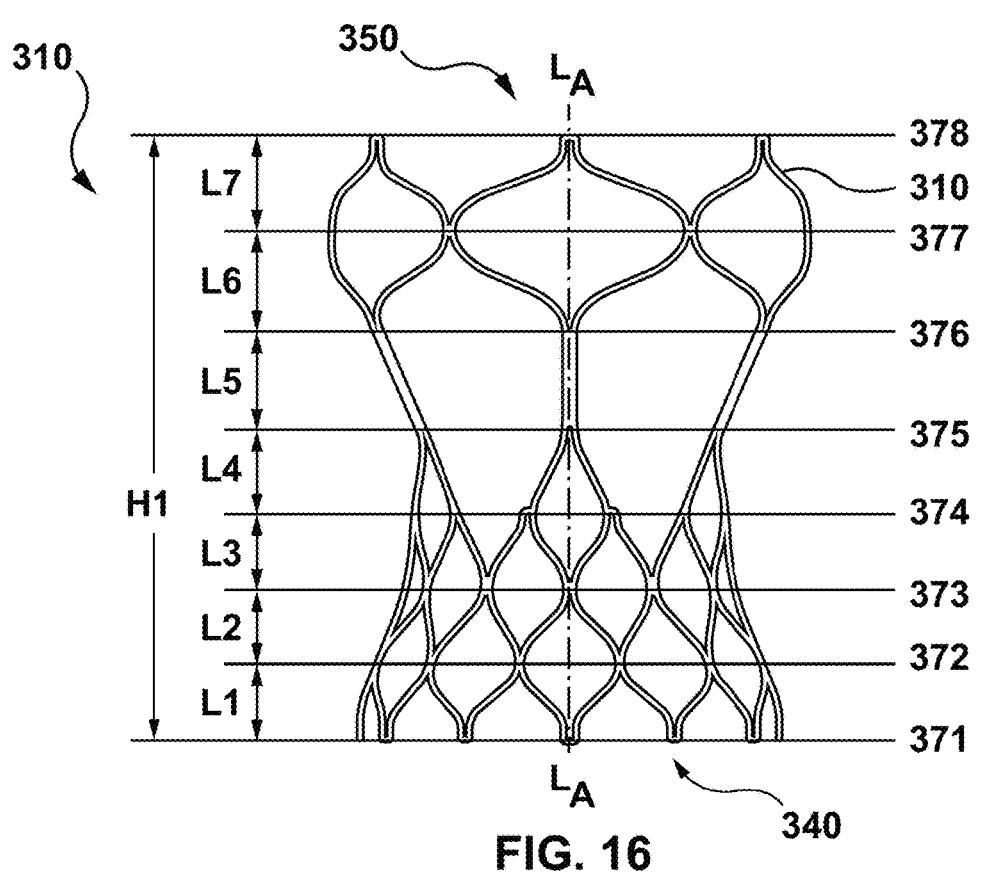
FIG. 16 depicts a side view of the frame of the transcatheter aortic valve prosthesis of FIG. 12A.

FIG. 16 depicts the frame 310 of the transcatheter aortic valve prosthesis 300 with horizontal lines denoting where various measurements have been recorded, however this is not meant to be limiting. For example, the diameter D1 of the frame 310 at horizontal line 371 is 29-30 mm. The diameter D2 of the frame 310 at horizontal line 372 is 27-28 mm. The distance L1 between horizontal line 371 and horizontal line 372 is 5-6 mm. The diameter D3 of the frame 310 at horizontal line 373 is 23-24 mm. The distance L2 between horizontal line 372 and horizontal line 373 is 5-6 mm. The diameter D4 of the frame 310 at horizontal line 374 is 22-23 mm. The distance L3 between horizontal line 373 and horizontal line 374 is 5-6 mm. The diameter D5 of the frame 310 at horizontal line 375 is 24-25 mm. The distance L4 between horizontal line 374 and horizontal line 375 is 5-6 mm. The diameter D6 of the frame 310 at horizontal line 376 is 31-32 mm. The distance L5 between horizontal line 375 and horizontal line 376 is 6-7 mm. The diameter D7 of the frame 310 at horizontal line 377 is 33-32 mm. The distance L6 between horizontal line 376 and horizontal line 377 is 6-7 mm. The diameter D8 of the frame 310 at horizontal line 378 is 30-31 mm. The distance L7 between horizontal line 377 and horizontal line 378 is 6-7 mm. The total height H1 of the frame 310, measured from the inflow end 340 to the outflow end 350, is 42-43 mm.

FIGS. 17A-17C, 18, 19, 20, 21 depict an embodiment of a transcatheter aortic valve prosthesis 400 that includes a frame 410 having one or more access cells 415 in accordance with an embodiment hereof. In the embodiment shown, the frame 410 of the transcatheter aortic valve prosthesis 400 includes seven rows of first cells 414 and exactly one row of access cells 415, wherein the one row of access cells 415 includes three access cells 415. In the embodiment shown, the frame 410 includes twelve inflow crowns 416A formed at the inflow end 440 of the frame 410 and twelve outflow crowns 416B formed at the outflow end 450 of the frame 410, but this is not meant to be limiting.

Figure 17A:
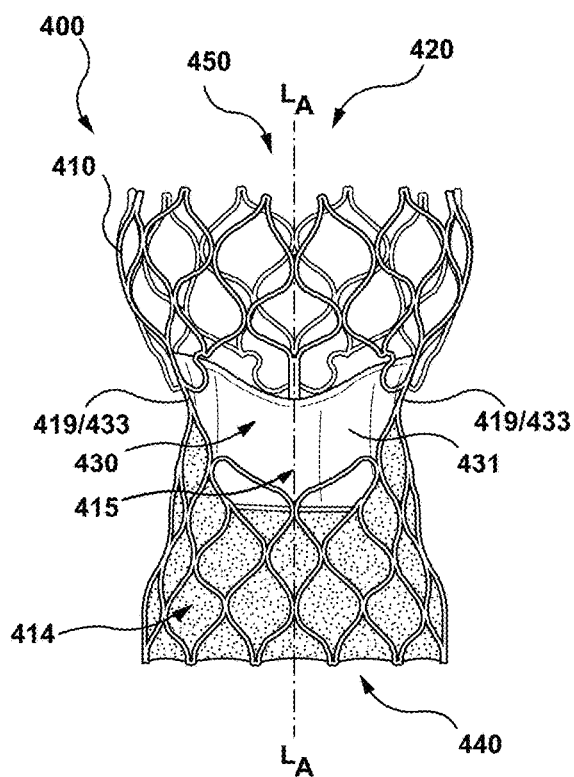
FIG. 17A depicts a perspective side view of a transcatheter aortic valve prosthesis according to another embodiment hereof, wherein the transcatheter aortic valve prosthesis includes one row of three access cells.

As shown in FIG. 17A, the transcatheter aortic valve prosthesis 400 includes a frame 410 having an inflow end 440 and an outflow end 450, and a valve component 430 disposed within the frame 410. The frame 410 of the transcatheter aortic valve prosthesis 400 includes a plurality of struts 411 that are arranged to form a plurality of cells arranged circumferentially around a longitudinal axis $L_A$ of the transcatheter aortic valve prosthesis 400 and longitudinally to form a tubular structure. The struts 411 are defined herein as the elongated wire segments of the frame 410. In the embodiment shown, the plurality of cells include a plurality of first cells 414 and one or more access cells 415 wherein the one or more access cells 415 each have an enlarged area relative or compared to the first cells 414. The valve component 430 is disposed within a central lumen 420 of the frame 410, and the valve component 430 is attached to the frame 410. The frame 410 secures the transcatheter aortic valve prosthesis 400 in place in situ within the vasculature of the patient.

Figure 19:
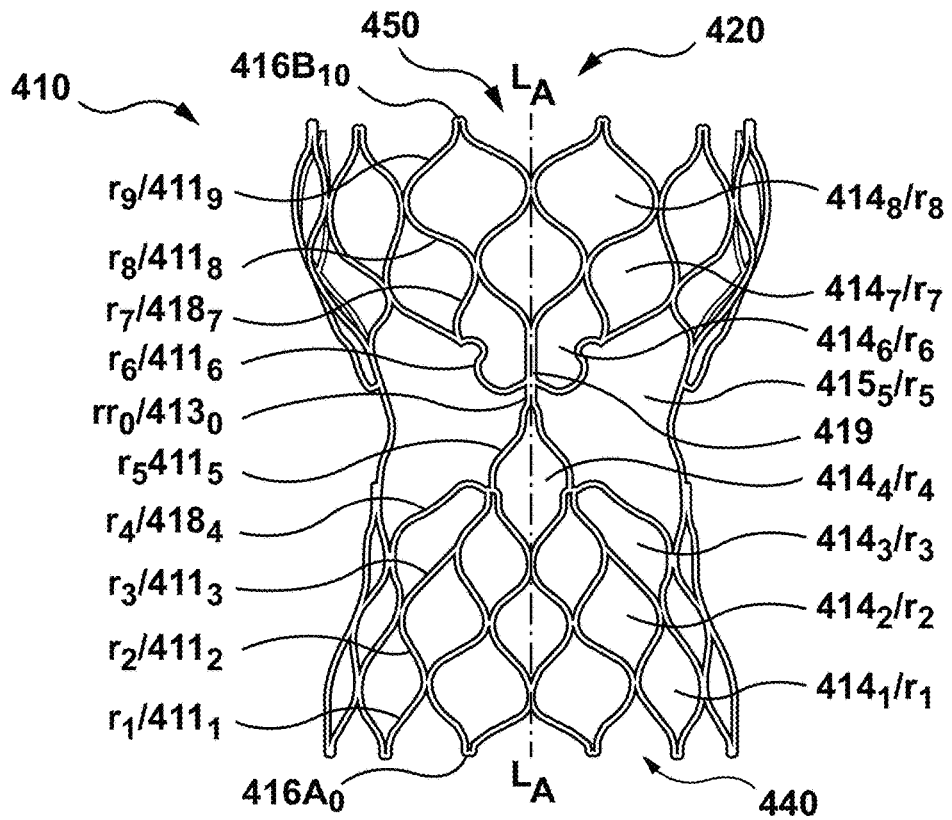
FIG. 19 depicts a side view of a frame of the transcatheter aortic valve prosthesis of FIG. 17A.
Figure 20:
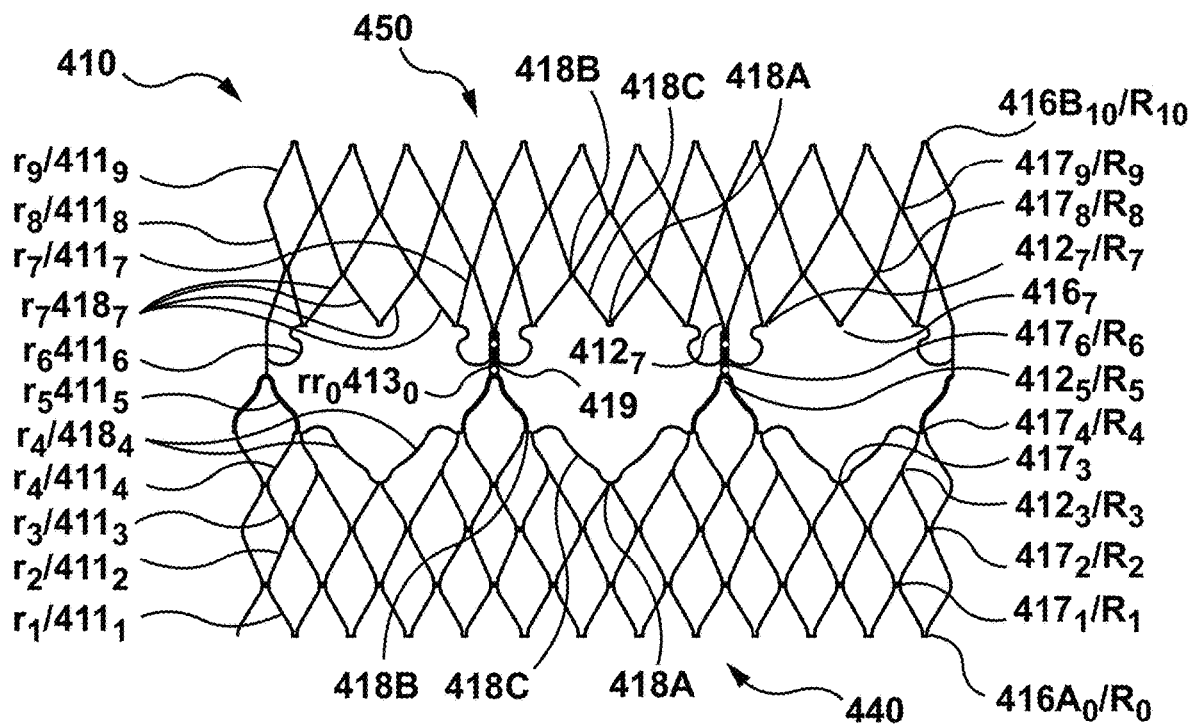
FIG. 20 depicts a flat, expanded configuration of the frame of the transcatheter aortic valve prosthesis of FIG. 17A.

As can be seen in FIG. 19, the plurality of struts 411 are arranged at the inflow end 440 of the frame 410 such that two adjacent struts 411 of the plurality of struts 411 come together to form a crown 416 at the inflow end 440. Thus, a row or plurality of inflow crowns 416A are formed at the inflow end 440 of the frame 410. As best shown in FIG. 20, in this embodiment, the frame 410 includes exactly twelve inflow crowns 416A at the inflow end 440 of the frame 410, but this is not meant to be limiting. The inflow end 440 of the frame 410 also forms an end of the transcatheter aortic valve prosthesis 400. The plurality of the struts 411 are arranged at the outflow end 450 of the frame 410 such that two adjacent struts 411 of the plurality of struts 411 come together to form a crown 416 at the outflow end 450. Thus, as best shown in FIG. 20, the frame 410 includes exactly twelve outflow crowns 416B formed at the outflow end 450 of the frame 410, but this is not limiting. The outflow end 450 of the frame 410 also forms an end of the transcatheter aortic valve prosthesis 400. As described in more detail below, exactly three struts 411 come together to form a tri-strut connection 412, and exactly four struts 411 come together to form a node 417, as can be seen in FIG. 20. The first cells 414 and the access cells 415, that will be described in further detail herein, are defined as the spaces between the plurality of struts 411, tri-strut connections 412, crowns 416, and nodes 417. The frame 410 is self-expanding and may be formed from any material described above with reference to the frame 110.

The frame 410 of the transcatheter aortic valve prosthesis 400 includes a plurality of first cells 414 arranged circumferentially around the longitudinal axis $L_A$ of the transcatheter aortic valve prosthesis 400 and longitudinally to form a tubular structure, as best shown in FIG. 19. Each first cell 414 of the plurality of first cells 414 are formed by exactly four struts 411 and exactly four nodes 417 or exactly three nodes 417 and exactly one crown 416 and are generally diamond-shaped. In embodiments, the plurality of first cells 414 vary in size depending on the position of the first cell 414 within the frame 410, i.e., row placement and/or longitudinal position on the frame 410. For example, in some embodiments, the plurality of first cells 414 disposed near the inflow end 440 and the outflow end 450 of the frame 410 may be larger than the plurality of first cells 414 disposed at a midline or midportion of the frame 410. In other embodiments, the plurality of first cells 414 disposed near the outflow end 450 of the frame 410 may be larger than the plurality of first cells 414 disposed near the inflow end 440 of the frame 410. In all embodiments described herein, each access cell 415 is always larger in size than each first cell 414 of the plurality of first cells 414.

The frame 410 of the transcatheter aortic valve prosthesis 400 is described herein for illustrative purposes in terms of horizontal rows of crowns 416, nodes 417 and/or tri-strut connections 412, and horizontal rows of struts 411 and cells 414, 415. Each row of struts and cells is disposed between two adjacent rows of the crowns, nodes, and/or tri-strut connections. In FIGS. 19 and 20, subscripts have been added to the reference numerals for the crowns 416, nodes 417, tri-strut connections 412, struts 411, axial struts 413, first cells 414 and access cells 415 to indicate the row number of each type of frame component starting with the inflow end 440. The frame 410 includes a total of eleven rows of crowns 416, nodes 417, and tri-strut connections 412, as shown in FIG. 20. In such an embodiment, beginning at the inflow end 440 of the frame 410, the row $R_0$ described the row of inflow crowns $416A_0$ at the inflow end 440 of the frame 410. Disposed directly adjacent to the row $R_0$ of inflow crowns $416A_0$ is the row $R_1$ of nodes $417_1$, and this naming convention continues up to the row $R_3$ of nodes $417_3$. The row $R_3$ also includes tri-strut connections $412_3$. Disposed directly adjacent to the row $R_3$ of nodes $417_3$ is the row $R_4$ of nodes $417_4$. Disposed directly adjacent to the row $R_4$ of nodes $417_4$ is the row $R_5$ of tri-strut connections $412_5$, and disposed directly adjacent to the row $R_5$ of tri-strut connections $412_5$ is the row $R_6$ of nodes $417_6$. Disposed directly adjacent to the row $R_6$ of nodes $417_6$ is the row $R_7$ of tri-strut connections $412_7$. The row $R_7$ also includes crowns $416_7$. Disposed directly adjacent to the row $R_7$ of tri-strut connections $412_7$ is the row $R_8$ and $R_9$ of nodes $417_8$ and $417_9$. Disposed directly adjacent to the row $R_9$ of nodes $417_9$ is the row $R_{10}$ of outflow crowns $416B_{10}$ at the outflow end 450 of the frame 410.

In the embodiment shown, the frame 410 can include exactly seven rows of first cells 414 and exactly one row of access cells 415. Beginning at the inflow end 440, the row $r_1$ to the row $r_4$ denotes the first four rows of first cells $414_1$ to $414_4$, as shown in FIG. 19. In particular, each first cell $414_1$ in the row $r_1$ is defined by an inflow crown $416A_0$ in the row $R_0$, two struts $411_1$ in the row $r_1$, two nodes $417_1$ in the row $R_1$, two struts $411_2$ in the row $r_2$, and one node $417_2$ in the row $R_2$. The first cells $414_2$ to $414_4$ in rows $r_2$ to $r_4$ thereof are defined the same as described above with respect to the row $r_1$ of first cells $114_1$. Disposed directly adjacent to the row $r_4$ of first cells $414_4$ is the row $r_5$ of access cells $415_5$, and disposed directly adjacent to the row $r_5$ of access cells $415_5$ is the row $r_6$ of first cells $414_6$ at the outflow end 450. Disposed directly adjacent to the row $r_6$ of first cells $414_6$ are the rows $r_7$ and $r_8$ of first cells $414_7$ and $414_8$ at the outflow end 450 of the frame 410.

The struts 411 are also numbered in rows beginning at the inflow end 440 of the frame 410, as shown in FIG. 19. For example, the struts 411 that come together to form the inflow crowns $416A$ in the row $R_0$ at the inflow end 440 are denoted as row $r_1$ of struts $411_1$. The struts 411 in between the row $R_1$ of nodes $417_1$ and the row $R_2$ of nodes $417_2$ are denoted as row $r_2$ of struts $411_2$. Disposed directly adjacent to row $r_2$ of struts $411_2$ is row $r_3$ of struts $411_3$. Disposed directly adjacent to row $r_3$ of struts $411_3$ is row $r_4$ that includes struts $411_4$ and optimized struts $418_4$, which is described in more detail below. Disposed directly adjacent to row $r_4$ is row $r_5$ of optimized struts $418_5$ and disposed directly adjacent to row $r_5$ of optimized struts $418_5$ is row $rr_8$ of axial struts $413_8$. Disposed directly adjacent to row $rr_8$ of axial struts $413_8$ is row $r_6$ of optimized struts $418_6$, and disposed directly adjacent to row $r_6$ is row $r_7$ that includes both struts $411_7$ and optimized struts $418_7$. Disposed directly adjacent to row $r_7$ is row $r_8$ of struts $411_8$ and row $r_9$ of struts $411_9$ at the outflow end 450 of the frame 410.

The access cells 415 are enlarged cells configured to provide improved access to a patient's percutaneous coronary arteries if a percutaneous coronary intervention procedure is required post-implantation of transcatheter aortic valve prosthesis 400. In this embodiment, the area of the at least one access cell 415 is approximately equivalent to the area of eight first cells 414 combined, specifically the first cells 414 disposed at the inflow end 440 of the frame 410. Stated another way, the area of an access cell 415 compared to the area of a first cell 414 disposed at the inflow end 440 of the frame 410 is approximately an 8:1 ratio. In other words, a first cell 414 at the inflow end 440 of the frame 410 has an area that is approximately 12% of an area of one of the access cells 415 of the frame 410, with "approximately" including a tolerance of 5%. In another embodiment, a first cell 414 adjacent to at least one of the access cells 415 has an area that is between 10% and 14% of an area of one of the access cells 415 of the frame 410. The area of the at least one access cell 415 may be between 252-254 mm$^2$ and the area of a first cell 414 is between 29-30 mm$^2$.

Figure 18:
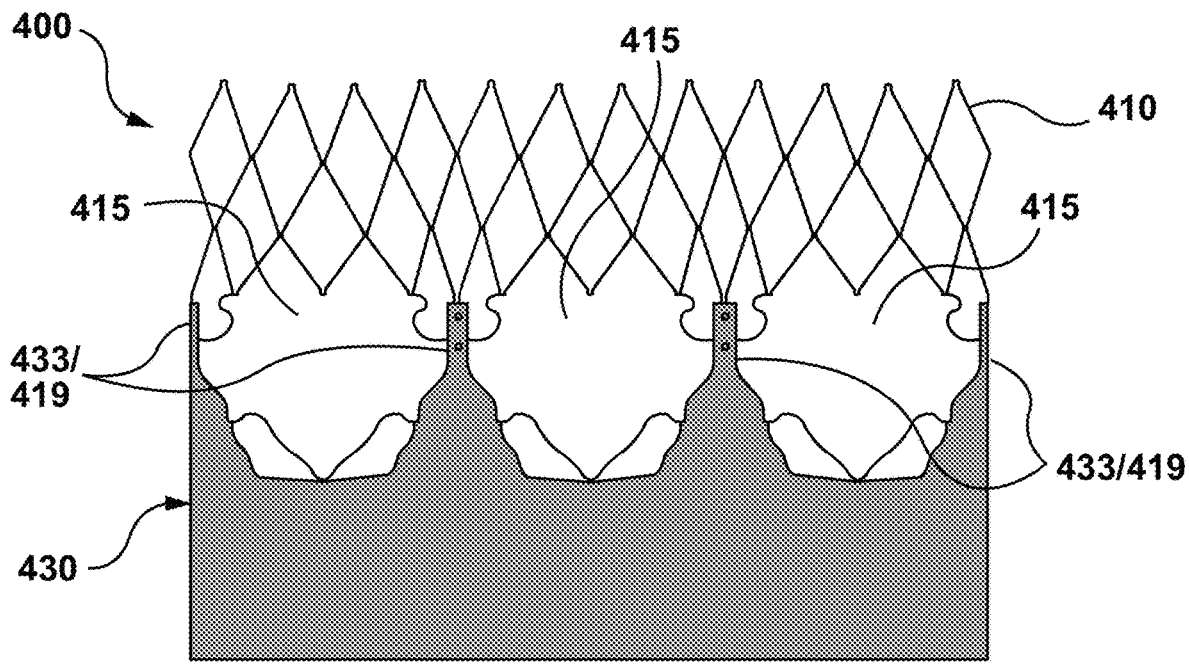
FIG. 18 depicts a flat, expanded configuration of the transcatheter aortic valve prosthesis of FIG. 17A.

In the embodiment shown, the frame 410 of the transcatheter aortic valve prosthesis 400 includes the row $r_5$ of exactly three second cells $415_5$, as shown in the flat, expanded configuration of the frame 410 in FIG. 20. The row $r_5$ of access cells $415_5$ are enclosed by the row $R_3$ of nodes $417_3$, the row $r_4$ of optimized struts $418_4$ (described in more detail below), the row $R_4$ of nodes $417_4$, the row $r_5$ of struts $411_5$, the row $R_5$ of tri-strut connections $412_5$, the row $rr_0$ of axial struts $413_0$, the row $R_6$ of nodes $417_6$, the row $r_6$ of struts $411_6$, the row $R_7$ that includes tri-strut connections $412_7$ and crowns $416_7$, the row $r_7$ of optimized struts $418_7$ (described in more detail below), and the row $R_8$ of nodes $417_8$. The commissure posts 419 are located on every axial strut 413, as can be seen in FIG. 18. Stated another way, in this embodiment which includes exactly three axial struts 413, each axial strut 413 is a commissure post which has a leaflet commissure attached thereto, as described in more detail below.

In the embodiment shown, the crimp strain of the frame 410 where the access cells $415_5$ are located, in row $r_5$ of access cells $415_5$, is reduced by modifying the struts 418 that enclose, or define, the inflow-most ends of the access cells $415_5$ and the outflow-most ends of the access cells $415_5$. The optimized struts $418_4$ in the row $r_4$ form the inflow-most ends of the access cells $415_5$ and the optimized struts $418_7$ in the row $r_7$ form the outflow-most ends of the access cells $415_5$, as best shown in FIG. 20 and as described above for the optimized struts 118 of the frame 110. In some embodiments, the struts disposed directly adjacent to the optimized struts 418 that enclose the inflow-most ends and outflow-most ends of the access cells 415 are also modified, as described above for the optimized struts 118 of the frame 110. The standard struts $411_5$ and $411_6$ in the rows $r_5$ and $r_6$ that enclose the access cells 415, are not modified. Each standard strut of the plurality of standard struts has a first width profile and a first length, and each optimized strut of the plurality of optimized struts has a width profile that is different from the first width profile and a length that is different from the first length. The term "optimized strut" is used herein to describe a strut that is altered, or configured, for a specific purpose as compared to a "standard strut" of the frame 410 which is not altered or configured for this purpose. In this embodiment, the optimized struts described herein are altered or configured to reduce crimp strains around the access cells 415, while the remaining struts of the frame 410 are standard struts which are not altered or configured for this purpose. In the embodiments shown, the plurality of struts of the frame 410, including both standard struts 411 and optimized struts 418, have a uniform thickness. The uniform thickness of the plurality of struts may be approximately 0.45-0.48 mm. In an alternative embodiment (not shown), the struts 411 that enclose the access cells $415_5$ of the frame 410 are not optimized or modified relative to the standard struts and have the same width and/or length as the rest of the struts 411 of the frame 410.

Figure 17B:
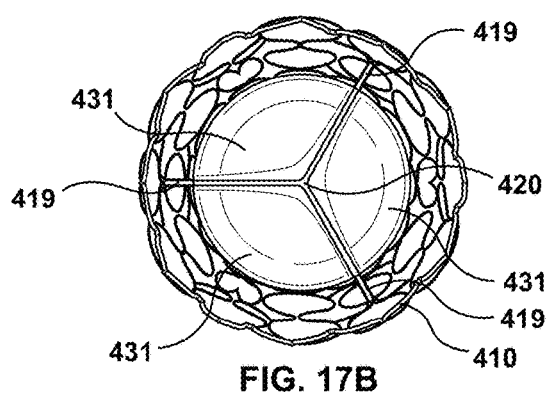
FIG. 17B depicts a top view of the transcatheter aortic valve prosthesis of FIG. 17A.
Figure 17C:
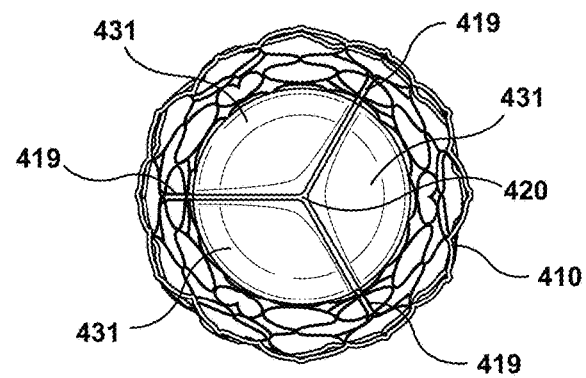
FIG. 17C depicts a bottom view of the transcatheter aortic valve prosthesis of FIG. 17A.

The valve component 430 is disposed inside and coupled to an interior surface of the frame 410 of the transcatheter aortic valve prosthesis 400, as shown in FIGS. 17A-17C and FIG. 18, and includes three valve leaflets 431. Alternatively, the valve component 430 of the transcatheter aortic valve prosthesis 400 may include one valve leaflet 431 or two leaflets 431. This embodiment may include a skirt such as a skirt from a previous embodiment, but the skirt is not shown in FIG. 17A for sake of clarity. Similar to previous embodiments, the three valve leaflets 431 may be sewn using sutures or otherwise securely attached along their bases to the skirt at a margin of attachment (not shown). The valve component 430 is configured to block flow in one direction to regulate flow therethrough via the valve leaflets 431 that form a replacement bicuspid or tricuspid valve. FIG. 17B depicts a top view of the outflow end 450 of the transcatheter aortic valve prosthesis 400. FIG. 17B illustrates the configuration of the three valve leaflets 431 within the central lumen 420 of the transcatheter aortic valve prosthesis 400. FIG. 17C depicts a bottom view of the inflow end 440 of the transcatheter aortic valve prosthesis 400. The valve component 430 can be coupled to the frame 410 through any suitable manner known in the art, such as sewing the valve component 430 to the frame 410 using sutures (not shown). Adjoining pairs of valve leaflets 431 are attached to one another at their lateral ends to form commissures 433. All three of the axial struts 413 act as commissure posts 419 that align with and attach to a respective commissure 433 of the three valve leaflets 431 of the valve component 430, as best shown in FIG. 18. The valve component 430 may be formed of various flexible materials including, but not limited to natural pericardial material such as tissue from bovine, equine or porcine origins, or synthetic materials such as polytetrafluoroethylene (PTFE), DACRON® polyester, pyrolytic carbon, or other biocompatible materials. With certain prosthetic leaflet materials, it may be desirable to coat one or both sides of the replacement valve leaflet with a material that will prevent or minimize overgrowth. It is further desirable that the prosthetic leaflet material is durable and not subject to stretching, deforming, or fatigue.

Figure 21:
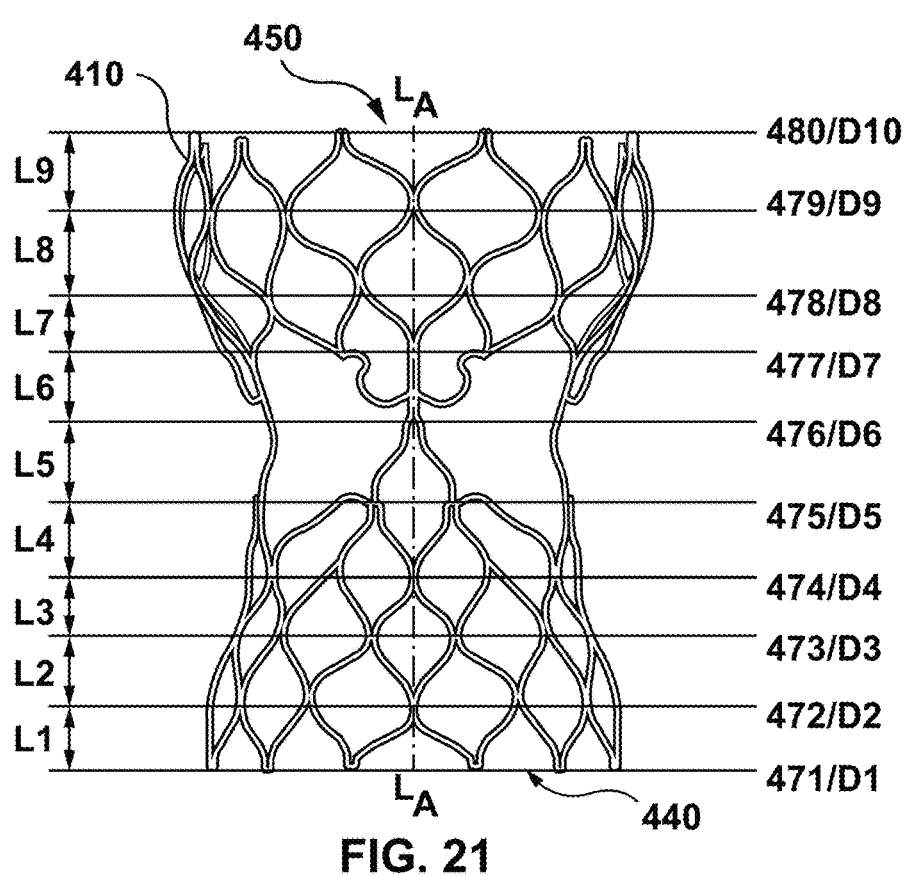
FIG. 21 depicts a side view of the frame of the transcatheter aortic valve prosthesis of FIG. 17A.

FIG. 21 depicts the frame 410 of the transcatheter aortic valve prosthesis 400 with horizontal lines denoting where various measurements have been recorded, however this is not meant to be limiting. For example, the diameter D1 of the frame 410 at horizontal line 471 is 30-31 mm. The diameter D2 of the frame 410 at horizontal line 472 is 28-29 mm. The distance L1 between horizontal line 471 and horizontal line 472 is 4-5 mm. The diameter D3 of the frame 410 at horizontal line 473 is 26-27 mm. The distance L2 between horizontal line 472 and horizontal line 473 is 5-6 mm. The diameter D4 of the frame 410 at horizontal line 474 is 23-24 mm. The distance L2 between horizontal line 473 and horizontal line 474 is 4-5 mm. The diameter D5 of the frame 410 at horizontal line 475 is 22-23 mm. The distance L4 between horizontal line 474 and horizontal line 475 is 4-5 mm. The diameter D6 of the frame 410 at horizontal line 476 is 23-24 mm. The distance L5 between horizontal line 475 and horizontal line 476 is 5-6 mm. The diameter D7 of the frame 410 at horizontal line 477 is 27-28 mm. The distance L6 between horizontal line 476 and horizontal line 477 is 4-5 mm. The diameter D8 of the frame 410 at horizontal line 478 is 31-32 mm. The distance L7 between horizontal line 477 and horizontal line 478 is 4-5 mm. The diameter D9 of the frame 410 at horizontal like 479 is 33-34 mm. The distance L8 between horizontal line 478 and horizontal line 479 is 5-6 mm. The diameter D10 of the frame 410 at horizontal line 480 is 31-32 mm. The distance L9 between horizontal line 479 and horizontal line 480 is 5-6 mm. The total height H1 of the frame 410, measured from the inflow end 440 to the outflow end 450, is 43-44 mm.

As described above, adjoining pairs of valve leaflets are attached to one another at their lateral ends to form leaflet commissures of a valve component. Each leaflet commissure is attached, by stitching or sutures, to a commissure post or commissure cell of a frame. FIGS. 22A-22J show an exemplary method of suturing a leaflet commissure to a commissure post of a frame. This method may be used, for example, to attach a leaflet commissure to one of commissure posts 219, 319, 419 of frames 210, 310, 410, respectively, as described in embodiments herein. In the exemplary method, a suture 2290 is being utilized to attach a leaflet commissure (not shown) to a commissure post 2219. The commissure post 2219 includes two holes 2292A, 2292B formed therethrough for attaching the leaflet commissure therethrough, but the number of holes may vary according to the height of the commissure post. The hole 2292A is closer to a first or inflow end 2291A of the commissure post 2219, and the hole 2292B is closer to a second or outflow end 2291B of the commissure post 2219. The suture 2290 may be an integral extension of a suture being utilized to attach the bases of the valve leaflets to a skirt and/or the frame, along a margin of attachment thereof. The suture 2290 may be an integral extension of the margin of attachment suture adjacent to a left side of the commissure post 2219. Although not shown, it will be understood by one of ordinary skill in the art that a needle is utilized to pass the suture 2290 through the leaflet commissure as well as through the holes 2292A, 2292B of the commissure post 2219.

Figure 22A:
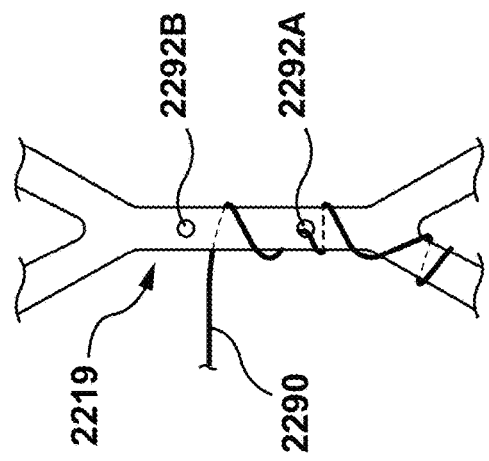
FIGS. 22A-22J show a method of attaching a valve component to a commissure post by means of sutures according to embodiments hereof.
Figure 22B:
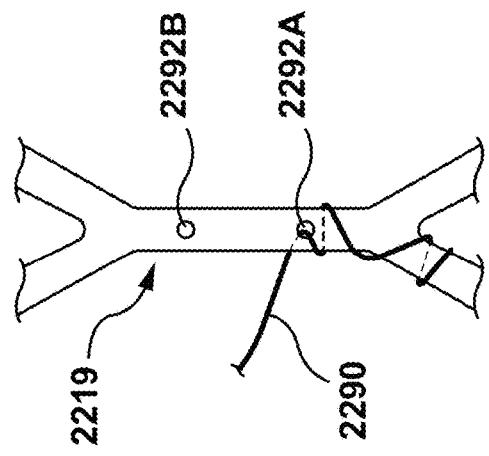
Figure 22C:
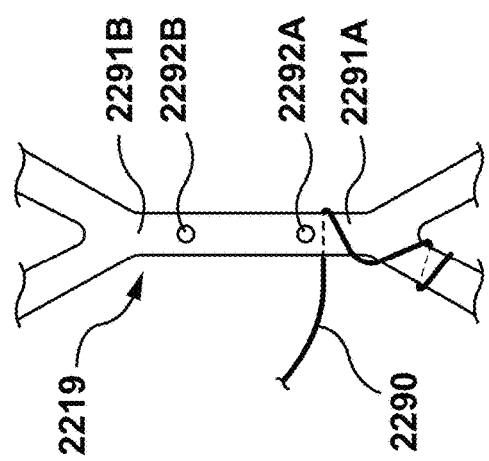
Figure 22D:
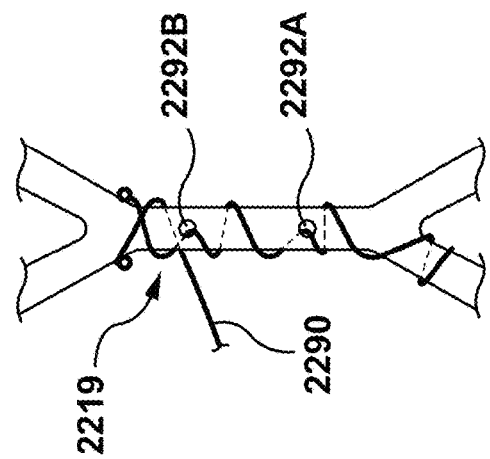
Figure 22E:
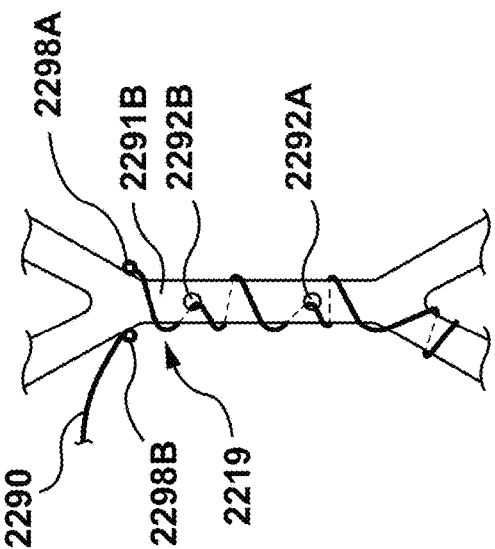
Figure 22F:
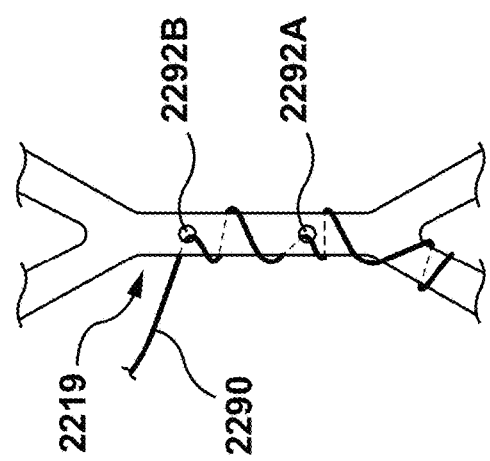
Figure 22G:
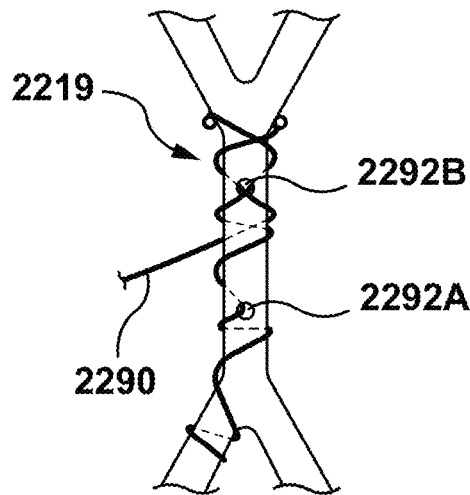
Figure 22H:
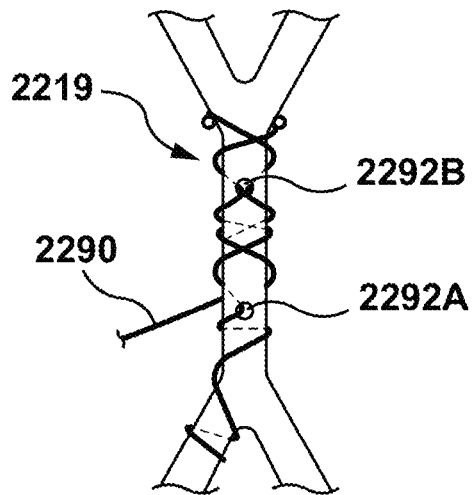
Figure 22I:
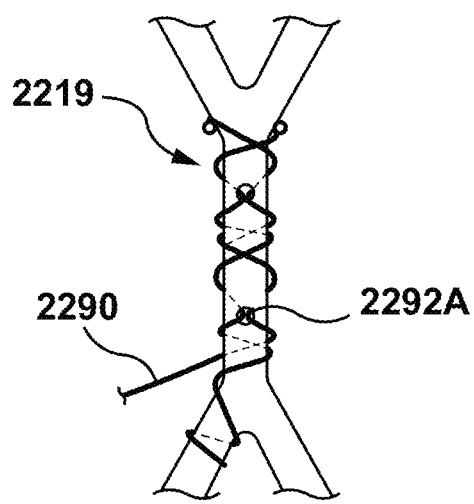

The suturing process initially proceeds from the inflow end 2291A of the commissure post 2219 to the outflow end 2291B of the commissure post 2219. In a first step illustrated in FIG. 22A, at a longitudinal position below or distal to the first hole 2292A, the suture 2290 is positioned around a full perimeter of the inflow end 2291A of the commissure post 2219. In the embodiment shown, the suture 2290 approaches the commissure post 2219 from a left side thereof. In a second step illustrated in FIG. 22B, the suture 2290 is positioned through the leaflet commissure, through the first hole 2292A, and back through the leaflet commissure. In a third step illustrated in FIG. 22C, at a longitudinal position between the first and second holes 2292A, 2292B, the suture 2290 is positioned around a full perimeter of the commissure post 2219. In a fourth step illustrated in FIG. 22D, the suture 2290 is positioned through the leaflet commissure, through the second hole 2292B, and back through the leaflet commissure. In a fifth step illustrated in FIG. 22E, at a longitudinal position above or proximal to the second hole 2292B, the suture 2290 is positioned around a full perimeter of the outflow end 2291B of the commissure post 2219. Further, as shown in FIG. 22E, a first locking knot 2298A is positioned on a right side of the commissure post 2219, adjacent to the outflow end 2291B, and a second locking knot 2298B is positioned on a left side of the commissure post 2219, adjacent to the outflow end 2291A and opposing the first locking knot 2298A. The first and second locking knots 2298A, 2298B prevent the leaflet commissure from sliding down due to repeated back pressure applied thereto during valve functioning in situ.

Figure 22J:
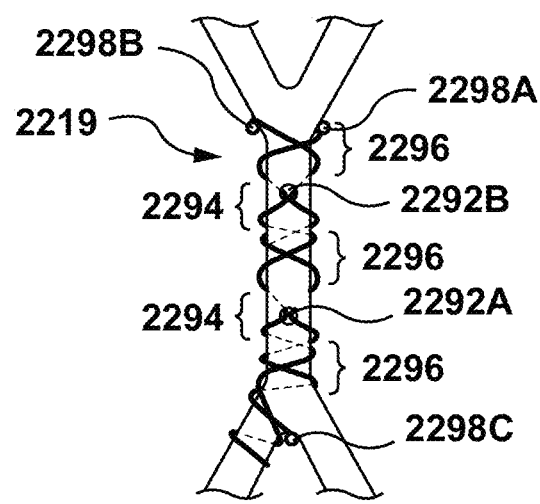

After the first and second locking knots 2298A, 2298B are in place, the suturing process continues from the outflow end 2291B of the commissure post 2219 to the inflow end 2291A of the commissure post 2219. In a sixth step illustrated in FIG. 22F, at a longitudinal position above or proximal to the second hole 2292B, the suture 2290 is positioned around a full perimeter of the outflow end 2291B of the commissure post 2219. At this stage, an "X" pattern of suture 2290 is thereby created at a longitudinal position above or proximal to the second hole 2292B. In a seventh step illustrated in FIG. 22G, the suture 2290 is positioned through the leaflet commissure, through the second hole 2292B, and back through the leaflet commissure. At this stage, an inverted "V" pattern of suture 2290 is thereby created at the second hole 2292B. In an eighth step illustrated in FIG. 22H, at a longitudinal position between the first and second holes 2292A, 2292B, the suture 2290 is positioned around a full perimeter of the outflow end 2291B of the commissure post 2219. At this stage, an "X" pattern of suture 2290 is thereby created at a longitudinal position between the first and second holes 2292A, 2292B. In a ninth step illustrated in FIG. 22I, the suture 2290 is positioned through the leaflet commissure, through the first hole 2292A, and back through the leaflet commissure. At this stage, an inverted "V" pattern of suture 2290 is thereby created at the first hole 2292A. In a tenth step illustrated in FIG. 22J, at a longitudinal position below or distal to the first hole 2292A, the suture 2290 is positioned around a full perimeter of the inflow end 2291A of the commissure post 2219. At this stage, an "X" pattern of suture 2290 is thereby created at a longitudinal position below or distal to the first hole 2292A. Further, as shown in FIG. 22J, a third locking knot 2298C is positioned below or distal to the inflow end 2291A of the commissure post 2219. This suturing method thus results in a plurality of "X" suture patterns 2296 and a plurality of inverted "V" suture patterns 2294, with the inverted "V" suture pattern 2294 being disposed between a pair of adjacent "X" suture patterns 2296 in an alternating manner. Each inverted "V" suture pattern 2294 is disposed at a hole of the commissure post 2219, and each "X" suture pattern 2296 is disposed above, below, or in between the holes of the commissure post 2219.

After the leaflet commissure is attached to the commissure post 2219, it may be desirable to attach a tissue covering or bumper thereover to ensure that the commissure post 2219 is atraumatic. Using a tissue covering or bumper to cover the commissure post 2219 shields or covers the suture 2290 which attaches the leaflet commissure to the commissure post 2219, thereby protecting or securing the attachment between the leaflet commissure to the commissure post 2219. FIGS. 23A-23L illustrate a method of attaching a tissue covering or bumper 2382 to the commissure post 2219. This method may be used, for example, to attach a tissue covering or bumper to one of commissure posts 219, 319, 419 of frames 230, 330, 430, respectively, as described in embodiments herein. In the exemplary method, a suture 2390 is being utilized to the tissue bumper 2382 to the commissure post 2219. The suture 2390 may be an integral extension of a suture being utilized to attach the bases of the valve leaflets to a skirt and/or the frame, along a margin of attachment thereof. The suture 2390 may be an integral extension of the margin of attachment suture adjacent to a right side of the commissure post 2219. Although not shown, it will be understood by one of ordinary skill in the art that a needle is utilized to pass the suture 2390 through the leaflet commissure and through the tissue bumper 2382.

Figure 23A:
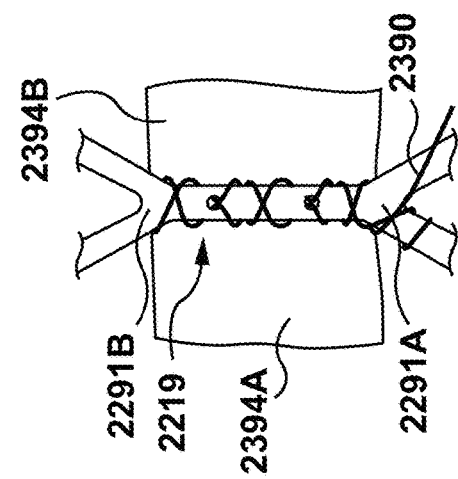
FIGS. 23A-23L show another method of attaching a valve component to a commissure post by means of sutures according to embodiments hereof.
Figure 23B:
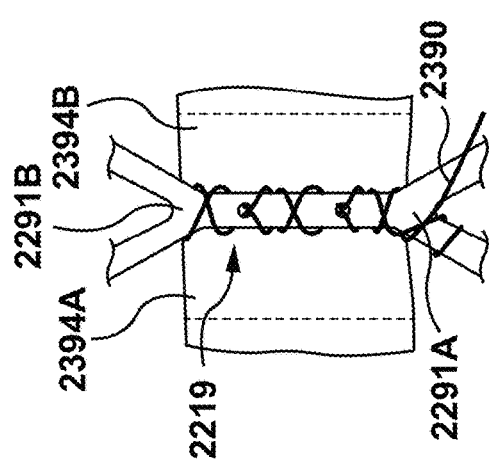
Figure 23C:
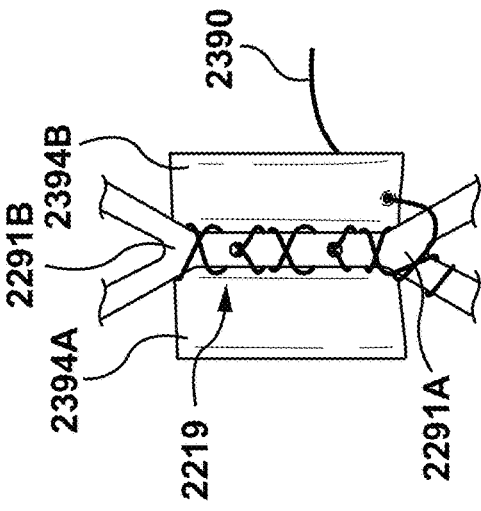
Figure 23D:
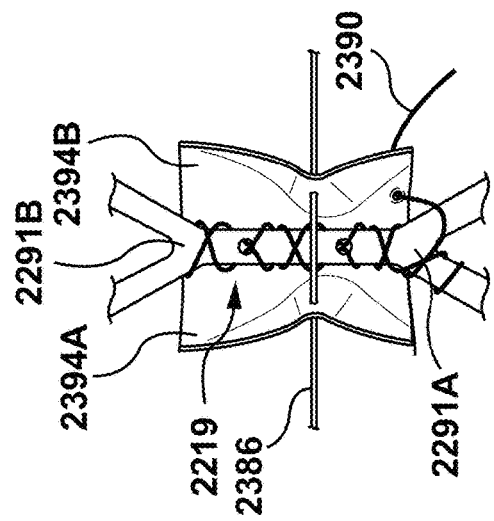
Figure 23E:
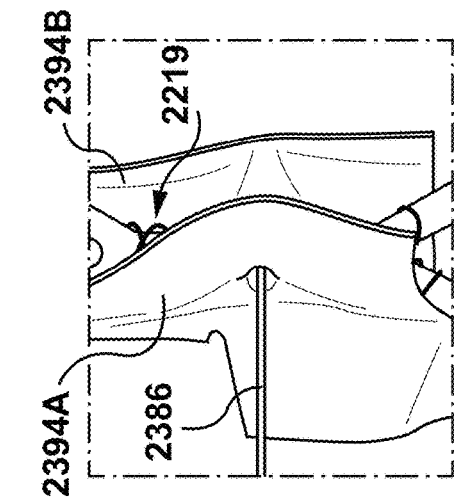

With reference to FIGS. 23A-23B, a strip of tissue material including tissue portions 2384A, 2384B are disposed underneath the commissure post 2219 and extend in opposing directions. Each tissue portion 2384A, 2384B is trimmed to leave enough tissue to cover the commissure post 2219 when folded thereover. For example, each tissue portion 2384A, 2384B may be trimmed along the dotted lines depicted on FIG. 23B. The suturing process initially proceeds from the inflow end 2291A of the commissure post 2219 to the outflow end 2291B of the commissure post 2219. In the embodiment shown, the suture 2390 approaches the commissure post 2219 from a right side thereof. As shown in FIG. 23C, the suture 2390 is positioned through the tissue portion 2384B. With reference to FIG. 23D and FIG. 23E (which is a side view of FIG. 23D), the tissue portions 2384A, 2384B are folded over the commissure post 2219 and a needle 2386 may be utilized to hold the folded positioned thereof.

Figure 23F:
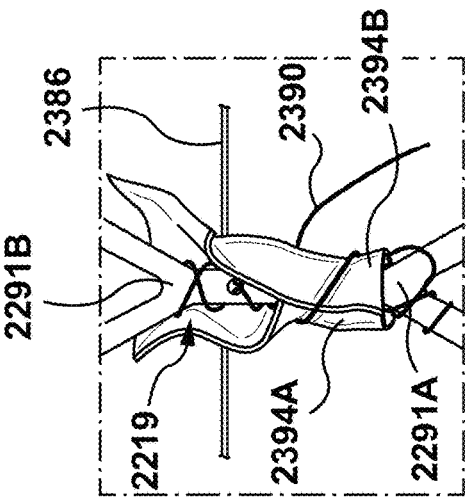

As shown in FIG. 23F, near the inflow end 2291A of the commissure post 2219, the suture 2390 is positioned around a full perimeter of the tissue portions 2384A, 2384B which are folded over the commissure post 2219. The needle 2386 may be repositioned closer to the outflow end 2291B of the commissure post 2219 at this stage, as shown in FIG. 23F.

Figure 23G:
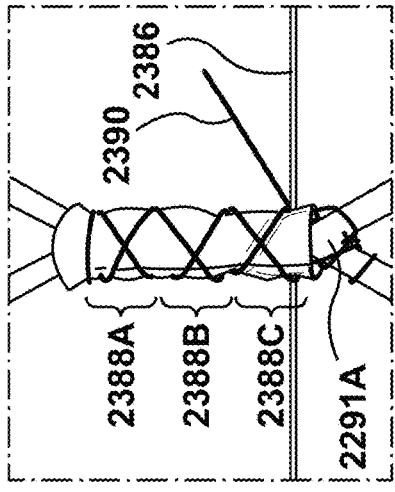

As shown in FIG. 23G, the suture 2390 is wound around the full perimeter of the tissue portions 2384A, 2384B which are folded over the commissure post 2219 until the suture 2390 is near the outflow end 2291B of the commissure post 2219. The suture 2390 is then positioned back towards the inflow end 2291A of the commissure post 2219, thereby creating a first "X" pattern 2388A of suture 2390 at a longitudinal position near the outflow end 2291B of the commissure post 2219 as shown in FIG. 23G. In addition, the needle 2386 may be repositioned closer to the inflow end 2291A of the commissure post 2219 at this stage, as shown in FIG. 23G relative to FIG. 23F.

Figure 23H:
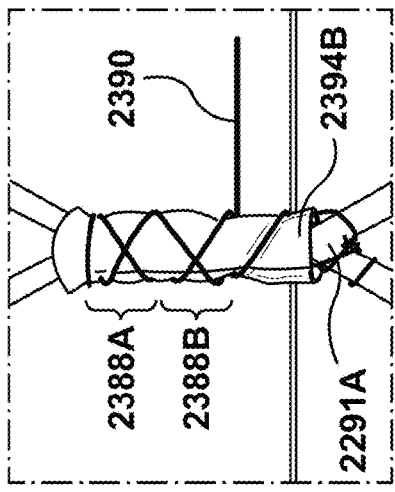
Figure 23I:
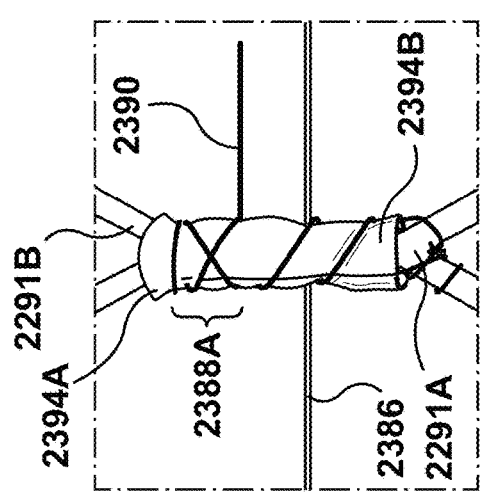

Wrapping of the suture 2390 continues towards the inflow end 2291A of the commissure post 2219, thereby creating a second "X" pattern 2388B of suture 2390 as shown in FIG. 23H. In addition, the needle 2386 may be repositioned closer to the inflow end 2291A of the commissure post 2219 at this stage, as shown in FIG. 23H relative to FIG. 23G. Wrapping of the suture 2390 continues towards the inflow end 2291A of the commissure post 2219, thereby creating a third "X" pattern 2388C of suture 2390 as shown in FIG. 23I. The needle 2386 is removed after the third "X" pattern is formed. The suture 2390 also may be attached directly to the leaflet commissure, which is attached to the commissure post 2219 via the suture 2290. As the suture 2390 is wrapped around the perimeter of the commissure post 2219, the suture 2390 also passes through the leaflet commissure. The suture 2390 may pass through the leaflet commissure via the same holes as suture 2290 in order to minimize the number of holes within the leaflet commissure.

Figure 23J:
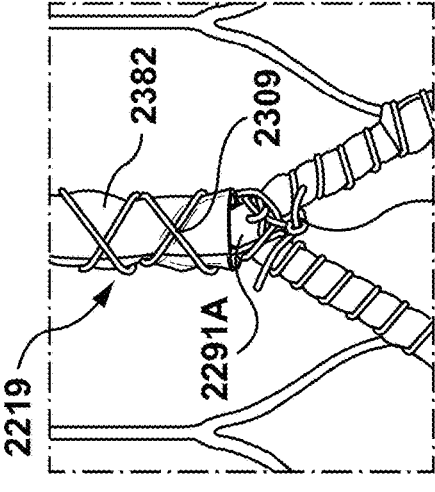
Figure 23K:
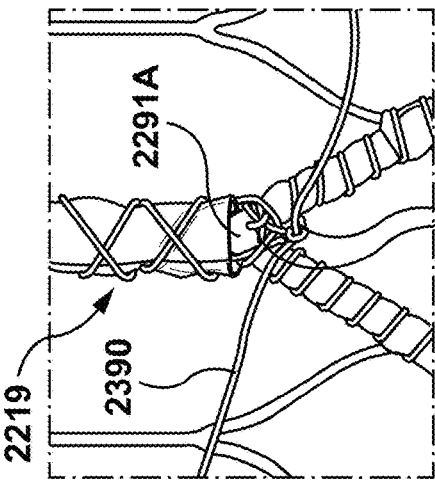
Figure 23L:
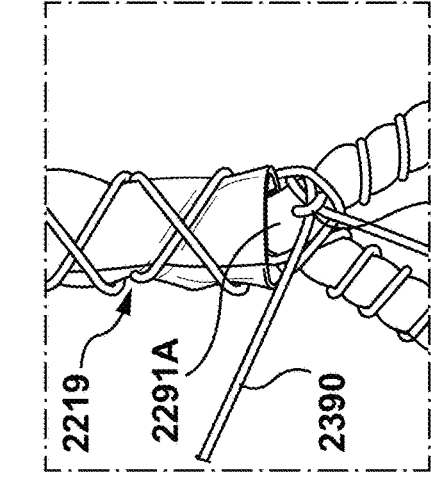

With reference to FIGS. 23J and 23K, a pair of double square knots 2389 are positioned below or distal to the inflow end 2291A of the commissure post 2219 to secure the folded tissue portions 2384A, 2384B to the commissure post 2219. As shown in FIG. 23L, after the folded tissue portions 2384A, 2384B are secured to the commissure post 2219, the folded tissue portions 2384A, 2384B may be considered to create or define a circumferential tissue bumper 2382.

Any of the frames described above may also include a window or a conduction protection cell which is oriented to align with a portion of the conduction system of the heart to reduce conduction disturbances to the anatomy. As described in more detail herein, a conduction protection cell is a relatively enlarged cell (enlarged relative to the cells directly adjacent thereto) which is disposed at the inflow end of the frame and is defined by crowns and struts of the inflow end of the frame. As described in more detail herein, a window is disposed at the inflow end of the frame and creates a circumferential gap along the inflow end of the frame that does not include any crowns or struts of the frame.

Figures 24, 25A:
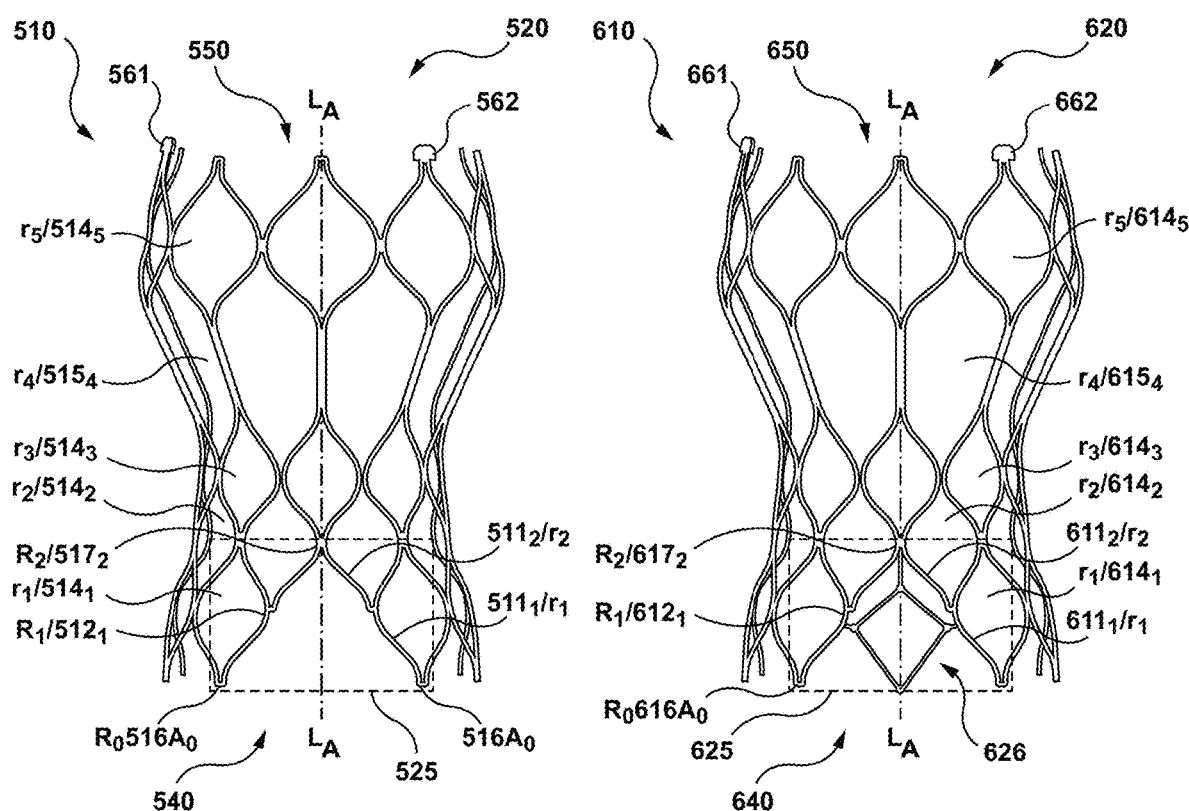
FIG. 24 depicts a perspective side view of a frame of a transcatheter aortic valve prosthesis according to another embodiment hereof, wherein the transcatheter aortic valve prosthesis includes a window at an inflow end of the prosthesis.
FIG. 25A depicts a side view of the frame of the transcatheter aortic valve prosthesis of FIG. 24, wherein the frame further includes a frame support section disposed within the window of the frame according to embodiments hereof.

FIG. 24 depicts a transcatheter aortic valve prosthesis 500 that includes a window 525 at the inflow end thereof. The frame 510 of the transcatheter aortic valve prosthesis 500 is the same as the frame 210 described above except that the frame 510 includes the window 525. As described above with respect to the frame 210, the frame 510 of the transcatheter aortic valve prosthesis 500 includes a plurality of struts 511 that are arranged to form a plurality of cells arranged circumferentially around a longitudinal axis $L_A$ of the transcatheter aortic valve prosthesis 500 and longitudinally to form a tubular structure. The struts 511 are defined herein as the elongated wire segments of the frame 510. The plurality of cells include a plurality of first cells 514 and one or more access cells 515, and the one or more access cells 515 each have an enlarged area relative or compared to the first cells 514. As described above with respect to the access cells 215, the access cells 515 are enlarged cells configured to provide improved access to a patient's percutaneous coronary arteries in situ if a percutaneous coronary intervention procedure is required post-implantation of transcatheter aortic valve prosthesis 500. A valve component (not shown in FIG. 24) is disposed within a central lumen 520 of the frame 510, and the valve component is attached to the frame 510. The valve component may be the same as the valve component 230. The frame 510 secures the transcatheter aortic valve prosthesis 500 in place in situ within the vasculature of the patient.

In this embodiment, unlike the frame 210, the frame 510 of the transcatheter aortic valve prosthesis 500 further includes the window 525 disposed at the inflow end 540 of the frame 510. When the transcatheter aortic valve prosthesis 500 is deployed in situ, the window 525 is positioned to align with a portion of the conduction system of the heart. For example, the window 525 may be aligned with the left bundle branch of the heart when the transcatheter aortic valve prosthesis 500 is deployed in situ. Due to the presence of the window 525, the outward radial force exerted by the frame 510 of the transcatheter aortic valve prosthesis 500 on the left bundle branch is reduced as compared to a frame that does not include a window 525. Thus, the frame 510 of the transcatheter aortic valve prosthesis 500 is less likely to negatively impact the conduction system of the heart.

The window 525 is disposed within rows $r_1$ of first cells $514_1$ and $r_2$ of first cells $514_2$, while the row $r_4$ of access cells $515_4$ is disposed between the row $r_3$ of first cells $514_3$ and the row $r_5$ of first cells $514_5$ of the frame 510 such that row $r_3$ of first cells $514_3$ are disposed between the window 525 and the row $r_4$ of access cells $515_4$. The window 525 is disposed at the inflow end 540 of the frame 510 and the row $r_4$ of access cells $515_4$ is disposed closer to the outflow end 550 of the frame 510. The window 525 is enclosed by two inflow crowns $516A_0$ in the row $R_0$, two struts $511_1$ in the row $r_1$, two tri-strut connections $512_1$ in the row $R_1$, two struts $511_2$ in the row $r_2$, and one node $517_2$ in the row $R_2$. In some embodiments, the window 525 can measure approximately 60° degrees of a circumference of the frame 510.

In this embodiment, the area of the window 525 is approximately equivalent to the area of two first cells 514 combined, specifically the first cells 514 directly adjacent to the window 525 at the inflow end 540 of the frame 510. Stated another way, the area of the window 525 compared to the area of a first cell 514 directly adjacent to the window 525 at the inflow end 540 of the frame 510 is approximately a 2:1 ratio. In other words, a first cell 514 directly adjacent to the window 525 at the inflow end 540 of the frame 510 has an area that is approximately 50% of an area of the window 525 of the frame 510, with "approximately" including a tolerance of 5%. In another embodiment, a first cell 514 adjacent to at least one of the windows 525 has an area that is between 48% and 52% of an area of one of the windows 525 of the frame 510. In this embodiment, the area of the window 525 is between 114-116 mm$^2$ and the area of a first cell 514 is between 57-58 mm$^2$.

Figure 25B:
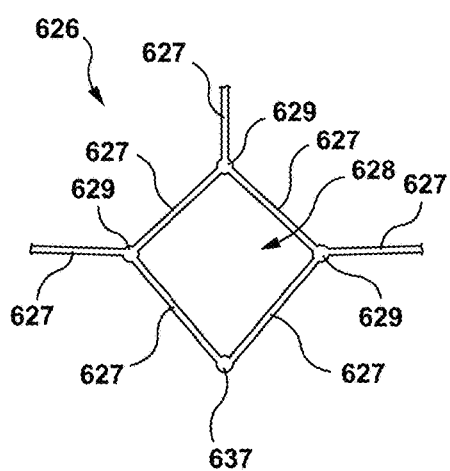
FIG. 25B depicts a close-up view of the frame support section of the transcatheter aortic valve prosthesis of FIG. 25A.

FIGS. 25A-25B depict an embodiment of a transcatheter aortic valve prosthesis 600 that includes a frame 610 having a window 625 and a frame support section 626. The frame 610 of the transcatheter aortic valve prosthesis 600 is the same as the frame 510 described above except that the frame 610 includes the frame support section 626. The frame support section 626 is attached to the frame 610 and is disposed within the window 625 to support the circumferential gap created by the window 625. The frame support section 626 is formed from a polymeric material or a fabric material while the frame 610 is formed from stainless steel or a nickel titanium alloy.

As described above with respect to the frames 210, 510, the frame 610 of the transcatheter aortic valve prosthesis 600 includes a plurality of struts 611 that are arranged to form a plurality of cells arranged circumferentially around a longitudinal axis $L_4$ of the transcatheter aortic valve prosthesis 600 and longitudinally to form a tubular structure. The struts 611 are defined herein as the elongated wire segments of the frame 610. The plurality of cells include a plurality of first cells 614 and one or more access cells 615. The one or more access cells 615 each have an enlarged area relative or compared to the first cells 614. As described above with respect to the access cells 215, 515, the access cells 615 are enlarged cells configured to provide improved access to a patient's percutaneous coronary arteries if a percutaneous coronary intervention procedure is required post-implantation of transcatheter aortic valve prosthesis 600. A valve component (not shown in FIG. 25A) is disposed within a central lumen 620 of the frame 610, and the valve component is attached to the frame 610. The valve component may be the same as the valve component 230. The frame 610 secures the transcatheter aortic valve prosthesis 600 in place in situ within the vasculature of the patient.

The frame 610 of the transcatheter aortic valve prosthesis 600 includes the window 625, which is the same as the window 525 described above. The window 625 is disposed at the inflow end 640 of the frame 610. When the transcatheter aortic valve prosthesis 600 is deployed in situ, the window 625 is positioned to align with a portion of the conduction system of the heart. For example, the window 625 may be aligned with the left bundle branch of the heart when the transcatheter aortic valve prosthesis 600 is deployed in situ. Due to the presence of the window 625, the outward radial force exerted by the frame 610 of the transcatheter aortic valve prosthesis 600 on the left bundle branch is reduced as compared to a frame that does not include a window 625. Thus, the frame 610 of the transcatheter aortic valve prosthesis 600 is less likely to negatively impact the conduction system of the heart.

The window 625 is disposed within rows $r_1$ of first cells $614_1$ and $r_2$ of first cells $614_2$, while the row $r_4$ of access cells $615_4$ is disposed between the row $r_3$ of first cells $614_3$ and the row $r_5$ of first cells $614_5$ of the frame 610 such that row $r_3$ of first cells $614_3$ are disposed between the window 625 and the row $r_4$ of access cells $615_4$. The window 625 is disposed at the inflow end 640 of the frame 610 and the row $r_4$ of access cells $615_4$ is disposed closer to the outflow end 650 of the frame 610. The window 625 is enclosed by two inflow crowns $616A_0$ in the row $R_0$, two struts $611_1$ in the row $r_1$, two tri-strut connections $612_1$ in the row $R_1$, two struts $611_2$ in the row $r_2$, and one node $617_2$ in the row $R_2$. The window 625 can measure approximately 60° degrees of a circumference of the frame 610.

In this embodiment, the area of the window 625 is approximately equivalent to the area of two first cells 614 combined, specifically the first cells 614 directly adjacent to the window 625 at the inflow end 640 of the frame 610. Stated another way, the area of the window 625 compared to the area of a first cell 614 directly adjacent to the window 625 at the inflow end 640 of the frame 610 is approximately a 2:1 ratio. In other words, a first cell 614 directly adjacent to the window 625 at the inflow end 640 of the frame 610 has an area that is approximately 50% of an area of the window 625 of the frame 610, with "approximately" including a tolerance of 5%. In another embodiment, a first cell 614 adjacent to at least one of the window 625 has an area that is between 48% and 52% of an area of one of the windows 625 of the frame 610. The area of the window 625 may be between 114-116 mm² and the area of a first cell 614 is between 57-58 mm².

In this embodiment, the frame 610 of the transcatheter aortic valve prosthesis 600 further includes the frame support section 626 disposed within the window 625 as mentioned above. As best shown in FIG. 25B, the frame support section 626 includes a plurality of polymeric or fabric segments 627. Four segments 627 come together to form a substantially diamond-shaped polymeric or fabric cell 628 in the window 625. The area of the polymeric or fabric cell 628 is approximately equivalent to the area of two first cells 614 combined, specifically a first cell 614 disposed directly adjacent to the window 625 nearest the inflow end 640 of the frame 610. Stated another way, the area of the polymeric or fabric cell 628 compared to the area of a first cell 614 adjacent to the window 625 nearest the inflow end 640 may be approximately a 2:1 ratio. In other words, a first cell 614 adjacent to the window 625 nearest the inflow end 640 has an area that may be approximately 50% of an area of the polymeric or fabric cell 628 of the frame 610, as shown best in FIGS. 25A-25B. The area of the polymeric or fabric cell 628 may be between 50-115 mm² and the area of a first cell 614 is between 57-58 mm².

In alternate embodiments (not shown), the area of the polymeric or fabric cell 628 may be approximately equivalent to the area of one first cell 614, specifically a first cell 614 disposed directly adjacent to the window 625 nearest the inflow end 640 of the frame 610. Stated another way, the area of the polymeric or fabric cell 628 compared to the area of a first cell 614 adjacent to the window 625 nearest the inflow end 640 may be approximately a 1:1 ratio. The three remaining polymeric or fabric segments 627 attach the polymeric or fabric cell 628 of the frame support section 626 to the frame 610 of the transcatheter aortic valve prosthesis 600 by forming three polymeric or fabric tri-strut connections 629. The frame support section 626 attaches to the frame 610 at two tri-strut connections $612_1$ in the row $R_1$ and at one node $617_2$ in the row $R_2$ of the frame 610. As can be seen in FIG. 25B, two of the polymeric or fabric segments 627 come together to form a polymeric or fabric crown 637 disposed at the inflow end 640 of the frame 610 which is longitudinally aligned with remaining crowns at the inflow end of the frame.

The frame support section 626 is configured to support, or fill in, the circumferential gap made by the window 625 of the frame 610 at the inflow end 640 such that the frame 610 circumferentially seals within the anatomy. When the frame 610 has a circumferential seal against the vessel wall, the skirt of the valve component (which is attached to the frame 610) is sealed against the anatomy to prevent paravalvular leakage. The frame support section 626 has a reduced radial force compared to the radial force of the frame 610 of the transcatheter aortic valve prosthesis 600 due to its material composition. When the transcatheter aortic valve prosthesis 600 is deployed in situ, the frame support section 626 is positioned to align with a portion of the conduction system of the heart. For example, the frame support section 626 may be aligned with the left bundle branch of the heart when the transcatheter aortic valve prosthesis 600 is deployed in situ. Due to the presence of the frame support section 626, the outward radial force exerted by the frame 610 of the transcatheter aortic valve prosthesis 600 on the left bundle branch is reduced as compared to a frame that does not include a window 625 with a frame support section 626. Thus, the frame 610 of the transcatheter aortic valve prosthesis 600 is less likely to negatively impact the conduction system of the heart.

Figure 26:
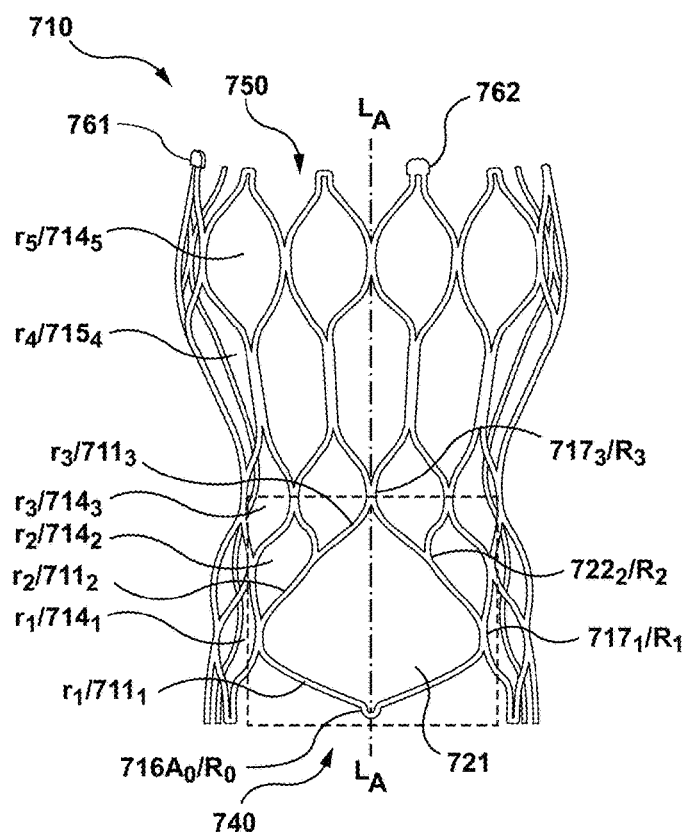
FIG. 26 depicts a perspective side view of a frame of a transcatheter aortic valve prosthesis according to another embodiment hereof, wherein the transcatheter aortic valve prosthesis includes one access cell at an inflow end of the prosthesis.

FIG. 26 depicts a transcatheter aortic valve prosthesis 700 that includes a conduction protection cell 721 disposed at an inflow end 740 thereof. The frame 710 of the transcatheter aortic valve prosthesis 700 is the same as the frame 210 described above, except that the frame 710 includes the conduction protection cell 721.

As described above with respect to the frame 210, the frame 710 of the transcatheter aortic valve prosthesis 700 includes a plurality of struts 711 that are arranged to form a plurality of cells arranged circumferentially around a longitudinal axis $L_A$ of the transcatheter aortic valve prosthesis 700 and longitudinally to form a tubular structure. The struts 711 are defined herein as the elongated wire segments of the frame 710. The plurality of cells include a plurality of first cells 714 and one or more access cells 715. The one or more access cells 715 each have an enlarged area relative or compared to the first cells 714. As described above with respect to the access cells 215, the access cells 715 are enlarged cells configured to provide improved access to a patient's percutaneous coronary arteries if a percutaneous coronary intervention procedure is required post-implantation of transcatheter aortic valve prosthesis 700. A valve component (not shown in FIG. 26) is disposed within a central lumen 720 of the frame 710, and the valve component is attached to the frame 710. The valve component may be the same as the valve component 230. The frame 710 secures the transcatheter aortic valve prosthesis 700 in place in situ within the vasculature of the patient.

The conduction protection cell 721 is enclosed by one inflow crown $716A_0$ in the row $R_0$, two struts $711_1$ in the row $r_1$, two nodes $717_1$ in the row $R_1$, two struts $711_2$ in the row $r_2$, two tri-strut connections $712_2$ in the row $R_2$, two struts $711_3$ in the row $r_3$, and one node $717_3$ in the row $R_3$. The area of the conduction protection cell 721 is approximately equivalent to the area of two first cells 714 combined, specifically the first cells 714 disposed directly adjacent to the conduction protection cell 721 nearest to the inflow end 740 of the frame 710. Stated another way, the area of the conduction protection cell 721 compared to the area of a first cell 714 adjacent to the conduction protection cell 721 nearest to the inflow end 740 is approximately a 2:1 ratio. In other words, a first cell 714 adjacent to the conduction protection cell 721 nearest the inflow end 740 has an area that is approximately 50% of an area of the conduction protection cell 721 of the frame 710, with "approximately" including a tolerance of 5%. In another embodiment, a first cell 714 adjacent to the conduction protection cell 721 has an area that is between 48% and 52% of an area of the conduction protection cell 721 of the frame 710. The area of the conduction protection cell 721 may be between 50-115 mm$^2$ and the area of a first cell 714 is between 57-58 mm$^2$.

In alternate embodiments (not shown), the area of the conduction protection cell 721 may be approximately equivalent to the area of one first cell 714, specifically the first cells 714 disposed directly adjacent to the conduction protection cell 721 nearest to the inflow end 740 of the frame 710. Stated another way, the area of the conduction protection cell 721 compared to the area of a first cell 714 adjacent to the conduction protection cell 721 nearest to the inflow end 740 may be approximately a 1:1 ratio. In other words, a first cell 714 adjacent to the conduction protection cell 721 nearest the inflow end 740 has an area that may be approximately 100% of an area of the conduction protection cell 721 of the frame 710.

The conduction protection cell 721 is disposed within rows $r_1$ of first cells $714_1$ to $r_3$ of first cells $714_3$, while the row $r_4$ of access cells $715_4$ is disposed between the row $r_3$ of first cells $714_3$ and the row $r_5$ of first cells $714_5$ of the frame 710 such that row $r_3$ of first cells $714_3$ is disposed between the conduction protection cell 721 and the row $r_4$ of access cells $715_4$. The conduction protection cell 721 is disposed at the inflow end 740 of the frame 710 and the row $r_4$ of access cells $715_4$ is disposed closer to the outflow end 750 of the frame 710 as compared to the conduction protection cell 721.

The conduction protection cell 721 is configured to support, or fill in, the circumferential gap of the frame 710 at the inflow end 740 such that the frame 710 circumferentially seals within the anatomy. When the frame 710 has a circumferential seal against the vessel wall, the skirt of the valve component (which is attached to the frame 710) is sealed against the anatomy to prevent paravalvular leakage. The conduction protection cell 721 has a reduced radial force at the inflow end compared to the radial force of a frame without a conduction protection cell 721 (i.e., the frame 210) because the conduction protection cell 721 has an area much larger than the area of the surrounding first cells 714. When the transcatheter aortic valve prosthesis 700 is deployed in situ, the conduction protection cell 721 is positioned to align with a portion of the conduction system of the heart. For example, the conduction protection cell 721 may be aligned with the left bundle branch of the heart when the transcatheter aortic valve prosthesis 700 is deployed in situ. Due to the presence of the conduction protection cell 721, the outward radial force exerted by the frame 710 of the transcatheter aortic valve prosthesis 700 on the left bundle branch is reduced as compared to a frame that does not include a conduction protection cell 721. Thus, the frame 710 of the transcatheter aortic valve prosthesis 700 is less likely to negatively impact the conduction system of the heart.

In another embodiment hereof, rather than a conduction protection cell or a window, any frame described herein may include non-flared struts that are positioned to align in situ with a portion of the conduction system of the heart to reduce conduction disturbances to the anatomy. More particularly, at the inflow end of the frame, the frame includes a row of struts that includes standard struts and non-flared struts. Each standard strut flares radially outward when the frame is in an expanded configuration and each non-flared strut of the plurality of non-flared struts does not flare radially outward when the frame is in the expanded configuration. Each non-flared strut bends or extends radially inwards as compared to each standard strut. The crowns disposed between a pair of non-flared struts at the inflow end are disposed radially inward relative to crowns disposed between a pair of standard struts. Each non-flared strut bends or extends radially inwards as compared to each standard strut.

Figures 27A, 27B, 27C:
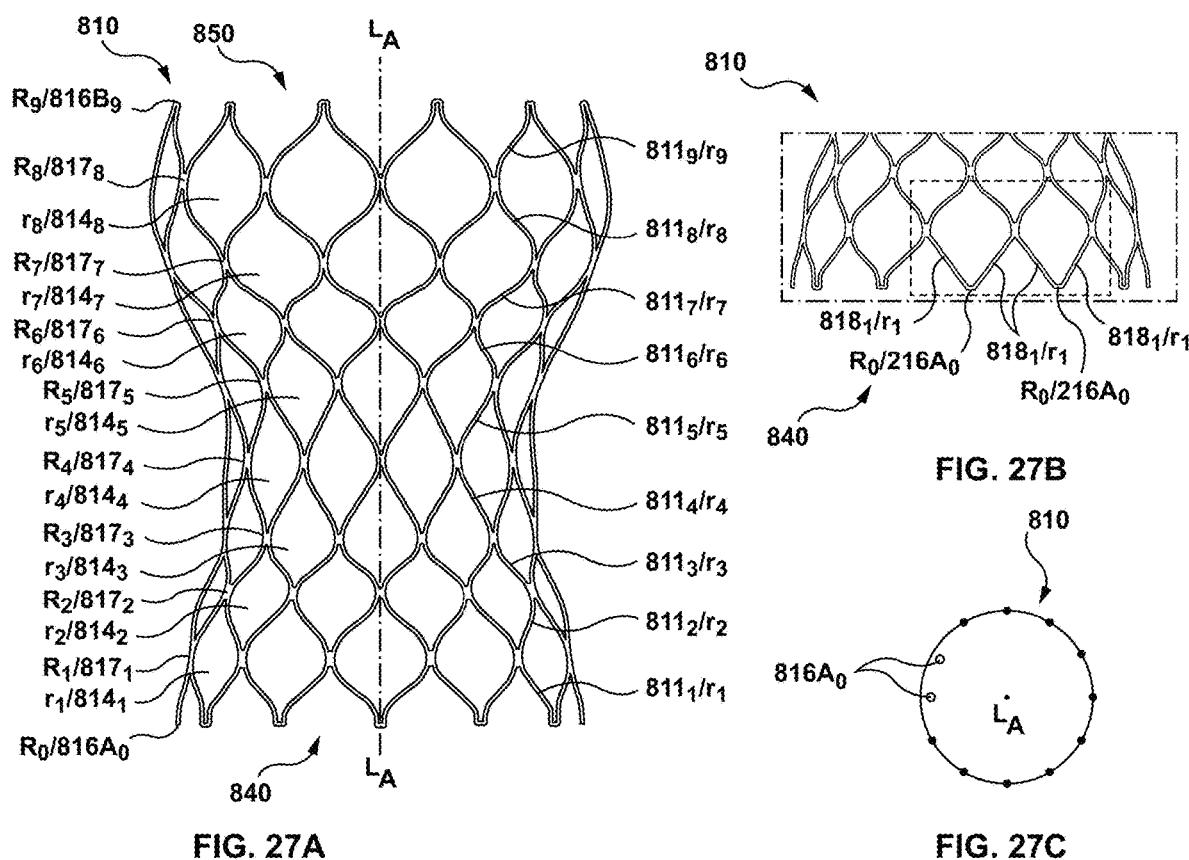
FIG. 27A depicts a side view of a frame of a transcatheter aortic valve prosthesis according to another embodiment hereof, wherein the frame includes four non-flared struts.
FIG. 27B depicts a close up view of non-flared struts of the frame of the transcatheter aortic valve prosthesis of FIG. 27A.
FIG. 27C depicts a bottom view of the frame of the transcatheter aortic valve prosthesis of FIG. 27A.

More particularly, FIGS. 27A-27C depict an embodiment of a transcatheter aortic valve prosthesis 800 that includes one or more non-flared struts 818. More particularly, FIG. 27A depicts a frame 810 of the transcatheter aortic valve prosthesis 800. The frame 810 of the transcatheter aortic valve prosthesis 800 includes an inflow end 840 and an outflow end 850. The frame 810 of the transcatheter aortic valve prosthesis 800 includes a plurality of struts 811 that are arranged to form a plurality of cells arranged circumferentially around a longitudinal axis $L_A$ of the transcatheter aortic valve prosthesis 800 and longitudinally to form a tubular structure. The struts 811 are defined herein as the elongated wire segments of the frame 810, as can be seen in FIG. 27A. A valve component (not shown in FIG. 27A) is disposed within a central lumen of the frame 810, and the valve component is attached to the frame 810. The valve component may be the same as the valve component 130. The frame 810 secures the transcatheter aortic valve prosthesis 800 in place in situ within the vasculature of the patient.

The plurality of struts 811 are arranged at the inflow end 840 of the frame 810 such that two adjacent struts 811 of the plurality of struts 811 come together to form a crown 816 at the inflow end 840. Thus, a row or plurality of inflow crowns 816A are formed at the inflow end 840 of the frame 810. As best shown in FIG. 27A, in this embodiment, the frame 810 includes exactly twelve inflow crowns 816A at the inflow end 840 of the frame 810, but this is not meant to be limiting. The inflow end 840 of the frame 810 also forms an end of the transcatheter aortic valve prosthesis 800. The plurality of the struts 811 are arranged at the outflow end 850 of the frame 810 such that two adjacent struts 811 of the plurality of struts 811 come together to form a crown 816 at the outflow end 850. Thus, the frame 810 includes exactly twelve outflow crowns 816B formed at the outflow end 850 of the frame 810, but this is not limiting. The outflow end 850 of the frame 810 also forms an end of the transcatheter aortic valve prosthesis 800. As described in more detail below, exactly four struts 811 come together to form a node 817. The cells 814, that will be described in further detail herein, are defined as the spaces between the plurality of struts 811, crowns 816, and nodes 817. The frame 810 is self-expanding and may be formed from any material described above with reference to the frame 110.

The frame 810 of the transcatheter aortic valve prosthesis 800 includes a plurality of cells 814 arranged circumferentially around the longitudinal axis $L_A$ of the transcatheter aortic valve prosthesis 800 and longitudinally to form a tubular structure, as shown in FIG. 27A. Each cell 814 of the plurality of first cells 814 is formed by exactly four struts 811 and exactly four nodes 817, or exactly three nodes 817 and exactly one crown 816, and is generally diamond-shaped. The plurality of cells 814 may vary in size depending on the position of the cell 814 within the frame 810, i.e., row placement and/or longitudinal position on the frame 810. For example, the plurality of cells 814 disposed near the inflow end 840 and the outflow end 850 of the frame 810 may be larger than the plurality of cells 814 disposed at a midline or midportion of the frame 810. The plurality of cells 814 disposed near the outflow end 850 of the frame 810 may be larger than the plurality of cells 814 disposed near the inflow end 840 of the frame 810.

The frame 810 of the transcatheter aortic valve prosthesis 800 is described herein for illustrative purposes in terms of horizontal rows of crowns 816 and nodes 817, and horizontal rows of struts 811 and cells 814. Each row of struts and cells is disposed between two adjacent rows of the crowns, nodes, and/or tri-strut connections. In FIG. 27A, subscripts have been added to the reference numerals for the crowns 816, nodes 817, struts 811, and cells 814 to indicate the row number of each type of frame component starting with the inflow end 840. The frame 810 includes rows of crowns 816 and nodes 817. Beginning at the inflow end 840 of the frame 810, row $R_0$ describes the row of inflow crowns $816A_0$ at the inflow end 840 of the frame 810. Disposed directly adjacent to the row $R_0$ of inflow crowns $816A_0$ is row $R_1$ of nodes $817_1$, and directly adjacent the row $R_1$ of nodes $817_1$ is row $R_2$ of nodes $817_2$. This naming convention for the nodes 817 continues up to the outflow end 850 of the frame 810 to the row $R_8$ of nodes $817_8$. Disposed directly adjacent the row $R_8$ of nodes $817_8$ is row $R_9$ of outflow crowns $816B_9$ at the outflow end 850 of the frame 810.

In the embodiment shown, the frame 810 can include a total of eight rows of cells 814 beginning at the inflow end 840 with the row $r_1$ of cells $814_1$, to the row $r_8$ of cells $814_8$ at the outflow end 850, as best shown in FIG. 27A. For example, the row $r_1$ of cells $814_1$ is disposed between the row $R_0$ of inflow crowns $816A_0$ and the row $R_2$ of nodes $817_2$. In particular, each cell $814_1$ in the row $r_1$ is defined by an inflow crown $816A_0$ in the row $R_0$, two struts $811_1$ in the row $r_1$, two nodes $817_1$ in the row $R_1$, two struts $811_2$ in the row $r_2$, and one node $817_2$ in the row $R_2$. The row $r_2$ of cells $814_2$ is disposed between the row $R_1$ of nodes $817_1$ and the row $R_3$ of nodes $817_3$, and the cells 814 thereof are defined the same as described above with respect to the row $814_1$ of cells 814. The naming convention for the cells 814 continues distally to the row $r_8$ of cells $814_8$ located at the outflow end 850 between the row $R_7$ of nodes $817_7$ and the row $R_9$ of outflow crowns $816B_9$.

The struts 811 are also numbered in rows beginning at the inflow end 840 of the frame 810, as shown in FIG. 27A. For example, the struts 811 that come together to form the inflow crowns $816A$ in the row $R_0$ at the inflow end 840 are denoted as row $r_1$ of struts $811_1$. The struts 811 in between the row $R_1$ of nodes $817_1$ and the row $R_2$ of nodes $817_2$ are denoted as row $r_2$ of struts $811_2$. This naming convention for the struts 811 continues distally to the outflow end 850 of the frame 810 to the row $r_9$ of struts $811_9$.

With reference to FIG. 27B and FIG. 27C, the frame 810 of the transcatheter aortic valve prosthesis 800 includes four adjacent non-flared struts 818 in the row $r_1$ (which collectively form two inflow crowns $816A_0$ in the row $R_0$). Each non-flared strut 818 has a vertically straight configuration as opposed to a standard or flared configuration. FIG. 27B depicts an enlarged view of a portion of the row $R_0$ which includes the non-flared struts 818. FIG. 27C depicts a bottom view of the inflow end 840 of the transcatheter aortic valve prosthesis 800. Each non-flared strut 818 bends or extends radially inwards as compared to each standard strut 811. As best shown on FIG. 27C, the two inflow crowns $816A_0$ formed from the four non-flared struts 818 are displaced radially inward from the circumference of the frame 810 outlined by the rest of the inflow crowns $816A_0$ in the row $R_0$. When the transcatheter aortic valve prosthesis 800 is deployed in situ, the non-flared struts 818 are positioned to align with a portion of the conduction system of the heart. For example, the non-flared struts 818 may be aligned with the left bundle branch of the heart when the transcatheter aortic valve prosthesis 800 is deployed in situ. Due to the presence of the non-flared struts 818, the outward radial force exerted by the frame 810 of the transcatheter aortic valve prosthesis 800 on the left bundle branch is reduced as compared to a frame that does not include non-flared struts 818. Thus, the frame 810 of the transcatheter aortic valve prosthesis 800 is less likely to negatively impact the conduction system of the heart.

Figure 28:
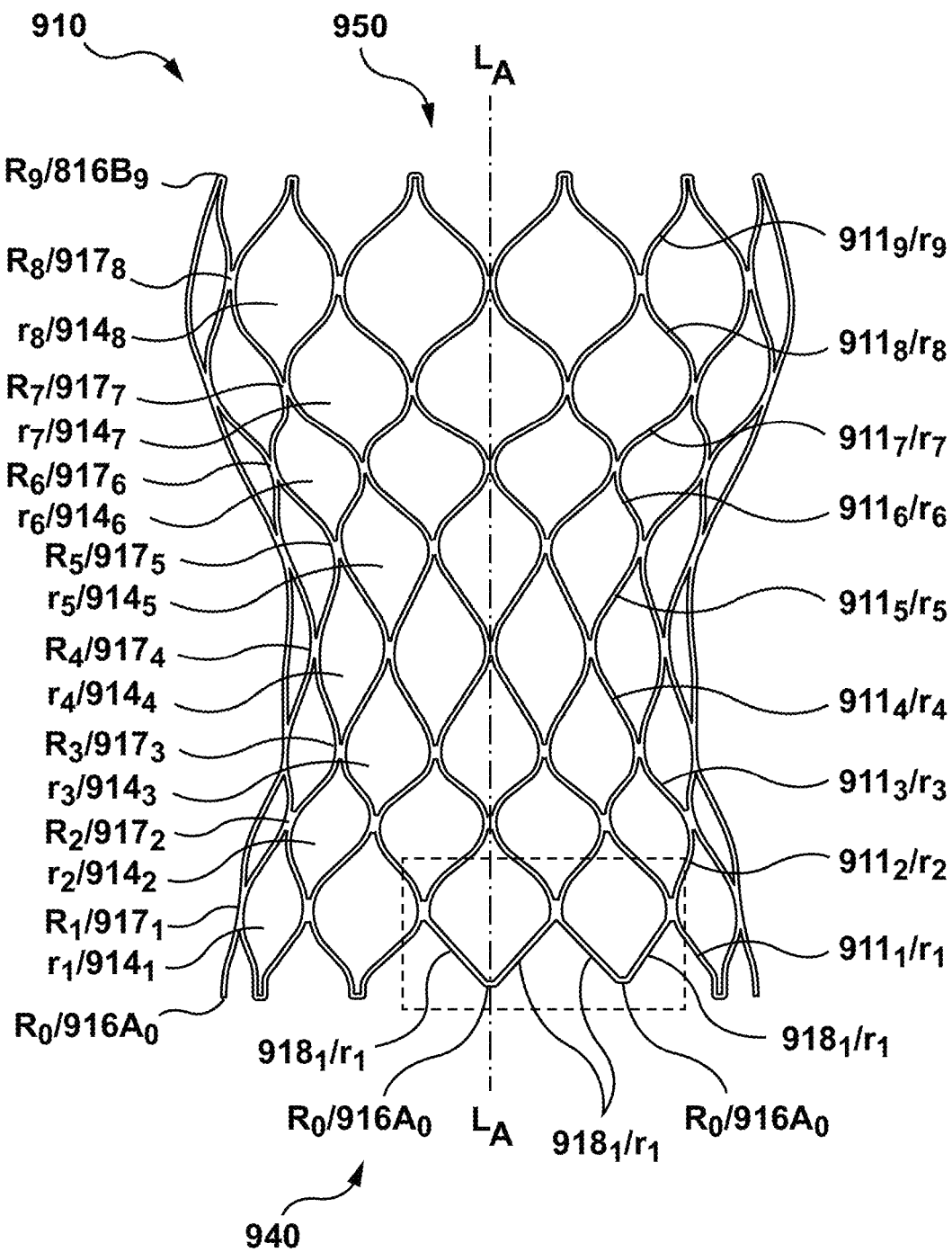
FIG. 28 depicts a side view of a frame of a transcatheter aortic valve prosthesis according to another embodiment hereof, wherein the frame includes four non-flared struts that have a shorter height than standard struts of a frame.

FIG. 28 depicts a transcatheter aortic valve prosthesis 900 that includes one or more non-flared struts 918 that have a shorter height than a height of standard struts 911. The frame 910 of the transcatheter aortic valve prosthesis 900 is the same as the frame 810 described above, except that the non-flared struts $918_1$ of the frame 910 have a shorter height than the non-flared struts 818 of the frame 810. The non-flared struts $918_1$ in the row $r_1$ have a vertically straight or non-flared configuration, as described above with respect to the non-flared struts 818. Each non-flared strut $918_1$ bends or extends radially inwards as compared to each standard strut 911. The two inflow crowns $916A_0$ formed from the four non-flared struts $918_1$ are displaced radially inward from the circumference of the frame 910 outlined by the rest of the inflow crowns $916A_0$ in the row $R_0$. Further, each of the non-flared struts $918_1$ have a shorter height than a height of struts $911_1$ in the row $r_1$. The non-flared struts $918_1$ may have a height that is 1-3 mm shorter than a height of struts $911_1$ in the row $r_1$. In an embodiment, the non-flared struts $918_1$ may have a height that is 5-15% shorter than a height of struts $911_1$ in the row $r_1$. Due to the shorter height thereof, the two inflow crowns $916A_O$ formed from the four non-flared struts $918_1$ are not longitudinally aligned with the remaining inflow crowns of the inflow end 940 of the frame 910. Rather, the two inflow crowns $916A_O$ formed from the four non-flared struts $918_1$ are disposed closer to the outflow end 950 of the frame 910 than the remaining inflow crowns of the inflow end 940 of the frame 910.

When the transcatheter aortic valve prosthesis 900 is deployed in situ, the non-flared strut $918_1$ are positioned to align with a portion of the conduction system of the heart. For example, the non-flared strut $918_1$ may be aligned with the left bundle branch of the heart when the transcatheter aortic valve prosthesis 900 is deployed in situ. Due to the presence of the non-flared strut $918_1$, the outward radial force exerted by the frame 910 of the transcatheter aortic valve prosthesis 900 on the left bundle branch is reduced as compared to a frame that does not include non-flared strut $918_1$. Thus, the frame 910 of the transcatheter aortic valve prosthesis 900 is less likely to negatively impact the conduction system of the heart.

Rather than a conduction protection cell or window, any frame described herein may include thinner struts that are positioned to align in situ with a portion of the conduction system of the heart to reduce conduction disturbances to the anatomy. More particularly, at the inflow end of the frame, the frame includes a row of struts that includes standard struts and thinner struts. Each standard strut has a first thickness profile, and each thinner strut has a thickness profile that is different from the first thickness profile. The first thickness profile of the standard strut includes a uniform thickness along an entire length thereof. To form each thinner strut, a portion or section of a standard strut is removed or cut-out to form the thinner strut with a different thickness profile than the standard strut. Stated another way, each thinner strut includes a cut-out portion. The cut-out portion may be triangular, rectangular, or semi-circular.

FIGS. 29A-29F depict an embodiment of a transcatheter aortic valve prosthesis 1000 that includes one or more thinner struts 1018 that have a reduced thickness compared to the thickness of the rest of the standard struts 1011 of the frame 1010. The frame 1010 of the transcatheter aortic valve prosthesis 1000 is the same as the frame 810 described above, except that the frame 1010 includes the thinner struts 1018 rather than the non-flared struts 818 of the frame 810. The thinner struts 1018 deflect with ease and apply a reduced outward radial force onto the conduction system of the heart.

Figure 29A:
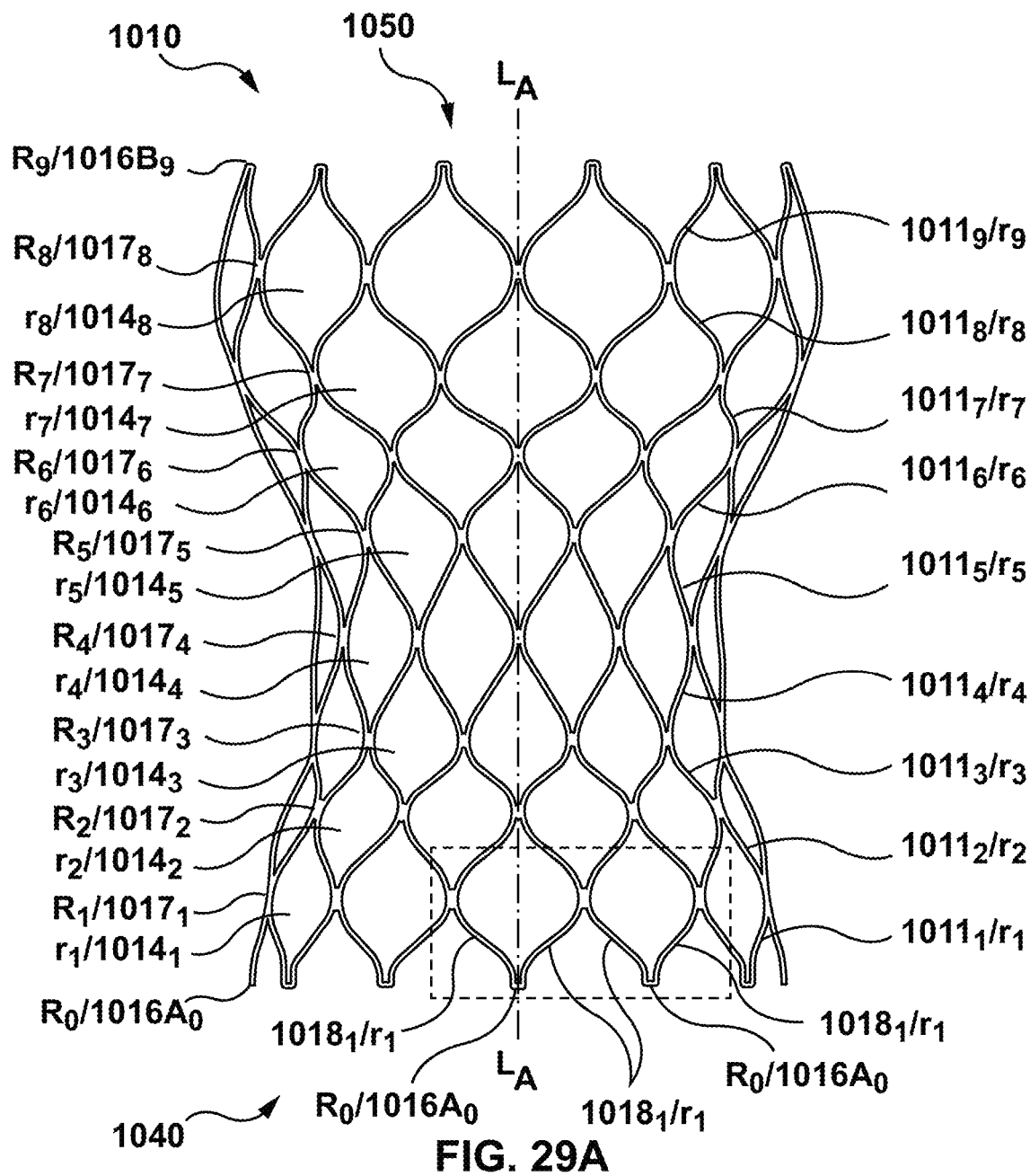
FIG. 29A depicts a side view of a frame of a transcatheter aortic valve prosthesis according to another embodiment hereof, wherein the frame includes four thinner struts with a reduced thickness.
Figure 29B:
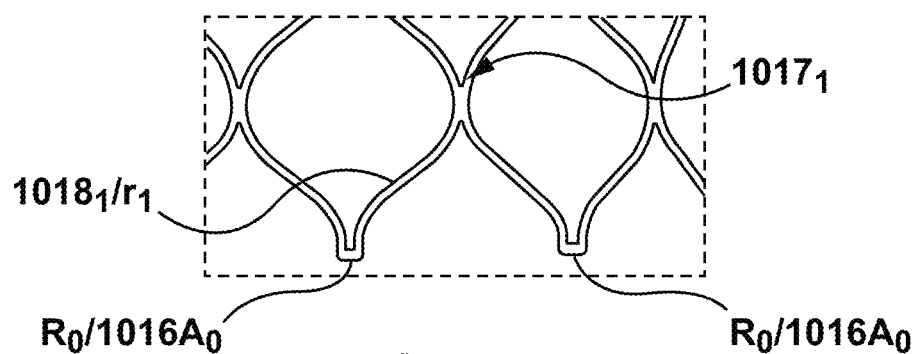
FIG. 29B depicts a close-up view of inflow crowns, struts, and nodes of the frame of the transcatheter aortic valve prosthesis of FIG. 29A.
Figure 29C:
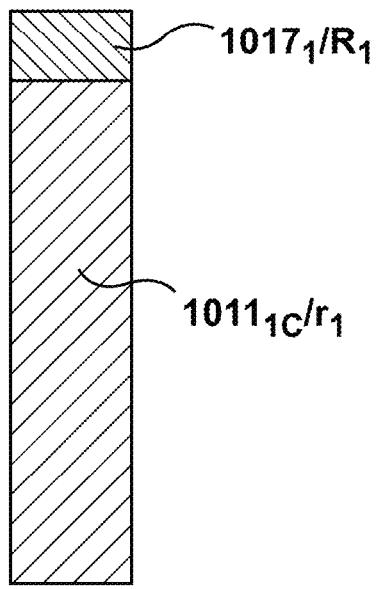
FIGS. 29C-29F depict close-ups of various thinner strut embodiments of the frame of the transcatheter aortic valve prosthesis of FIG. 29A.

FIG. 29A depicts the frame 1010 of the transcatheter aortic valve prosthesis 1000 and illustrates a region containing exactly four adjacent thinner struts $1018_1$ in the row $r_1$ and the two inflow crowns $1016A_O$ in the row $R_O$ that the four adjacent thinner struts $1018_1$ come together to form. FIG. 29B depicts a close-up view of the inflow crowns $1016_O$ in the row $R_O$, the struts $1011_1$ in the row $r_1$, and the nodes $1017_1$ in the row $R_1$. FIG. 29C is a schematic side view of a standard strut $1011_1$ in the row $r_1$ and a node $1017_1$ in the row $R_1$. In the embodiments shown, the standard struts $1011_1$ within the row $r_1$ have the same thickness and the thickness is uniform. The uniform thickness of the standard struts $1011_1$ may be between 0.45-0.48 mm.

Figure 29D:
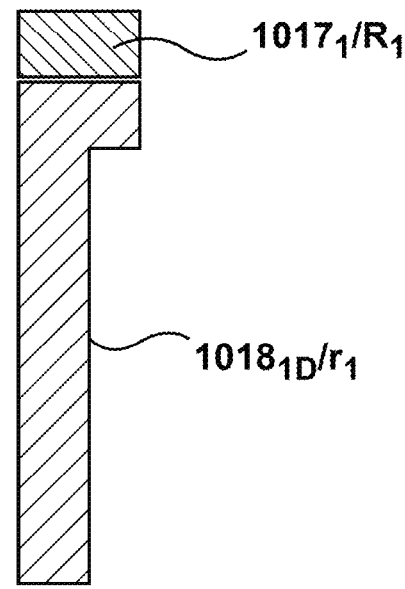
Figure 29E:
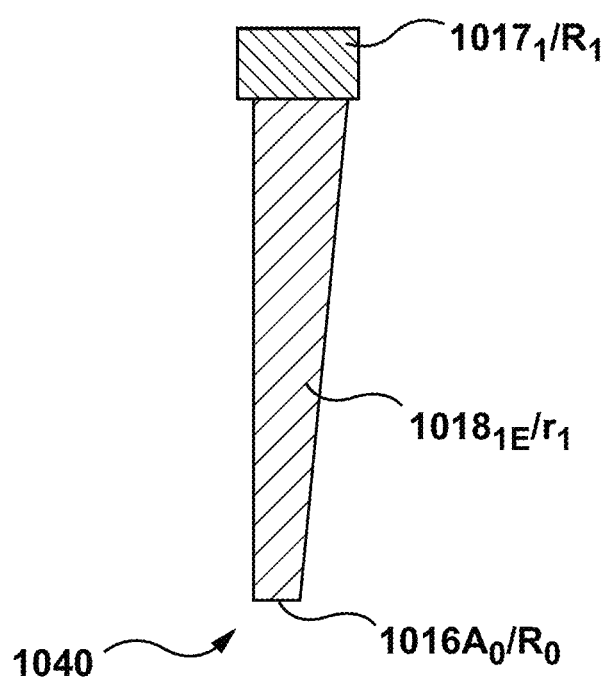
Figure 29F:
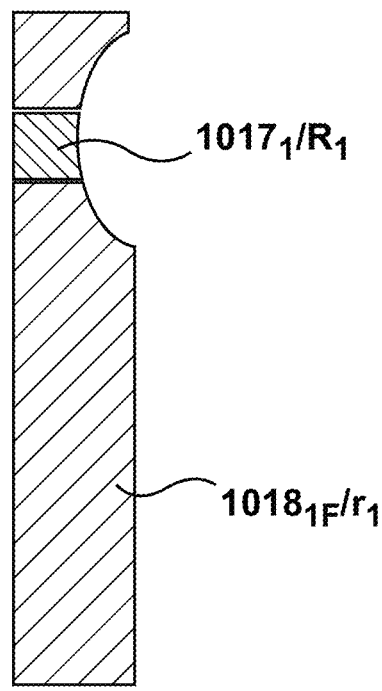

FIGS. 29D-29F illustrate various configurations for the thinner struts $1018_1$ of FIG. 29A. FIG. 29D depicts a schematic side view of a thinner strut $1018_{1D}$ having a rectangular-shaped cut-out portion to reduce the thickness of the strut. In the embodiment of FIG. 29D, the cut-out portion reduces the thickness of the thinner strut $1018_{1D}$ by between 35% and 45% relative the thickness of a standard strut $1011_1$ within the row $r_1$. FIG. 29E depicts a schematic side view of a thinner strut $1018_{1E}$ having a thickness that tapers or decreases in a continuous manner in a direction towards the inflow end 1040 of the frame 1010. In other words, the thinner strut $1018_{1E}$ shown in FIG. 29E has a triangular-shaped cut-out portion to reduce the thickness of the strut. In the embodiment of FIG. 29E, the triangular cut-out portion reduces the thickness of the thinner strut $1018_{1E}$ by between 20% and 30% relative the thickness of a standard strut $1011_1$ within the row $r_1$. FIG. 29F depicts a schematic side view of a thinner strut $1018_{1F}$ having a semi-circular shaped cut-out portion at the node $1017_1$ in the row $R_1$. The reduced thickness of the thinner strut $1018_{1F}$ at the node $1017_1$ shown in FIG. 29F would allow the thinner strut $1018_{1F}$ in the row $r_1$ to bend at the node $1017_1$ and deflect with ease to reduce conduction disturbances or damage to the anatomy of the conduction system. In the embodiment of FIG. 29F, the cut-out portion reduces the thickness of the thinner strut $1018_{1F}$ by between 5% and 15% relative the thickness of a standard strut $1011_1$ within the row $r_1$.

When the transcatheter aortic valve prosthesis 1000 is deployed in situ, the thinner struts 1018 are positioned to align with a portion of the conduction system of the heart. For example, the thinner struts 1018 may be aligned with the left bundle branch of the heart when the transcatheter aortic valve prosthesis 1000 is deployed in situ. Due to the presence of the thinner struts 1018, the outward radial force exerted by the frame 1010 of the transcatheter aortic valve prosthesis 1000 on the left bundle branch is reduced as compared to a frame that does not include thinner struts 1018. Thus, the frame 1010 of the transcatheter aortic valve prosthesis 1000 is less likely to negatively impact the conduction system of the heart.

It should be understood that various aspects disclosed herein may be combined in different combinations than the combinations specifically presented in the description and accompanying drawings. More particularly, the inflow end of any of frames 110, 210, 310, 410 may be modified to include a window, a conduction protection cell, a plurality of non-flared struts, or a plurality of thinner struts as described in FIGS. 24-29F herein. Similarly, any of the frames 510, 610, 710 may be modified such that the access cells thereof have a different configuration than shown, and the midportion of any of frames 810, 910, 1010 may be modified to include relatively enlarged access cells similar to those shown on frames 110, 210, 310, 410. It should also be understood that, depending on the example, certain acts or events of any of the processes or methods described herein may be performed in a different sequence, may be added, merged, or left out altogether (e.g., all described acts or events may not be necessary to carry out the techniques).

The invention claimed is:

1. A transcatheter aortic valve prosthesis for replacement of a native heart valve, the transcatheter aortic valve prosthesis comprising:
    a frame having a plurality of struts, a plurality of crowns at an inflow end, a plurality of crowns at an outflow end, a plurality of commissure posts or commissure cells, a plurality of first cells, and at least one access cell, wherein the frame includes a row of the plurality of struts which includes a plurality of standard struts and a plurality of optimized struts, each standard strut of the plurality of standard struts having a first width profile and a first length, and each optimized strut of the plurality of optimized struts having a width profile that is different from the first width profile and a length that is different from the first length; and a valve component including two or more valve leaflets disposed within the frame, wherein a commissure is formed where two valve leaflets of the two or more valve leaflets are attached to each other and each commissure is secured to a commissure post or commissure cell of the plurality of commissure posts or commissure cells of the frame, and wherein an area of a first cell directly adjacent to the at least one access cell has a first area and the at least one access cell has a second area, the second area being at least twice as large as the first area, and wherein the at least one access cell is centered in a circumferential direction between two commissure posts or commissure cells of the plurality of commissure posts or commissure cells of the frame, and wherein the row of the plurality of struts which includes the plurality of standard struts and the plurality of optimized struts is disposed at an inflow end or an outflow end of the at least one access cell, and wherein the frame includes at least three rows of struts between the inflow end of the frame and the inflow end of the at least one access cell.

2. A transcatheter aortic valve prosthesis for replacement of a native heart valve, the transcatheter aortic valve prosthesis comprising:

a frame having a plurality of struts, a plurality of crowns at an inflow end, a plurality of crowns at an outflow end, a plurality of commissure posts or commissure cells, a plurality of first cells, and at least one access cell, wherein the frame includes a row of the plurality of struts which includes a plurality of standard struts and a plurality of optimized struts, each standard strut of the plurality of standard struts having a first width profile and a first length, and each optimized strut of the plurality of optimized struts having a width profile that is different from the first width profile and a length that is different from the first length; and a valve component including two or more valve leaflets disposed within the frame, wherein a commissure is formed where two valve leaflets of the two or more valve leaflets are attached to each other and each commissure is secured to a commissure post or commissure cell of the plurality of commissure posts or commissure cells of the frame, and wherein an area of a first cell directly adjacent to the at least one access cell has a first area and the at least one access cell has a second area, the second area being at least twice as large as the first area, wherein the first area is approximately 25% of the second area, and wherein the at least one access cell is centered in a circumferential direction between two commissure posts or commissure cells of the plurality of commissure posts or commissure cells of the frame, and wherein the row of the plurality of struts which includes the plurality of standard struts and the plurality of optimized struts is disposed at an inflow end or an outflow end of the at least one access cell.

3. The transcatheter aortic valve prosthesis of claim 2, wherein the plurality of optimized struts include a first optimized strut, a second optimized strut, a third optimized strut, and a fourth optimized strut, and wherein the first optimized strut and the second optimized strut enclose a portion of the at least one access cell, and wherein the third optimized strut is disposed directly adjacent to the first optimized strut and the fourth optimized strut is disposed directly adjacent to the second optimized strut.

4. The transcatheter aortic valve prosthesis of claim 2, wherein the row of the plurality of struts which includes the plurality of standard struts and the plurality of optimized struts is a first row and the first row is disposed at the inflow end of the at least one access cell, and wherein the frame also includes a second row of the plurality of struts which includes the plurality of standard struts and the plurality of optimized struts and the second row is disposed at the outflow end of the at least one access cell.

5. The transcatheter aortic valve prosthesis of claim 2, wherein the frame includes exactly three access cells and exactly three commissure cells.

6. The transcatheter aortic valve prosthesis of claim 2, wherein the frame includes exactly three access cells and each access cell is disposed in a circumferential direction between two first cells.

7. The transcatheter aortic valve prosthesis of claim 1, wherein the first area is approximately 33% of the second area.

8. The transcatheter aortic valve prosthesis of claim 1, wherein the first area is approximately 14% of the second area.

9. The transcatheter aortic valve prosthesis of claim 1, wherein the first area is approximately 12% of the second area.

10. The transcatheter aortic valve prosthesis of claim 1, wherein the plurality of optimized struts include a first optimized strut, a second optimized strut, a third optimized strut, and a fourth optimized strut, and wherein the first optimized strut and the second optimized strut enclose a portion of the at least one access cell, and wherein the third optimized strut is disposed directly adjacent to the first optimized strut and the fourth optimized strut is disposed directly adjacent to the second optimized strut.

11. The transcatheter aortic valve prosthesis of claim 1, wherein the row of the plurality of struts which includes the plurality of standard struts and the plurality of optimized struts is a first row and the first row is disposed at the inflow end of the at least one access cell, and wherein the frame also includes a second row of the plurality of struts which includes the plurality of standard struts and the plurality of optimized struts and the second row is disposed at the outflow end of the at least one access cell.

12. A transcatheter aortic valve prosthesis for replacement of a native heart valve, the transcatheter aortic valve prosthesis comprising:

a frame having a plurality of struts, a plurality of crowns at an inflow end, a plurality of crowns at an outflow end, a plurality of commissure posts or commissure cells, a plurality of first cells, and at least one access cell, wherein the frame includes a row of the plurality of struts which includes a plurality of standard struts and a plurality of optimized struts, each standard strut of the plurality of standard struts having a first width profile and a first length, and each optimized strut of the plurality of optimized struts having a width profile that is different from the first width profile and a length that is different from the first length; and a valve component including two or more valve leaflets disposed within the frame, wherein a commissure is formed where two valve leaflets of the two or more valve leaflets are attached to each other and each commissure is secured to a commissure post or commissure cell of the plurality of commissure posts or commissure cells of the frame, and wherein an area of a first cell directly adjacent to the at least one access cell has a first area and the at least one access cell has a second area, the second area being at least twice as large as the first area, and wherein the at least one access cell is centered in a circumferential direction between two commissure posts or commissure cells of the plurality of commissure posts or commissure cells of the frame, and wherein the row of the plurality of struts which includes the plurality of standard struts and the plurality of optimized struts is disposed at an inflow end or an outflow end of the at least one access cell, and wherein the frame includes exactly fifteen crowns at the inflow end, exactly fifteen crowns at the outflow end, at least nine rows of first cells, and exactly three access cells.

13. The transcatheter aortic valve prosthesis of claim 12, wherein the frame includes exactly three commissure cells.

14. The transcatheter aortic valve prosthesis of claim 12, wherein the plurality of optimized struts include a first optimized strut, a second optimized strut, a third optimized strut, and a fourth optimized strut, and wherein the first optimized strut and the second optimized strut enclose a portion of the at least one access cell, and wherein the third optimized strut is disposed directly adjacent to the first optimized strut and the fourth optimized strut is disposed directly adjacent to the second optimized strut.

15. The transcatheter aortic valve prosthesis of claim 12, wherein the row of the plurality of struts which includes the plurality of standard struts and the plurality of optimized struts is a first row and the first row is disposed at the inflow end of the at least one access cell, and wherein the frame also includes a second row of the plurality of struts which includes the plurality of standard struts and the plurality of optimized struts and the second row is disposed at the outflow end of the at least one access cell.

16. The transcatheter aortic valve prosthesis of claim 12, wherein the frame includes exactly three access cells and exactly three commissure cells.

17. The transcatheter aortic valve prosthesis of claim 12, wherein the frame includes exactly three access cells and each access cell is disposed in a circumferential direction between two first cells.

18. The transcatheter aortic valve prosthesis of claim 1, wherein the frame includes exactly nine crowns at the inflow end, exactly nine crowns at the outflow end, at least four rows of first cells, and exactly one row of access cells.

19. The transcatheter aortic valve prosthesis of claim 18, wherein the one row of access cells includes exactly nine access cells.

20. The transcatheter aortic valve prosthesis of claim 1, wherein the frame includes exactly twelve crowns at the inflow end, exactly six crowns at the outflow end, at least four rows of first cells, and exactly one row of access cells.

21. The transcatheter aortic valve prosthesis of claim 20, wherein the one row of access cells includes exactly six access cells.

22. The transcatheter aortic valve prosthesis of claim 1, wherein the frame includes exactly twelve crowns at the inflow end, exactly twelve crowns at the outflow end, at least seven rows of first cells, and exactly one row of access cells.

23. The transcatheter aortic valve prosthesis of claim 1, wherein the frame also includes a window disposed at the inflow end of the frame or a conduction protection cell disposed at the inflow end of the frame; wherein a first cell directly adjacent to the window or the conduction protection cell has a first area and the least one window or the conduction protection cell has a second area, the second area being at least twice as large as the first area, and wherein the least one window or the conduction protection is positioned to align with a portion of the conduction system of the heart in situ.

24. The transcatheter aortic valve prosthesis of claim 23, wherein the least one window or the conduction protection cell has a first area extending approximately 60 degrees of a circumference of the frame.

25. The transcatheter aortic valve prosthesis of claim 24, wherein the frame includes the conduction protection cell disposed at the inflow end of the frame that is defined by crowns and struts of the inflow end of the frame.

26. The transcatheter aortic valve prosthesis of claim 24, wherein the frame includes the window disposed at the inflow end of the frame that creates a circumferential gap along the inflow end of the frame that does not include any crowns or struts of the frame.

27. The transcatheter aortic valve prosthesis of claim 26, further comprising a frame support section disposed within the window to support the circumferential gap created by the window, the frame support section being formed from a polymeric material or a fabric material.

28. The transcatheter aortic valve prosthesis of claim 27, wherein the frame support section includes at least four struts that form a diamond-shaped cell.

29. The transcatheter aortic valve prosthesis of claim 28, wherein the frame support section further includes at least three struts that attach the diamond-shaped cell to the frame.

30. The transcatheter aortic valve prosthesis of claim 28, wherein two of the at least four struts that form the diamond-shaped cell form a polymeric or fabric crown at the inflow end of the frame, the polymeric or fabric crown being longitudinally aligned with the plurality of crowns at the inflow end of the frame.

31. The transcatheter aortic valve prosthesis of claim 1, wherein the inflow end of the frame includes a row of the plurality of struts which includes a plurality of standard struts and a plurality of non-flared struts, wherein each standard strut of the plurality of standard struts flares radially outward when the frame is in an expanded configuration and wherein each non-flared strut of the plurality of non-flared struts does not flare radially outward when the frame is in the expanded configuration such that crowns disposed between a pair of non-flared struts at the inflow end are disposed radially inward relative to crowns disposed between a pair of standard struts, and wherein the non-flared struts of the frame are positioned to align with a portion of the conduction system of the heart in situ.

32. The transcatheter aortic valve prosthesis of claim 31, wherein crowns disposed between a pair of non-flared struts at the inflow end are displaced radially inward from a circumference of the frame outlined by the rest of the crowns at the inflow end.

33. The transcatheter aortic valve prosthesis of claim 31, wherein each non-flared strut of the plurality of non-flared struts extends radially inwards relative to each standard strut.

34. The transcatheter aortic valve prosthesis of claim 31, wherein each non-flared strut of the plurality of non-flared struts has a shorter height than a height of the standard struts.

35. The transcatheter aortic valve prosthesis of claim 34, wherein each non-flared strut of the plurality of non-flared struts has a first height that is 5-15% shorter than a second height of the standard struts.

36. A transcatheter aortic valve prosthesis for replacement of a native heart valve, the transcatheter aortic valve prosthesis comprising:
- a frame having a plurality of struts, a plurality of crowns at an inflow end, a plurality of crowns at an outflow end, a plurality of commissure posts or commissure cells, and a plurality of cells; and
- a valve component including two or more valve leaflets disposed within the frame, wherein a commissure is formed where two valve leaflets of the two or more valve leaflets are attached to each other and each commissure is secured to a commissure post or commissure cell of the plurality of commissure posts or commissure cells of the frame, and
- wherein the inflow end of the frame includes a row of the plurality of struts which includes a plurality of standard struts and a plurality of thinner struts, wherein each standard strut of the plurality of standard struts has a first thickness profile, and each thinner strut of the plurality of thinner struts has a thickness profile that is different from the first thickness profile, and wherein the thinner struts of the frame are positioned to align with a portion of the conduction system of the heart in situ.

37. The transcatheter aortic valve prosthesis of claim 36, wherein each thinner strut of the plurality of thinner struts includes a cut-out portion.

38. The transcatheter aortic valve prosthesis of claim 36, wherein the first thickness profile is uniform thickness along an entire length of each standard strut.

\* \* \* \* \*